United States Patent
Shah et al.

(10) Patent No.: US 9,163,273 B2
(45) Date of Patent: Oct. 20, 2015

(54) BIOSENSORS AND METHODS FOR MAKING AND USING THEM

(75) Inventors: Rajiv Shah, Rancho Palos Verdes, CA (US); Gopikrishnan Soundararajan, Irvine, CA (US); Rebecca K. Gottlieb, Culver City, CA (US); Udo Hoss, Sherman Oaks, CA (US); Eric A. Grovender, Minneapolis, MN (US); Shaun M. Pendo, Wofford Heights, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 441 days.

(21) Appl. No.: 12/784,220

(22) Filed: May 20, 2010

(65) Prior Publication Data

US 2010/0280347 A1    Nov. 4, 2010

Related U.S. Application Data

(62) Division of application No. 11/301,512, filed on Dec. 13, 2005, now Pat. No. 7,813,780.

(51) Int. Cl.
*A61B 5/05* (2006.01)
*C12Q 1/00* (2006.01)

(52) U.S. Cl.
CPC ..................................... *C12Q 1/006* (2013.01)

(58) Field of Classification Search
CPC ..... A61B 5/145; A61B 5/1468; A61B 5/1473
USPC ........ 600/306, 319, 345–347, 365; 435/4, 14; 436/68; 422/50, 420–429; 702/23; 604/64–66

See application file for complete search history.

(56) References Cited

U.S. PATENT DOCUMENTS

| | | |
|---|---|---|
| 2,402,950 A | 7/1946 | Culver et al. |
| 2,519,541 A | 8/1950 | Bryant |
| 2,899,658 A | 8/1959 | Bean, Jr. |
| 4,034,959 A | 7/1977 | Morrison |
| 4,104,099 A | 8/1978 | Scherrer |
| 4,163,544 A | 8/1979 | Fowler et al. |
| 4,356,074 A | 10/1982 | Johnson |

(Continued)

FOREIGN PATENT DOCUMENTS

| | | |
|---|---|---|
| DE | 242 240 A1 | 1/1987 |
| EP | 0 216 499 A2 | 4/1987 |

(Continued)

OTHER PUBLICATIONS

Desai, T.A. et al., "Nanoporous anit-fouling silicon membranes for biosensor applications," Biosensors and Nioelectronics, vol. 15, 2000, pp. 453-462, XP002433717.

(Continued)

*Primary Examiner* — Michael D'Angelo
(74) *Attorney, Agent, or Firm* — Gates & Cooper LLP

(57) ABSTRACT

Embodiments of the invention provide analyte sensors having optimized permselective membranes and methods for making and using such sensors. Embodiments of the invention also provide analyte sensors such as those having porous matrices coated with an analyte sensing composition and methods for making and using such sensors. Illustrative embodiments include electrochemical glucose sensors having glucose oxidase coatings.

16 Claims, 20 Drawing Sheets

(56) References Cited

U.S. PATENT DOCUMENTS

| | | |
|---|---|---|
| 4,373,009 A | 2/1983 | Winn |
| 4,373,527 A | 2/1983 | Fischell |
| 4,560,375 A | 12/1985 | Schulte et al. |
| 4,568,250 A | 2/1986 | Falk et al. |
| 4,569,641 A | 2/1986 | Falk et al. |
| 4,573,994 A | 3/1986 | Fischell et al. |
| 4,626,244 A | 12/1986 | Reinicke |
| 4,636,150 A | 1/1987 | Falk et al. |
| 4,654,006 A | 3/1987 | Kusano et al. |
| 4,714,234 A | 12/1987 | Falk et al. |
| 4,759,828 A | 7/1988 | Young et al. |
| 4,769,013 A | 9/1988 | Lorenz et al. |
| 4,783,441 A | 11/1988 | Thurow |
| 4,890,620 A | 1/1990 | Gough |
| 4,897,173 A | 1/1990 | Nankai et al. |
| 4,950,256 A | 8/1990 | Luther et al. |
| 4,958,661 A | 9/1990 | Holtermann et al. |
| 5,001,009 A | 3/1991 | Whitbourne |
| 5,019,260 A | 5/1991 | Gsell et al. |
| 5,077,210 A | 12/1991 | Eigler et al. |
| 5,108,819 A | 4/1992 | Heller et al. |
| 5,128,170 A | 7/1992 | Matsuda et al. |
| 5,165,407 A | 11/1992 | Wilson et al. |
| 5,168,104 A | 12/1992 | Li et al. |
| 5,178,366 A | 1/1993 | Kojima et al. |
| 5,183,472 A | 2/1993 | Jaehrling et al. |
| 5,196,088 A | 3/1993 | Soda |
| 5,200,051 A | 4/1993 | Cozzette et al. |
| 5,212,050 A | 5/1993 | Mier et al. |
| 5,229,172 A | 7/1993 | Cahalan et al. |
| 5,256,271 A * | 10/1993 | Ikariyama et al. ............ 205/109 |
| 5,281,324 A | 1/1994 | Kiesele et al. |
| 5,288,636 A | 2/1994 | Pollmann et al. |
| 5,299,571 A | 4/1994 | Mastrototaro |
| 5,322,063 A | 6/1994 | Allen et al. |
| 5,328,954 A | 7/1994 | Sarangapani |
| 5,330,911 A | 7/1994 | Hubbell et al. |
| 5,331,027 A | 7/1994 | Whitbourne |
| 5,352,348 A | 10/1994 | Young et al. |
| 5,390,671 A | 2/1995 | Lord et al. |
| 5,390,691 A | 2/1995 | Sproule |
| 5,391,250 A | 2/1995 | Cheney, II et al. |
| 5,411,647 A | 5/1995 | Johnson et al. |
| 5,415,938 A | 5/1995 | Cahalan et al. |
| 5,422,246 A * | 6/1995 | Koopal et al. .............. 204/403.1 |
| 5,433,710 A | 7/1995 | Van Antwerp et al. |
| 5,482,473 A | 1/1996 | Lord et al. |
| 5,568,806 A | 10/1996 | Cheney, II et al. |
| 5,607,475 A | 3/1997 | Cahalan et al. |
| 5,609,629 A | 3/1997 | Fearnot et al. |
| 5,620,738 A | 4/1997 | Fan et al. |
| 5,643,681 A | 7/1997 | Voorhees et al. |
| 5,648,442 A | 7/1997 | Bowers et al. |
| 5,662,960 A | 9/1997 | Hostettler et al. |
| 5,672,638 A | 9/1997 | Verhoeven et al. |
| 5,702,754 A | 12/1997 | Zhong |
| 5,702,818 A | 12/1997 | Cahalan et al. |
| 5,711,959 A | 1/1998 | Kohler et al. |
| 5,773,270 A | 6/1998 | D'Orazio et al. |
| 5,777,060 A | 7/1998 | Van Antwerp |
| 5,786,439 A | 7/1998 | Van Antwerp et al. |
| 5,804,048 A | 9/1998 | Wong et al. |
| 5,809,242 A | 9/1998 | Shaw et al. |
| 5,858,186 A | 1/1999 | Glass |
| 5,913,040 A | 6/1999 | Rakavy et al. |
| 5,939,208 A | 8/1999 | Stoy |
| 5,964,993 A | 10/1999 | Blubaugh, Jr. et al. |
| 5,972,199 A | 10/1999 | Heller et al. |
| 6,011,537 A | 1/2000 | Slotznick |
| 6,013,855 A | 1/2000 | McPherson et al. |
| 6,103,033 A | 8/2000 | Say et al. |
| 6,162,611 A | 12/2000 | Heller et al. |
| 6,340,421 B1 | 1/2002 | Vachon et al. |
| 6,368,274 B1 | 4/2002 | Van Antwerp et al. |
| 6,411,998 B1 | 6/2002 | Bryant et al. |
| 6,413,393 B1 | 7/2002 | Van Antwerp et al. |
| 6,475,750 B1 | 11/2002 | Han et al. |
| 6,497,729 B1 | 12/2002 | Moussy et al. |
| 6,551,276 B1 | 4/2003 | Mann et al. |
| 6,558,351 B1 | 5/2003 | Steil et al. |
| 7,637,868 B2 * | 12/2009 | Saint et al. .................... 600/365 |
| 8,060,174 B2 * | 11/2011 | Simpson et al. .............. 600/345 |
| 2003/0100040 A1 | 5/2003 | Bonnecaze et al. |
| 2004/0008956 A1 | 1/2004 | Frohne et al. |
| 2004/0009161 A1 | 1/2004 | Escary |
| 2004/0074785 A1 | 4/2004 | Holker et al. |
| 2005/0090607 A1 | 4/2005 | Tapsak et al. |
| 2005/0272989 A1 * | 12/2005 | Shah et al. .................... 600/345 |
| 2006/0052745 A1 | 3/2006 | Van Antwerp et al. |

FOREIGN PATENT DOCUMENTS

| | | |
|---|---|---|
| EP | 0 247 850 A1 | 12/1987 |
| EP | 0 562 370 A2 | 9/1993 |
| EP | 0 747 069 A2 | 12/1996 |
| EP | 0 826 382 A2 | 3/1998 |
| EP | 1 352 957 A1 | 10/2003 |
| JP | 60173452 | 9/1985 |
| WO | WO 98/07458 | 2/1998 |
| WO | WO 98/08553 | 3/1998 |
| WO | WO 98/10805 | 3/1998 |
| WO | WO 98/13685 | 4/1998 |
| WO | WO 98/19627 | 5/1998 |
| WO | WO 98/56293 | 12/1998 |
| WO | WO 99/21703 | 5/1999 |
| WO | WO 99/22993 | 5/1999 |
| WO | WO 99/45375 | 9/1999 |
| WO | WO 99/45387 | 9/1999 |
| WO | WO 99/56613 | 11/1999 |
| WO | WO 01/58348 | 8/2001 |
| WO | WO 02/053764 | 7/2002 |
| WO | WO 02/097416 | 12/2002 |
| WO | WO 2005/045394 | 5/2005 |
| WO | WO 2006/127694 | 11/2006 |

OTHER PUBLICATIONS

Flexible circuits at Extreme Density, 8 unnumbered pages of various dates (Metrigraphics, Wilmington, MA).

Kimura, J. et al., 1989, "Evaluation of an Albumin-Based, Spin-Coated, Enzyme-Immobilized Membrane for an Isfet Glucose Sensor by Computer Simulation," Journal of Membrane Science, 43:291-305.

Koudelka, M., et al., "Planar Amperometric Enzyme-Based Glucose Microelectrode", Sensors and Actuators, 18 (Elsevier Sequoia, the Netherlands—1989), pp. 157-165.

Koudelka, M., et al., "In-vivo Behaviour of Hypodermically Implanted Microfabricated Glucose Sensors", *Biosensors & Bioelectronics* 6, (Elsevier Science Publishers Ltd., England—1991) pp. 31-36.

Mastrototaro, John J., et al., "An electroenzymatic glucose sensor fabricated on a flexible substrate", *Sensors and Actuators B.5* (Elsevier Sequoia 1991), pp. 139-144.

"Metrigraphics Ion Beam Etching Capability", 1 page, no date (Metrigraphics, Wilmington, MA).

"3M Specifications and Design Guidelines, Microflex Circuits for IC Interconnect Solutions," pp. 1-32 (the entire document), 1997 (3M Electronic Products Division, Austin, TX).

"3M Offers More Solutions for the Semiconductor Industry", the entire document, 1997 (3M Electronic Products Division, Austin, TX).

"Microflex Solutions from 3M", the entire document, 1996 (3M Electronic Products Division, Austin, TX).

"5 Micron Wide Conductors and Spaces on . . . PZT, Alumina, Glass and Flexible Materials", 1 page, no date (Metrigraphics, Wilmington, MA).

Thurow et al., "Stabilisation of Dissolved Proteins Against Denaturation at Hydrophobic Interfaces," Diabetologia, 1984, 27: 212-218.

(56) References Cited

OTHER PUBLICATIONS

"Nanoporous anti-fouling silicon membranes for biosensor applications," Biosensors and Nioelectronics, vol. 15, 2000, pp. 453-462.
Urban, G., et al., "Miniaturized multi-enzyme biosensors integrated with pH sensors on flexible polymer carriers for in vivo applications", *Biosensors & Bioelectronics* 7 (Elsevier Science Publishers Ltd.—1992) pp. 733-739.
Wilke, D. et al., 1992, "Application of Redox Mediators in Enzyme Electrodes," Proc. Conf. Trends Electrochem. Biosens., pp. 155-161.
Yao, T., 1983, Analytica Chim. Acta, 148:27-33.

* cited by examiner

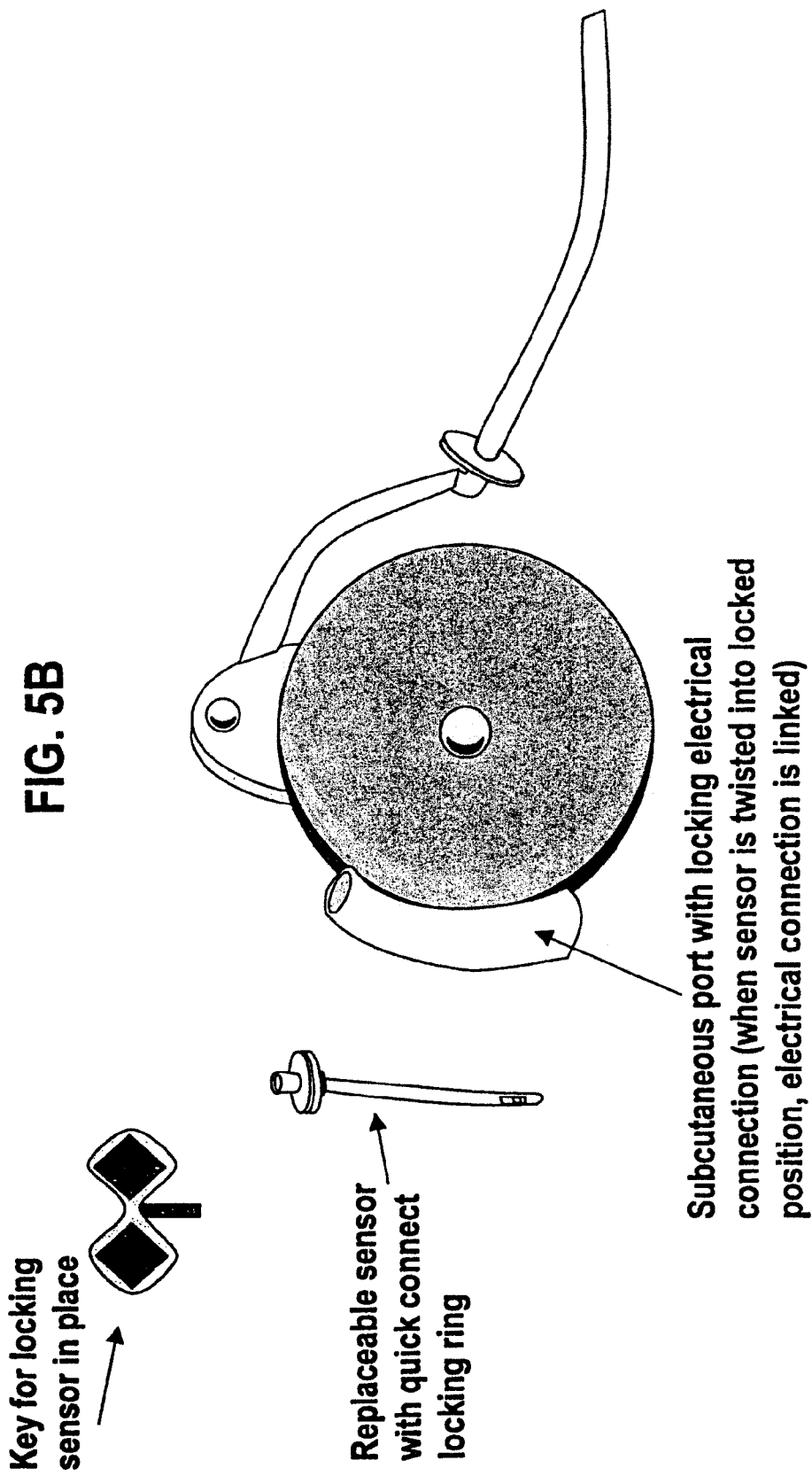

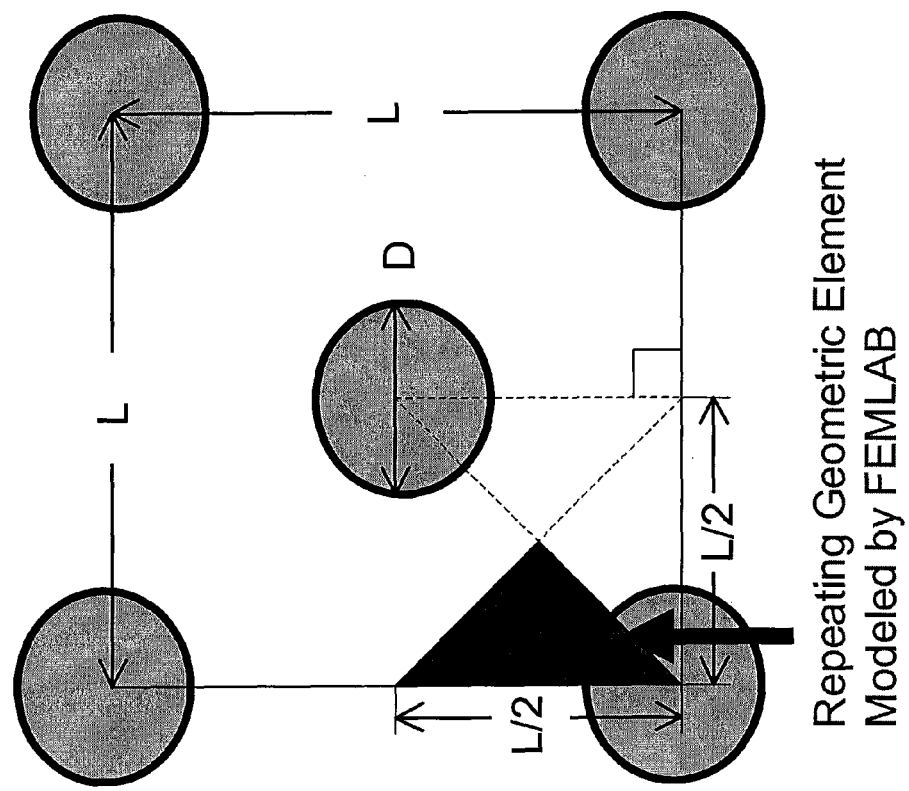

BIOSENSORS AND METHODS FOR MAKING AND USING THEM

CROSS REFERENCE TO RELATED APPLICATIONS

This application is a divisional of U.S. patent application Ser. No. 11/301,512 filed Dec. 13, 2005 (published as US-2007-0135698-A1) which is incorporated by reference herein and is related to U.S. patent application Ser. No. 10/273,767 filed Oct. 18, 2002 (published as US-2004-0074785-A1) and U.S. patent application Ser. No. 10/861,837, filed Jun. 4, 2004, the contents of both of which are incorporated herein by reference.

BACKGROUND OF THE INVENTION

1. Field of the Invention

The present invention relates to elements used in sensors for the detection and measurement of analytes such as glucose and lactate and methods for making and using these elements.

2. Description of Related Art

The assay of biochemical analytes such as glucose and lactate is important in a variety of clinical contexts. For example, the monitoring of glucose concentrations in fluids of the human body is of particular relevance to diabetes management. Continuously or intermittently operating glucose sensors, including sensors implanted in the human body, are sought for the management of diabetes, for example, for warning of imminent or actual hypoglycemia as well as its avoidance. The monitoring of lactate concentrations in fluids of the human body is useful in, but not limited to, the diagnosis and assessment of a number of medical conditions including trauma, myocardial infarction, congestive heart failure, pulmonary edema and septicemia.

Biomedical measuring devices commonly used by to monitor physiological variables include amperometric sensor devices that utilize electrodes modified with an appropriate enzyme coating. Sensors having such enzyme electrodes enable the user to determine the concentration of various analytes rapidly and with considerable accuracy, for example by utilizing the reaction of an enzyme and an analyte where this reaction utilizes a detectable coreactant and/or produces a detectable reaction product. For example, a number of glucose sensors have been developed that are based on the reaction between glucose and oxygen that is catalyzed by glucose oxidase (GOx) as shown in FIG. 1. In this context, the accurate measurement of physiological glucose concentrations using sensors known in the art, typically requires that both oxygen and water be present in excess. As glucose and oxygen diffuse into an immobilized enzyme layer on a sensor, the glucose reacts with oxygen to produce $H_2O_2$. Glucose can be detected electrochemically using the immobilized enzyme glucose oxidase coupled to oxygen and/or hydrogen peroxide-sensitive electrodes. The reaction results in a reduction in oxygen and the production of hydrogen peroxide proportional to the concentration of glucose in the sample medium. A typical device is composed of (but not limited to) at least two detecting electrodes, or at least one detecting electrode and a reference signal source, to sense the concentration of oxygen or hydrogen peroxide in the presence and absence of enzyme reaction. Additionally, the complete monitoring system typically contains an electronic sensing and control means for determining the difference in the concentration of the substances of interest. From this difference, the concentration of analytes such as glucose can be determined.

A wide variety of such analyte sensors as well as methods for making and using such sensors are known in the art. Examples of such sensors, sensor sets and methods for their production are described, for example, in U.S. Pat. Nos. 5,390,691, 5,391,250, 5,482,473, 5,299,571, 5,568,806 as well as PCT International Publication Numbers WO 01/58348, WO 03/034902, WO 03/035117, WO 03/035891, WO 03/023388, WO 03/022128, WO 03/022352, WO 03/023708, WO 03/036255, WO03/036310 and WO 03/074107, the contents of each of which are incorporated herein by reference.

SUMMARY OF THE INVENTION

Embodiments of the invention disclosed herein provide elements for use in analyte sensors of the type used, for example, in subcutaneous or transcutaneous monitoring of blood glucose levels in a diabetic patient. Embodiments of the invention disclosed herein further provide analyte sensors of the type used, for example, in a variety of clinical contexts such as with dialysis and/or extracorporeal membrane oxygenation protocols. More specifically, the disclosure provided herein teaches optimized analyte sensor designs and methods for making and using such sensors.

The invention disclosed herein has a number of embodiments. One embodiment is a permselective membrane for use with an analyte sensor (e.g. a glucose limiting membrane) which made from a material such as poly(dimethyl siloxane) and which optionally contains a plurality of pores disposed within it so as to facilitate the sensing of the analyte. Optionally one or more of the plurality of pores in the membrane is filled with a hydrophilic composition. Illustrative embodiments of the invention include a membrane for use with an implantable analyte sensor, the membrane including a first layer comprising a biocompatible polymer composition that is impermeable to immunoglobulins, yet permeable to oxygen, glucose and lactate; and a second layer coupled to the first layer comprising functionalized poly(dimethyl siloxane), functionalized poly(dimethyl siloxane) copolymer or a mixture of functionalized poly(dimethyl siloxane) and functionalized poly(dimethyl siloxane) copolymer. In this embodiment of the invention, the membrane is typically more permeable to oxygen than glucose and/or lactate. Optionally in this membrane for use with an implantable analyte sensor the first layer and/or the second layer comprises a plurality of pores disposed therein. In certain embodiments of the invention, at least one of the plurality of pores disposed in the second layer contains functionalized poly(dimethyl siloxane), functionalized poly(dimethyl siloxane) copolymer or a mixture of functionalized poly(dimethyl siloxane) and functionalized poly(dimethyl siloxane) copolymer of the second layer. In some embodiments of the invention, an adhesive layer can be disposed between the first and second layers, wherein the adhesive layer promotes adhesion between the first and second layers.

Any of the various constituent elements of the sensor can be combined with the other sensor elements disclosed herein or known in the art. Another exemplary embodiment of the invention is a composition designed to be implantable within a mammal that comprises a porous matrix having a surface coated with an immobilized enzyme, for example glucose oxidase, glucose dehydrogenase, lactate oxidase, hexokinase or lactate dehydrogenase. Typically the porous matrix coated with an immobilized enzyme is capable of acting as an electrode in an electrochemical sensor. Optionally the electrode in the electrochemical sensor consumes hydrogen peroxide.

The porous matrices used in various embodiments of the biosensors of the invention can be generated from a variety of materials and can be adapted to a variety of compositional configurations. In some embodiments of the invention, the porous matrix comprises a ceramic material and/or a metal and/or a macroporous polymer. Optionally the porous matrix comprises a lattice of particles. Typically the particles are spherical. In typical embodiments of the invention, porous matrix has a surface area that is at least 2, 4, 6, 8, 10, 12, 14, 16 or 18 times the surface area of a non-porous matrix of same dimensions. In certain embodiments of the invention, the porous matrix is at least 1, 10, 100, or 1000 microns thick.

A related embodiment of the invention is an analyte sensor apparatus for implantation within a mammal which includes a porous matrix having a surface coated with an immobilized enzyme, for example glucose oxidase. In one embodiment of this sensor design, the porous matrix comprises a working electrode; and the immobilized enzyme is disposed within an analyte sensing layer disposed on the working electrode, such that the analyte sensing layer detectably alters the electrical current at the working electrode in the presence of an analyte. Typically the sensor further comprises an analyte modulating layer disposed on the analyte sensing layer, wherein the analyte modulating layer modulates the diffusion of the analyte therethrough. Typically, the sensor further comprises an adhesion promoting layer disposed on the analyte sensing layer, wherein the adhesion promoting layer promotes the adhesion between the analyte sensing layer and an analyte modulating layer disposed on the analyte sensing layer. Optionally the sensor further comprises a protein layer disposed between the analyte sensing layer and the analyte modulating layer. Typically the sensor further comprises a cover layer disposed on at least a portion of the analyte modulating layer, wherein the cover layer further includes an aperture that exposes at least a portion of the analyte modulating layer to a solution comprising the analyte to be sensed.

A related embodiment of the invention is a method of making a sensor apparatus for implantation within a mammal comprising the steps of providing a layer comprising a porous matrix, forming an analyte sensing layer on the porous matrix, wherein the analyte sensing layer includes an enzyme such as glucose oxidase that can alter the electrical current at the surface of the porous matrix in the presence of an analyte so that the porous matrix having the analyte sensing layer formed thereon functions as an electrode. Such methods further include the steps of optionally forming a protein layer on the analyte sensing layer, forming an adhesion promoting layer on the analyte sensing layer or the optional protein layer, forming an analyte modulating layer disposed on the adhesion promoting layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer.

Another embodiment of the invention is a method of sensing an analyte within the body of a mammal, the method comprising implanting an analyte sensor in to the mammal, the analyte sensor comprising a porous matrix having an analyte sensing layer disposed thereon, wherein the analyte sensing layer detectably alters the electrical current at the surface of the porous matrix in the presence of an analyte so that the porous matrix having the analyte sensing layer formed thereon functions as an electrode, an optional protein layer disposed on the analyte sensing layer, an adhesion promoting layer disposed on the analyte sensing layer or the optional protein layer, wherein the adhesion promoting layer promotes the adhesion between the analyte sensing layer and an analyte modulating layer disposed on the analyte sensing layer, and an analyte modulating layer disposed on the analyte sensing layer, wherein the analyte modulating layer modulates the diffusion of the analyte therethrough, a cover layer disposed on at least a portion of the analyte modulating layer, wherein the cover layer further includes an aperture over at least a portion of the analyte modulating layer; and sensing an alteration in current at the electrical current and correlating the alteration in current with the presence of the analyte, so that the analyte is sensed.

Yet another embodiment of the invention is a method of immobilizing a protein on a rigid macroporous polymer comprising the steps of: combining the protein with the rigid macroporous polymer having functional moieties capable of crosslinking to a protein; and then adding a crosslinking agent capable of immobilizing the protein on the rigid macroporous polymer by crosslinking the functional moieties of the protein with the functional moieties of the rigid macroporous polymer so that the protein is immobilized on the rigid macroporous polymer. In certain embodiments of the invention, the rigid macroporous polymer having functional moieties capable of crosslinking to a protein is made by combining a rigid macroporous polymer having reactive epoxide moieties with a nucleophilic compound so that a rigid macroporous polymer having functional moieties capable of crosslinking to a protein is made.

Another embodiment of the invention is a method of immobilizing a protein on a rigid macroporous polymer comprising combining a protein having a sulfhydryl, amine, carboxyl or hydroxyl moiety with a rigid macroporous polymer having reactive epoxide moieties under reaction conditions that allow a nucleophilic reaction to occur between the sulfhydryl, amine, carboxyl or hydroxyl moieties on the protein and the epoxide moieties on the rigid macroporous polymer so that the protein is immobilized on the rigid macroporous polymer. In certain embodiments of this method, at least one nucleophilic moiety on the protein is blocked prior to combining the protein with the rigid macroporous polymer.

The invention also provides additional articles of manufacture including sensor elements, sensor sets and kits. In one such embodiment of the invention, a kit and/or sensor element or set, useful for the sensing an analyte as is described above, is provided. The kit and/or sensor set typically comprises a container, a label and a sensor as described above. The typical embodiment is a kit comprising a container and, within the container, an analyte sensor apparatus having a design as disclosed herein and instructions for using the analyte sensor apparatus.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE FIGURES

FIG. 2 provides a diagrammatic view of a typical analyte sensor configuration of the current invention. FIGS. 2A and 2B further show that one or more of the various constituent layers of the sensor (e.g. the adhesion promoting constituent 114) can be disposed between two or more of the other constituents within the sensor.

FIG. 4B illustrates a sensor design with 7 vias and 4 working electrodes where W=working electrode (+), C=counter electrode (−) and R=reference electrode.

FIG. 5B provides an illustration of a variation of this scheme where replaceable analyte sensors of the invention can be coupled with other medical devices such as medication infusion pumps, for example by the use of a port coupled to the medical device (e.g. a subcutaneous port with a locking electrical connection). The design provided in FIG. 5B, illustrates a replaceable sensor integrated with a port on the pump, wherein the port is a subcutaneous port with a locking electrical connection (when sensor is twisted into locked position, electrical connection is linked). Also shown in FIG. 5B is a replaceable sensor with quick connect locking ring and a key for locking the sensor in place.

FIGS. 12A-12H provide data from 3-modeling studies in combination with real-world mold microfabrication, PDMS molding, and sensor prototyping to produce optimized microfabricated permselective membranes. FIG. 12A shows a schematic of a repeating Array of Circles for PDMS Microfabrication. FIG. 12B shows a schematic of 3-D Geometry and Input Parameters Used by FEMLAB to Model the 30 μm Microporous PDMS Membrane as Part of an Enzymatic Electrochemical Glucose Sensor. FIG. 12C shows a schematic of a Steady-State Glucose Concentration Profile in a 30 μm Pore. FIG. 12D shows a schematic of a Steady-State Oxygen Concentration Profile in the 30 μm Microporous PDMS membrane. FIG. 12E shows a schematic of a Steady-State Oxygen Concentration Profile in a 30 μm Pore. FIG. 12F shows a schematic of a Steady-State Oxygen Concentration Profile along the X-axis of the Reactive Surface of a 30 μm Pore. FIG. 12G shows a schematic of a Steady-State Oxygen Concentration Profile in a 10 μm Pore. FIG. 12H shows a schematic of a Steady-State Oxygen Concentration Profile along the X-axis of the Reactive Surface of a 10 μm Pore.

DETAILED DESCRIPTION OF THE EMBODIMENTS

Figure 1:
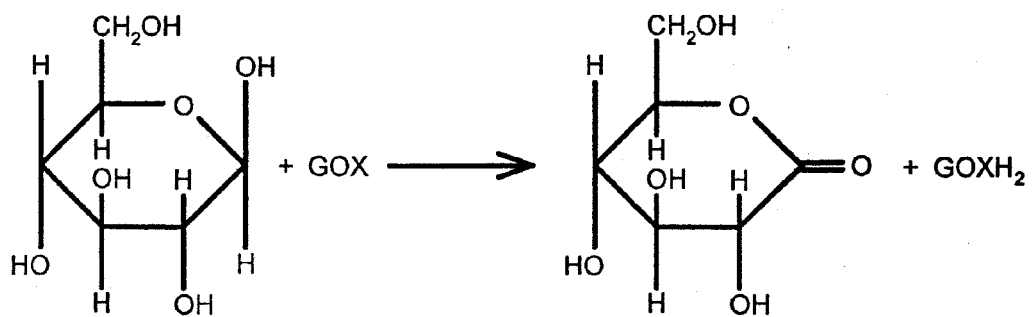
FIG. 1 provides a schematic of the well known reaction between glucose and glucose oxidase. As shown in a stepwise manner, this reaction involves glucose oxidase (GOx), glucose and oxygen in water. In the reductive half of the reaction, two protons and electrons are transferred from β-D-glucose to the enzyme yielding d-gluconolactone. In the oxidative half of the reaction, the enzyme is oxidized by molecular oxygen yielding hydrogen peroxide. The d-gluconolactone then reacts with water to hydrolyze the lactone ring and produce gluconic acid. In certain electrochemical sensors of the invention, the hydrogen peroxide produced by this reaction is oxidized at the working electrode ($H_2O_2 \rightarrow 2H^+ + O_2 + 2e^-$).
Figure 1:
Figure 1:
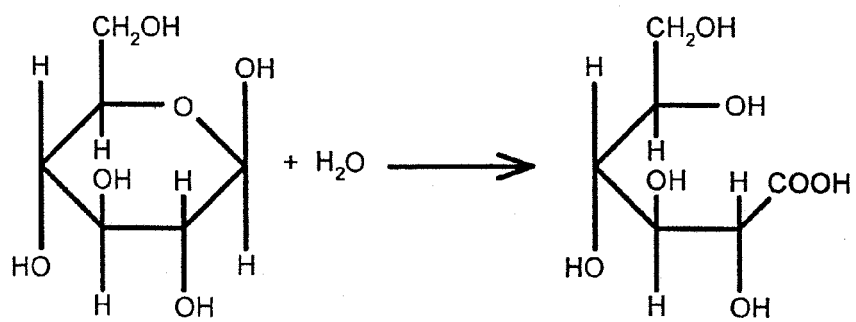

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted.

The term "analyte" as used herein is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to lactate. Salts, sugar, protein, fat, vitamins and hormones naturally occurring in blood or interstitial fluids can constitute analytes in certain embodiments. The analyte can be naturally present in the biological fluid or endogenous, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin. The metabolic products of drugs and pharmaceutical compositions are also contemplated analytes.

Embodiments of the invention disclosed herein provide sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their biospecificity. For example, a first class of glucose sensor designs use a very thin (<1 micron) layer of glucose oxidase (GOx) and bovine serum albumin that is either spray or spin coated onto the working electrode and cross-linked with glutaraldehyde. Alternatively, a second class of glucose sensor design employs a thick (~1 mm) hydrogel known as the Sensor Matrix Protein (SMP), which typically consists of an enzyme such as GOx and human serum albumin cross-linked together with a cross-linking agent such as glutaraldehyde. Relative to each other, the immobilized enzyme configurations of the two above-noted classes of sensor designs possess different advantages that serve to increase operational sensor life. Due to the close proximity of the immobilized GOx to the peroxide-consuming electrode, the first class of sensor designs are believed to possess significantly decreased enzyme deactivation rate constants. In comparison, the thick SMPs utilized in the second class of sensor designs can incorporate orders of magnitude more enzyme than the first class.

Many sensor designs utilize a matrix (or a plurality of matrices) such as an enzymatic hydrogel matrix to function. The term "matrix" is used herein according to its art accepted meaning of something within or from which something else originates, develops, takes form and/or is found. An exemplary enzymatic hydrogel matrix for example typically comprises a bio-sensing enzyme (e.g. glucose oxidase or lactate oxidase) and human serum albumin proteins that have been cross-linked together with a crosslinking agent such as glutaraldehyde to form a polymer network. This network is then swollen with an aqueous solution to form an enzymatic hydrogel matrix. The degree of swelling of this hydrogel frequently increases over a time-period of several weeks, and is presumably due to the degradation of network cross-links. Regardless of its cause, an observed consequence of this swelling is the protrusion of the hydrogel outside of the hole or "window" cut into the outer sensor tubing. This causes the sensor dimensions to exceed design specifications and has a negative impact on its analytical performance.

There is a need in the art for sensor elements and designs which provide enhanced material properties. Embodiments of the invention disclosed herein provide sensor elements having enhanced material properties and sensors constructed from such elements. The disclosure further provides methods for making and using such sensors. While some embodiments of the invention pertain to glucose and/or lactate sensors, a variety of the elements disclosed herein (e.g. porous enzyme matrices) can be adapted for use with any one of the wide variety of sensors known in the art. The analyte sensor elements, architectures and methods for making and using these elements that are disclosed herein can be used to establish a variety of layered sensor structures. Such sensors of the invention exhibit a surprising degree of flexibility and versatility, characteristic which allow a wide variety of sensor configurations to be designed to examine a wide variety of analyte species.

In typical embodiments of the present invention, the transduction of the analyte concentration into a processable signal is by electrochemical means. These transducers may include any of a wide variety of amperometric, potentiometric, or conductimetric base sensors known in the art. Moreover, the microfabrication sensor techniques and materials of the instant invention may be applied to other types of transducers (e.g., acoustic wave sensing devices, thermistors, gas-sensing electrodes, field-effect transistors, optical and evanescent field wave guides, and the like) fabricated in a substantially nonplanar, or alternatively, a substantially planar manner. A useful discussion and tabulation of transducers which may be exploited in a biosensor as well as the kinds of analytical applications in which each type of transducer or biosensor, in general, may be utilized is found in an article by Christopher R. Lowe in Trends in Biotech. 1984, 2(3), 59-65.

Specific aspects of the invention are discussed in detail in the following sections.

I. Typical Elements, Configurations and Analyte Sensors of the Invention

A. Optimized Sensor Elements of the Invention

Embodiments of the sensors disclosed herein incorporate one or more sensor elements having enhanced material properties. Embodiments of the invention disclosed herein further include optimized methods for making the sensors of the invention. The following paragraphs of this section provide a description of these embodiments.

Embodiments of invention disclosed herein provide individual elements and sensors which exhibit a combination of the independent advantages found in each of the two sensor classes disclosed above. For example a first embodiment of the invention immobilizes an enzyme onto a thick (1-1,000 micron), porous substrate which functions as an electrode in the sensor. In this context, the porous electrode is designed to exhibit an increased surface area, for example by constructing it from a lattice of equal-sized adjoining spheres. In one illustrative embodiment, glucose oxidase is immobilized on a thick (1-1,000 micron), porous metallic substrate that is manufactured from a lattice of equal-sized adjoining spheres and which function as a hydrogen peroxide-consuming electrode.

The advantage of such a thick, porous electrode matrices relative to thin, flat electrode matrices is demonstrated using Equation (1):

$$\frac{A_{avail}}{A_{proj}} = \frac{3L(1-\epsilon)\phi}{R} \qquad (1)$$

where the thick, porous electrode is modeled as a lattice of equal-sized adjoining spheres, while the thin electrode is modeled as a two-dimensional surface. The surface area available for enzyme or protein immobilization is $A_{avail}$, while the projected area of the electrode is $A_{proj}$. The porosity and thickness of the electrode are L and $\epsilon$, respectively. The spheres making-up the thick electrode are of radius R, while the fraction of the spheres' surface area available for enzyme or protein immobilization is $\phi$. For example, a porous electrode with L=25 µm, R=1 µm, $\delta$=0.5, and $\phi$=0.5 would possess more than 18 times the surface area for enzyme immobilization as compared to a thin electrode with same projected area.

The porosity range of the such as the porous electrode matrices discussed above is typically 5-99%, 10-99%, 20-99%, 30-99%, 40-99%, 50-99% or 60-99%. The porosity of matrices can be evaluated using any one of a variety of methods known in the art. In certain contexts for example, artisans may wish to examine porosity of a matrix via mercury porosimetry (see, e.g. U.S. Pat. No. 5,609,839), liquid intrusion porosimetry (see, e.g. U.S. Pat. No. 4,660,412), gas porosimetry (see, e.g. Dombrowski et al., Langmuir 16: 5041-5050 (2000) and Lastoskie et al., Journal of Physical Chemistry 97: 4786-4796 (1993)), or by cyclic voltametry and/or methods which employ size exclusion chromatography using marker molecules of various sizes and molecular weights (e.g. acetone, various globular proteins, blue dextran etc.).

The terms nano-porous, micro-porous and macro-porous are used when discussing certain embodiments of the porous matrices that are disclosed herein. For example, platinum-black is commonly used to increase the electrochemically effective surface area of a working electrode. Standard platinum-black electrodes have a great deal of porosity, with the pores being sized so that only very small molecules like $H_2$, $O_2$, and $H_2O$ can get inside them. Platinum-black electrodes having this characteristic are termed nano-porous. Such nano-pores have a size range that permits small molecules like $H_2$, $O_2$, and $H_2O$ the get inside them, but prevents larger molecules like GOx from getting inside. In certain embodiments of the invention, the electrodes used in the sensors have both nano- and micro-porosity. Micro-pores are characterized in that they are large enough to allow molecules such as GOx to be immobilized inside of them, but are small enough so that any molecule of GOx is relatively close (less than about 0.1, 1, or 2 microns) to the surface of the working electrode. Electrodes having this micro-porosity exhibit a number of desirable characteristics. For example, as the working electrode of an $H_2O_2$-based sensor consumes $H_2O_2$ and $H_2O_2$ is believed to contribute to the deactivation GOx over time, micro-porous electrodes that allow the placement of immobilized GOx in close proximity to an $H_2O_2$-consuming electrode will increase the lifetime of GOx in the sensor.

In another embodiment of the invention disclosed herein the hydrogel typically utilized in a variety of analyte sensors is replaced with an essentially rigid, non-swelling porous enzyme-polymer matrix. In this embodiment, bio-sensing enzymes can be stably immobilized via covalent bonding to a rigid, macroporous polymer that has optionally been molded into a specified shape. In this context, molded continuous rods of macroporous polymers have been developed for use as chromatographic separation media (see, e.g. U.S. Pat. No. 5,453,185 and WO 93/07945). Suitable polymers are essentially incompressible and do not change their overall size in response to changes in their solvating environment. Moreover, adjustments to the polymerization conditions can be used to control the morphology of the pores. Hence, highly porous (50-70%) polymers can be created that possess significant volume fractions of pores in the ranges of 1-100 nm and 100-3,000 nm (i.e. 20% and 80%, respectively). Polymers with this type of pore structure possess a very high specific surface area (i.e. 185 $m^2$/g), and are expected to allow for high enzyme immobilization densities (1-100 mg/mL). Various methods and compositions for making and using the above-noted porous matrices as well as analyte sensors which incorporate such matrices are further described in the sections below.

As also discussed in the sections below, yet another embodiment of the invention is a permselective membrane for use with an analyte sensor (e.g. a glucose limiting membrane) which made from a material such as poly(dimethyl siloxane) and which optionally contains a plurality of pores disposed within it so as to facilitate the sensing of the analyte. Optionally one or more of the plurality of pores in the membrane is filled with a hydrophilic composition. Illustrative embodiments of the invention include a membrane for use with an implantable analyte sensor, the membrane including a first layer comprising a biocompatible polymer composition that is impermeable to immunoglobulins, yet permeable to oxygen, glucose and lactate; and a second layer coupled to the first layer comprising functionalized poly(dimethyl siloxane), functionalized poly(dimethyl siloxane) copolymer or a mixture of functionalized poly(dimethyl siloxane) and functionalized poly(dimethyl siloxane) copolymer.

The optimized embodiments of the invention disclosed herein can be universally utilized and/or applied to a wide variety of sensor methods and designs. Consequently, the following sections describe illustrative sensor elements, configurations and methods that can incorporate these embodiments of the invention.

B. Diagrammatic Illustration of Typical Sensor Configurations

Figure 10:
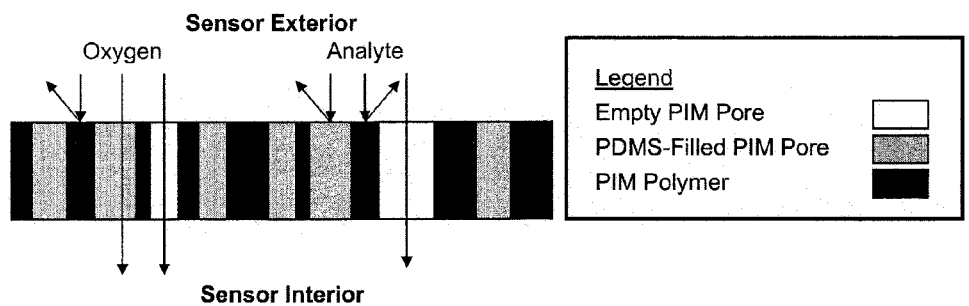
FIG. 10 provides an illustration of a cross-sectional view of a composite permselective membrane with a "pore-filled" morphology. In this membrane, analyte is not required to diffuse in an extra macroscopic dimension because the pores or "windows" in the PIM are micro- or nano-scale. The tortuous pores of the PIM are illustrated as being straight for simplicity. Features are not necessarily drawn to scale.

FIG. 2 illustrates a cross-section of a typical sensor structure 100 of the present invention. The sensor is formed from a plurality of components that are typically in the form of layers of various conductive and non-conductive constituents disposed on each other according to a method of the invention to produce a sensor structure. The components of the sensor are typically characterized herein as layers because, for example, it allows for a facile characterization of the sensor structure shown in FIG. 2. Artisans will understand however, that in certain embodiments of the invention, the sensor constituents are combined such that multiple constituents form one or more heterogenous layers. An illustrative embodiment of such a combination of constituents is shown in FIG. 10.

The embodiment shown in FIG. 2 includes a base layer 102 to support the sensor 100. The base layer 102 can be made of a material such as a metal and/or a ceramic and/or a polymeric substrate, which may be self-supporting or further supported by another material as is known in the art. Embodiments of the invention include a conductive layer 104 which is disposed on and/or combined with the base layer 102.

Typically the conductive layer 104 comprises one or more electrodes. An operating sensor 100 typically includes a plurality of electrodes such as a working electrode, a counter electrode and a reference electrode. Other embodiments may also include an electrode that performs multiple functions, for example one that functions as both as a reference and a counter electrode. Still other embodiments may utilize a separate reference element not formed on the sensor. Typically these electrodes are electrically isolated from each other, while situated in close proximity to one another.

As discussed in detail below, the base layer 102 and/or conductive layer 104 can be generated using many known techniques and materials. In certain embodiments of the invention, the electrical circuit of the sensor is defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating cover layer 106 such as a polymer coating is optionally disposed on portions of the sensor 100. Acceptable polymer coatings for use as the insulating protective cover layer 106 can include, but are not limited to, non-toxic biocompatible polymers such as silicone compounds, polyimides, biocompatible solder masks, epoxy acrylate copolymers, or the like. In the sensors of the present invention, one or more exposed regions or apertures 108 can be made through the cover layer 106 to open the conductive layer 104 to the external environment and to for example allow an analyte such as glucose to permeate the layers of the sensor and be sensed by the sensing elements. Apertures 108 can be formed by a number of techniques, including laser ablation, tape masking, chemical milling or etching or photolithographic development or the like. In certain embodiments of the invention, during manufacture, a secondary photoresist can also be applied to the protective layer 106 to define the regions of the protective layer to be removed to form the aperture(s) 108. The exposed electrodes and/or contact pads can also undergo secondary processing (e.g. through the apertures 108), such as additional plating processing, to prepare the surfaces and/or strengthen the conductive regions.

In the sensor configuration shown in FIG. 2, an analyte sensing layer 110 (which is typically a sensor chemistry layer, meaning that materials in this layer undergo a chemical reaction to produce a signal that can be sensed by the conductive layer) is disposed on one or more of the exposed electrodes of the conductive layer 104. Typically, the sensor chemistry layer 110 is an enzyme layer. Most typically, the sensor chemistry layer 110 comprises an enzyme capable of producing utilizing oxygen and/or hydrogen peroxide, for example the enzyme glucose oxidase. Optionally the enzyme in the sensor chemistry layer is combined with a second carrier protein such as human serum albumin, bovine serum albumin or the like. In an illustrative embodiment, an enzyme such as glucose oxidase in the sensor chemistry layer 110 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can by monitored by any one of a variety of sensor detector apparatuses such as a universal sensor amperometric biosensor detector or one of the other variety of similar devices known in the art such as glucose monitoring devices produced by Medtronic MiniMed.

The analyte sensing layer 110 can be applied over portions of the conductive layer or over the entire region of the conductive layer. Typically the analyte sensing layer 110 is disposed on the working electrode which can be the anode or the cathode. Optionally, the analyte sensing layer 110 is also disposed on a counter and/or reference electrode. While the analyte sensing layer 110 can be up to about 1000 microns (μm) in thickness, typically the analyte sensing layer is relatively thin as compared to those found in sensors previously described in the art, and is for example, typically less than 1, 0.5, 0.25 or 0.1 microns in thickness. As discussed in detail below, some methods for generating a thin analyte sensing layer 110 include spin coating processes, dip and dry processes, low shear spraying processes, ink-jet printing processes, silk screen processes and the like. Most typically the thin analyte sensing layer 110 is applied using a spin coating process.

Typically, the analyte sensing layer 110 is coated with one or more additional layers. Optionally, the one or more additional layers includes a protein layer 116 disposed upon the analyte sensing layer 110 as shown in FIG. 2B. Typically, the protein layer 116 comprises a protein such as albumin or the like. Typically, the protein layer 116 comprises human serum albumin. In some embodiments of the invention, an additional layer includes an analyte modulating layer 112 that is disposed above the analyte sensing layer 110 to regulate analyte contact with the analyte sensing layer 110. For example, the analyte modulating membrane layer 112 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, Nafion, polyester sulfonic acids (e.g. Kodak AQ), hydrogels or any other suitable hydrophilic membranes known to those skilled in the art.

Figure 2A:
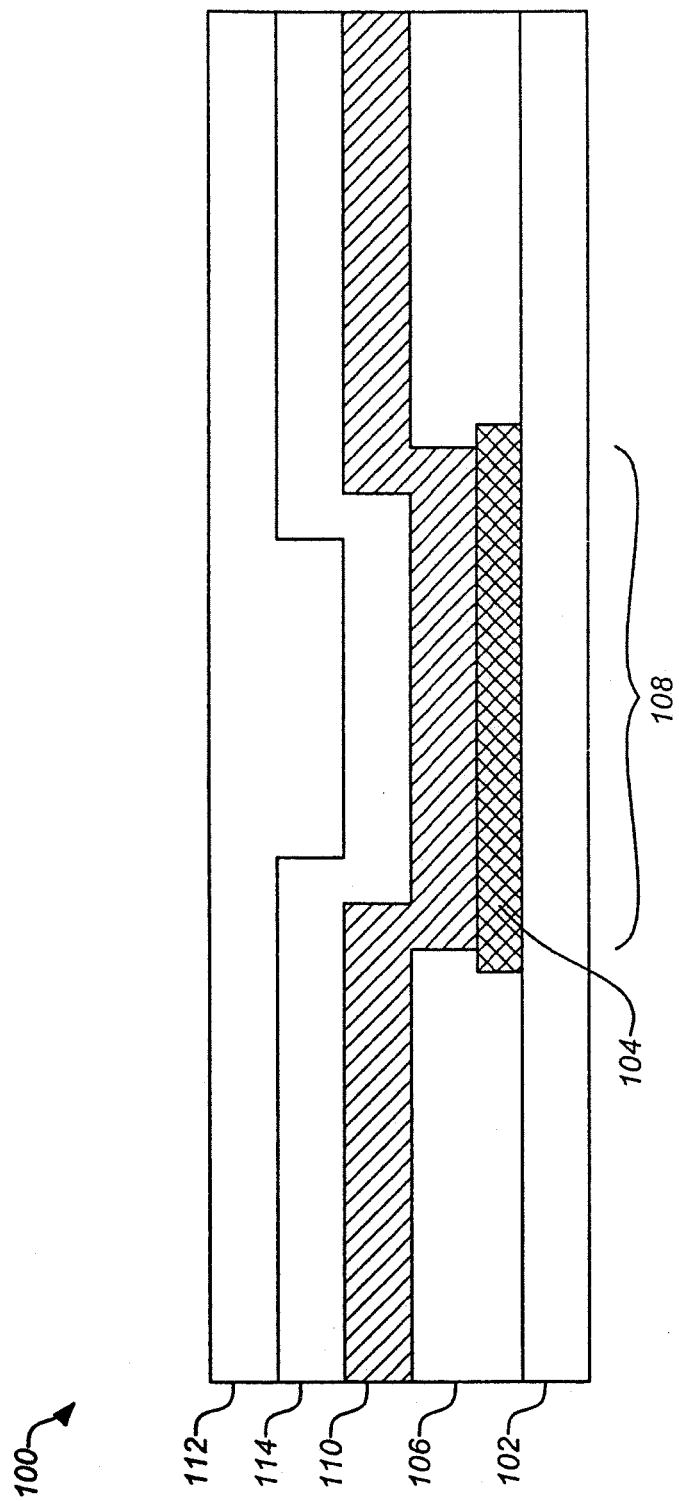
FIG. 2A shows an embodiment that does not include an optional protein layer.
Figure 2B:
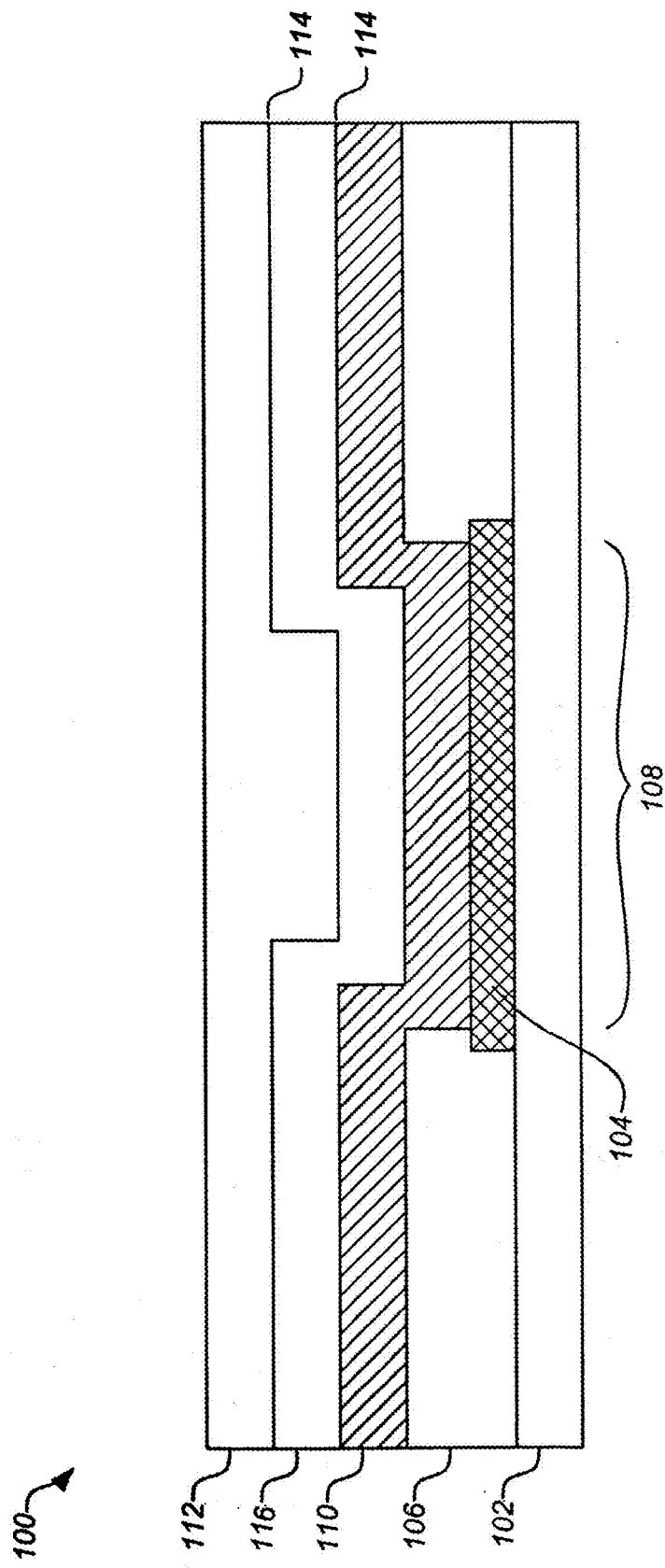
FIG. 2B shows an embodiment that includes an optional protein layer.

In typical embodiments of the invention, an adhesion promoter layer 114 is disposed between the analyte modulating layer 112 and the analyte sensing layer 110 as shown in FIG. 2A in order to facilitate their contact and/or adhesion. In another embodiment of the invention, an adhesion promoter layer 114 is disposed between the analyte modulating layer 112 and a protein layer 116 and/or an analyte sensing layer 110 as shown in FIG. 2B in order to facilitate their contact and/or adhesion. The adhesion promoter layer 114 can be made from any one of a wide variety of materials known in the art to facilitate the bonding between such layers. Typically, the adhesion promoter layer 114 comprises a silane compound. In alternative embodiments, protein or like molecules in the analyte sensing layer 110 can be sufficiently crosslinked or otherwise prepared to allow the analyte modulating membrane layer 112 to be disposed in direct contact with the analyte sensing layer 110 in the absence of an adhesion promoter layer 114.

C. Typical Analyte Sensor Constituents

The following disclosure provides examples of typical elements/constituents, one or more of which can be combined with the other constituents described herein (or alternatively other constituents known in the art) to form the sensors of the invention. While these elements can be described as discreet units (e.g. layers), those of skill in the art understand that sensor can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). An illustrative embodiment of such a combination of constituents is shown in FIG. 10.

Base Constituent

Sensors of the invention typically include a base constituent (see, e.g. element 102 in FIG. 2). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of a wide variety of materials having desirable qualities such as water impermeability and hermeticity. Some materials include metallic ceramic and polymeric substrates or the like. Optionally the base can comprise an electrode such as the porous electrode matrices disclosed herein.

The base constituent may be self-supporting or further supported by another material as is known in the art. In one embodiment of the sensor configuration shown in FIG. 2, the base constituent 102 comprises a ceramic. In an illustrative embodiment, the ceramic base comprises a composition that is predominantly $Al_2O_3$ (e.g. 96%). The use of alumina as an insulating base constituent for use with implantable devices is disclosed in U.S. Pat. Nos. 4,940,858, 4,678,868 and 6,472, 122 which are incorporated herein by reference. The base constituents of the invention can further include other elements known in the art, for example hermetical vias (see, e.g. WO 03/023388). Depending upon the specific sensor design, the base constituent can be relatively thick constituent (e.g. thicker than 25 microns). Alternatively, one can utilize a nonconductive ceramic, such as alumina, in thin constituents, e.g., less than about 25 microns.

Conductive Constituent

The electrochemical sensors of the invention typically include a conductive constituent disposed upon the base constituent that includes at least one electrode for contacting an analyte or its byproduct (e.g. oxygen and/or hydrogen peroxide) to be assayed (see, e.g. element 104 in FIG. 2). The term "conductive constituent" is used herein according to art accepted terminology and refers to electrically conductive sensor elements such as electrodes which are capable of measuring and a detectable signal and conducting this to a detection apparatus. An illustrative example of this is a conductive constituent that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 110 or the reaction product of this interaction (e.g. hydrogen peroxide). Illustrative examples of such elements include electrodes which are capable of producing a variable detectable signals in the presence of variable concentrations of molecules such as hydrogen peroxide or oxygen. Typically one of these electrodes in the conductive constituent is a working electrode, which can be made from non-corroding metal or carbon. A carbon working electrode may be vitreous or graphitic and can be made from a solid or a paste. A metallic working electrode may be made from platinum group metals, including palladium or gold, or a non-corroding metallically conducting oxide, such as ruthenium dioxide. Alternatively the electrode may comprise a silver/silver chloride electrode composition. The working electrode may be a wire or a thin conducting film applied to a substrate, for example, by coating or printing.

As noted herein, the conductive constituent can comprise one or more of the porous electrode matrices disclosed herein. Typically, only a portion of the surface of the metallic or carbon conductor is in electrolytic contact with the analyte-containing solution. This portion is called the working surface of the electrode. The remaining surface of the electrode is typically isolated from the solution by an electrically insulating cover constituent 106. Examples of useful materials for generating this protective cover constituent 106 include polymers such as polyimides, polytetrafluoroethylene, polyhexafluoropropylene and silicones such as polysiloxanes.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/or counter/reference electrodes. One embodiment of the sensor of the present invention has two, three or four or more working electrodes. These working electrodes in he sensor may be integrally connected or they may be kept separate.

Typically, for in vivo use the analyte sensors of the present invention are implanted subcutaneously in the skin of a mammal for direct contact with the body fluids of the mammal, such as blood. Alternatively the sensors can be implanted into other regions within the body of a mammal such as in the Intraperotineal space. When multiple working electrodes are used, they may be implanted together or at different positions in the body. The counter, reference, and/or counter/reference electrodes may also be implanted either proximate to the working electrode(s) or at other positions within the body of the mammal.

Interference Rejection Constituent

The electrochemical sensors of the invention optionally include an interference rejection constituent disposed between the surface of the electrode and the environment to be assayed. In particular, certain sensor embodiments rely on the oxidation and/or reduction of hydrogen peroxide generated by enzymatic reactions on the surface of a working electrode at a constant potential applied. Because amperometric detection based on direct oxidation of hydrogen peroxide requires a relatively high oxidation potential, sensors employing this detection scheme may suffer interference from oxidizable species that are present in biological fluids such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. Examples of interference rejection constituents include one or more layers or coatings of compounds such as hydrophilic polyurethanes, cellulose acetate (including cellulose acetate incorporating agents such as poly(ethylene glycol), polyethersulfones, polytetra-fluoroethylenes, the perfluoronated ionomer Naflon™, polyphenylenediamine, epoxy and the like. Illustrative discussions of such interference rejection constituents are found for example in Ward et al., Biosensors and Bioelectronics 17 (2002) 181-189 and Choi et al., Analytical Chimica Acta 461 (2002) 251-260 which are incorporated herein by reference.

Analyte Sensing Constituent

The electrochemical sensors of the invention include a analyte sensing constituent disposed on the electrodes of the sensor (see, e.g. element 110 in FIG. 2). The term "analyte sensing constituent" is used herein according to art accepted terminology and refers to a constituent comprising a material that is capable of recognizing or reacting with an analyte whose presence is to be detected by the analyte sensor apparatus. Typically this material in the analyte sensing constituent produces a detectable signal after interacting with the analyte to be sensed, typically via the electrodes of the conductive constituent. In this regard the analyte sensing constituent and the electrodes of the conductive constituent work in combination to produce the electrical signal that is read by an apparatus associated with the analyte sensor. Typically, the analyte sensing constituent comprises an enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively the analyte sensing constituent may coat different electrodes to different degrees, with for example the coated surface of the working electrode being larger than the coated surface of the counter and/or reference electrode.

Typical sensor embodiments of this element of the invention utilize an enzyme (e.g. glucose oxidase) that has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA mixture. A typical embodiments of a analyte sensing constituent having GOx, the GOx reacts with glucose present in the sensing environment (e.g. the body of a mammal) and generates hydrogen peroxide according the reaction shown in FIG. 1, wherein the hydrogen peroxide so generated is anodically detected at the working electrode in the conductive constituent. As discussed for example in U.S. patent application Ser. No. 10/273,767 (incorporated herein by reference) extremely thin sensor chemistry constituents are typical and can be applied to the surface of the electrode matrix by processes known in the art such as spin coating. In an illustrative embodiment, a glucose oxidase/albumin is prepared in a physiological solution (e.g., phosphate buffered saline at neutral pH) with the albumin being present in an range of about 0.5%-10% by weight. Optionally the stabilized glucose oxidase constituent that is formed on the analyte sensing constituent is very thin as compared to those previously described in the art, for example less than 2, 1, 0.5, 0.25 or 0.1 microns in thickness. One illustrative embodiment of the invention utilizes a stabilized glucose oxidase constituent for coating the surface of an electrode wherein the glucose oxidase is mixed with a carrier protein in a fixed ratio within the constituent, and the glucose oxidase and the carrier protein are distributed in a substantially uniform manner throughout the constituent. Typically the constituent is less than 2 microns in thickness. For purposes of clarity, it should be noted that this may not apply to certain embodiments of the invention where the analyte sensing constituent is disposed on a porous electrode. For example, in a porous electrode that is 100 microns thick, with 3 micron size pores that are filled with GOx an enzyme layer can be greater 2 microns.

Surprisingly, sensors having these extremely thin analyte sensing constituents have material properties that exceed those of sensors having thicker coatings including enhanced longevity, linearity, regularity as well as improved signal to noise ratios. While not being bound by a specific scientific theory, it is believed that sensors having extremely thin analyte sensing constituents have surprisingly enhanced characteristics as compared to those of thicker constituents because in thicker enzyme constituents only a fraction of the reactive enzyme within the constituent is able to access the analyte to be sensed. In sensors utilizing glucose oxidase, the thick coatings produced by electrodeposition may hinder the ability of hydrogen peroxide generated at the reactive interface of a thick enzyme constituent to contact the sensor surface and thereby generate a signal.

As noted above, the enzyme and the second protein are typically treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture. The addition of a cross-linking reagent to the protein mixture creates a protein paste. The concentration of the cross-linking reagent to be added may vary according to the concentration of the protein mixture. While glutaraldehyde is an illustrative crosslinking reagent, other cross-linking reagents may also be used or may be used in place of glutaraldehyde, including, but not limited to, an amine reactive, homofunctional, cross-linking reagent such as Disuccinimidyl Suberate (DSS). Another example is 1-Ethyl-3(3-Dimethylaminopropyl)Carbodiimide (EDC), which is a zero-length cross-linker. EDC forms an amide bond between carboxylic acid and amine groups. Other suitable cross-linkers also may be used, as will be evident to those skilled in the art.

The GOx and/or carrier protein concentration may vary for different embodiments of the invention. For example, the GOx concentration may be within the range of approximately 50 mg/ml (approximately 10,000 U/ml) to approximately 700 mg/ml (approximately 150,000 U/ml). Typically the GOx concentration is about 115 mg/ml (approximately 22,000 U/ml). In such embodiments, the HSA concentration may vary between about 0.5%-30% (w/v), depending on the GOx concentration. Typically the HSA concentration is about 1-10% w/v, and most typically is about 5% w/v. In alternative embodiments of the invention, collagen or BSA or other structural proteins used in these contexts can be used instead of or in addition to HSA. Although GOx is discussed as an illustrative enzyme in the analyte sensing constituent, other proteins and/or enzymes may also be used or may be used in place of GOx, including, but not limited to glucose dehydrogenase or hexokinase, hexose oxidase, lactate oxidase, and the like. Other proteins and/or enzymes may also be used, as will be evident to those skilled in the art. Moreover, although HSA is employed in the example embodiment, other structural proteins, such as BSA, collagens or the like, could be used instead of or in addition to HSA.

For embodiments employing enzymes other than GOx, concentrations other than those discussed herein may be utilized. For example, depending on the enzyme employed, concentrations ranging from approximately 10% weight per weight to 70% weight per weight may be suitable. The concentration may be varied not only depending on the particular enzyme being employed, but also depending on the desired properties of the resulting protein matrix. For example, a certain concentration may be utilized if the protein matrix is to be used in a diagnostic capacity while a different concentration may be utilized if certain structural properties are desired. Those skilled in the art will understand that the concentration utilized may be varied through experimentation to determine which concentration (and of which enzyme or protein) may yield the desired result.

As noted above, in some embodiments of the invention, the analyte sensing constituent includes a composition (e.g. glucose oxidase) capable of producing a signal (e.g. a change in oxygen and/or hydrogen peroxide concentrations) that can be sensed by the electrically conductive elements (e.g. electrodes which sense changes in oxygen and/or hydrogen peroxide concentrations). However, other useful analyte sensing constituents can be formed from any composition that is capable of producing a detectable signal that can be sensed by the electrically conductive elements after interacting with a target analyte whose presence is to be detected. In some embodiments, the composition comprises an enzyme that modulates hydrogen peroxide concentrations upon reaction with an analyte to be sensed. Alternatively, the composition comprises an enzyme that modulates oxygen concentrations upon reaction with an analyte to be sensed. In this context, a wide variety of enzymes that either use or produce hydrogen peroxide and/or oxygen in a reaction with a physiological analyte are known in the art and these enzymes can be readily incorporated into the analyte sensing constituent composition. A variety of other enzymes known in the art can produce and/or utilize compounds whose modulation can be detected by electrically conductive elements such as the electrodes that are incorporated into the sensor designs described herein. Such enzymes include for example, enzymes specifically described in Table 1, pages 15-29 and/or Table 18, pages 111-112 of Protein Immobilization: Fundamentals and Applications (Bioprocess Technology, Vol 14) by Richard F. Taylor (Editor) Publisher: Marcel Dekker; (Jan. 7, 1991) the entire contents of which are incorporated herein by reference.

Other useful analyte sensing constituents can be formed to include antibodies whose interaction with a target analyte is capable of producing a detectable signal that can be sensed by the electrically conductive elements after interacting with the target analyte whose presence is to be detected. For example U.S. Pat. No. 5,427,912 (which is incorporated herein by reference) describes an antibody-based apparatus for electrochemically determining the concentration of an analyte in a sample. In this device, a mixture is formed which includes the sample to be tested, an enzyme-acceptor polypeptide, an enzyme-donor polypeptide linked to an analyte analog (enzyme-donor polypeptide conjugate), a labeled substrate, and an antibody specific for the analyte to be measured. The analyte and the enzyme-donor polypeptide conjugate competitively bind to the antibody. When the enzyme-donor polypeptide conjugate is not bound to antibody, it will spontaneously combine with the enzyme acceptor polypeptide to form an active enzyme complex. The active enzyme then hydrolyzes the labeled substrate, resulting in the generation of an electroactive label, which can then be oxidized at the surface of an electrode. A current resulting from the oxidation of the electroactive compound can be measured and correlated to the concentration of the analyte in the sample. U.S. Pat. No. 5,149,630 (which is incorporated herein by reference) describes an electrochemical specific binding assay of a ligand (e.g., antigen, hapten or antibody) wherein at least one of the components is enzyme-labelled, and which includes the step of determining the extent to which the transfer of electrons between the enzyme substrate and an electrode, associated with the substrate reaction, is perturbed by complex formation or by displacement of any ligand complex relative to unbound enzyme-labelled component. The electron transfer is aided by electron-transfer mediators which can accept electrons from the enzyme and donate them to the electrode or vice versa (e.g. ferrocene) or by electron-transfer promoters which retain the enzyme in close proximity with the electrode without themselves taking up a formal charge. U.S. Pat. No. 5,147,781 (which is incorporated herein by reference) describes an assay for the determination of the enzyme lactate dehydrogenase-5 (LDH5) and to a biosensor for such quantitative determination. The assay is based on the interaction of this enzyme with the substrate lactic acid and nicotine-amine adenine dinucleotide (NAD) to yield pyruvic acid and the reduction product of NAD. Anti-LDH5 antibody is bound to a suitable glassy carbon electrode, this is contacted with the substrate containing LDH5, rinsed, inserted into a NAD solution, connected to an amperometric system, lactic acid is added and the current changes are measured, which are indicative of the quantity of LDH-5. U.S. Pat. No. 6,410,251 (which is incorporated herein by reference) describes an apparatus and method for detecting or assaying one constituting member in a specific binding pair, for example, the antigen in an antigen/antibody pair, by utilizing specific binding such as binding between an antigen and an antibody, together with redox reaction for detecting a label, wherein an oxygen micro-electrode with a sensing surface area is used. In addition, U.S. Pat. No. 4,402,819 (which is incorporated herein by reference) describes an antibody-selective potentiometric electrode for the quantitative determination of antibodies (as the analyte) in dilute liquid serum samples employing an insoluble membrane incorporating an antigen having bonded thereto an ion carrier effecting the permeability of preselected cations therein, which permeability is a function of specific antibody concentrations in analysis, and the corresponding method of analysis. For related disclosures, see also U.S. Pat. Nos. 6,703,210, 5,981,203, 5,705,399 and 4,894,253, the contents of which are incorporated herein by reference.

In addition to enzymes and antibodies, other exemplary materials for use in the analyte sensing constituents of the sensors disclosed herein include polymers that bind specific types of cells or cell components (e.g. polypeptides, carbohydrates and the like); single-strand DNA; antigens and the like. The detectable signal can be, for example, an optically detectable change, such as a color change or a visible accumulation of the desired analyte (e.g., cells). Sensing elements can also be formed from materials that are essentially nonreactive (i.e., controls). The foregoing alternative sensor elements are beneficially included, for example, in sensors for use in cell-sorting assays and assays for the presence of pathogenic organisms, such as viruses (HIV, hepatitis-C, etc.), bacteria, protozoa and the like.

Also contemplated are analyte sensors that measure an analyte that is present in the external environment and that can in itself produce a measurable change in current at an electrode. In sensors measuring such analytes, the analyte sensing constituent can be optional.

Protein Constituent

The electrochemical sensors of the invention optionally include a protein constituent disposed between the analyte sensing constituent and the analyte modulating constituent (see, e.g. element 116 in FIG. 2). The term "protein constituent" is used herein according to art accepted terminology and refers to constituent containing a carrier protein or the like that is selected for compatibility with the analyte sensing constituent and or the analyte modulating constituent. In typical embodiments, the protein constituent comprises an albumin such as human serum albumin. The HSA concentration may vary between about 0.5%-30% (w/v). Typically the HSA concentration is about 1-10% w/v, and most typicall is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g. element 114 in FIG. 2). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as γ-aminopropyltrimethoxysilane.

The use of silane coupling reagents, especially those of the formula $R'Si(OR)_3$ in which R' is typically an aliphatic group with a terminal amine and R is a lower alkyl group, to promote adhesion is known in the art (see, e.g. U.S. Pat. No. 5,212,050 which is incorporated herein by reference). For example, chemically modified electrodes in which a silane such as γ-aminopropyltriethoxysilane and glutaraldehyde were used in a step-wise process to attach and to co-crosslink bovine serum albumin (BSA) and glucose oxidase (GOx) to the electrode surface are well known in the art (see, e.g. Yao, T. Analytica Chim. Acta 1983, 148, 27-33).

In certain embodiments of the invention, the adhesion promoting constituent further comprises one or more compounds that can also be present in an adjacent constituent such as the polydimethyl siloxane (PDMS) compounds that serves to limit the diffusion of analytes such as glucose through the analyte modulating constituent. In illustrative embodiments the formulation comprises 0.5-20% PDMS, typically 5-15% PDMS, and most typically 10% PDMS. In certain embodiments of the invention, the adhesion promoting constituent includes an agent selected for its ability to cros slink a siloxane moiety present in a proximal constituent such as the analyte modulating constituent. In closely related embodiments of the invention, the adhesion promoting constituent includes an agent selected for its ability to crosslink an amine or carboxyl moiety of a protein present in a proximal constituent such a the analyte sensing constituent and/or the protein constituent.

Analyte Modulating Constitutent

The electrochemical sensors of the invention include an analyte modulating constituent disposed on the sensor (see, e.g. element 112 in FIG. 2). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte limiting membrane which operates to prevent or restrict the diffusion of one or more analytes, such as glucose, through the constituents. In other embodiments of the invention, the analyte modulating constituent operates to facilitate the diffusion of one or more analytes, through the constituents. Optionally such analyte modulating constituents can be formed to prevent or restrict the diffusion of one type of molecule through the constituent (e.g. glucose), while at the same time allowing or even facilitating the diffusion of other types of molecules through the constituent (e.g. $O_2$).

With respect to glucose sensors, in known enzyme electrodes, glucose and oxygen from blood, as well as some interferants, such as ascorbic acid and uric acid diffuse through a primary membrane of the sensor. As the glucose, oxygen and interferants reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The sensor membrane assembly serves several functions, including selectively allowing the passage of glucose therethrough. In this context, an illustrative analyte modulating constituent is a semi-permeable membrane which permits passage of water, oxygen and at least one selective analyte and which has the ability to absorb water, the membrane having a water soluble, hydrophilic polymer.

A variety of illustrative analyte modulating compositions are known in the art and are described for example in U.S. Pat. Nos. 6,319,540, 5,882,494, 5,786,439 5,777,060, 5,771,868 and 5,391,250, the disclosures of each being incorporated herein by reference. The hydrogels described therein are particularly useful with a variety of implantable devices for which it is advantageous to provide a surrounding water constituent. In some embodiments of the invention, the analyte modulating composition includes PDMS. In certain embodiments of the invention, the analyte modulating constituent includes an agent selected for its ability to crosslink a siloxane moiety present in a proximal constituent. In closely related embodiments of the invention, the adhesion promoting constituent includes an agent selected for its ability to crosslink an amine or carboxyl moiety of a protein present in a proximal constituent.

As discussed in the sections below, one embodiment of the invention is an analyte modulating membrane for use with an analyte sensor (e.g. a glucose limiting membrane) which made from a material such as poly(dimethyl siloxane) and which optionally contains a plurality of pores disposed within it so as to facilitate the sensing of the analyte. Optionally one or more of the plurality of pores in the membrane is filled with a hydrophilic composition.

Cover Constitutent

The electrochemical sensors of the invention include one or more cover constituents which are typically electrically insulating protective constituents (see, e.g. element 106 in FIG. 2). Typically, such cover constituents are disposed on at least a portion of the analyte modulating constituent. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photo-imageable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

Various illustrative embodiments of the invention and their characteristics are discussed in detail in the following sections.

D. Illustrative Embodiments of Analyte Sensor Apparatus and Associated Characteristics The analyte sensor apparatus disclosed herein has a number of embodiments. A general embodiment of the invention is an analyte sensor apparatus for implantation within a mammal. While the analyte sensors are typically designed to be implantable within the body of a mammal, the sensor are not limited to any particular environment can instead be used in a wide variety of contexts, for example for the analysis of most liquid samples including biological fluids such as whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

As noted above, the sensor embodiments disclosed herein can be used to sense analytes of interest in one or more physiological environments. In certain embodiments for example, the sensor can be in direct contact with interstitial fluids as typically occurs with subcutaneous sensors. The sensors of the present invention may also be part of a skin surface system where interstitial glucose is extracted through the skin and brought into contact with the sensor (see, e.g. U.S. Pat. Nos. 6,155,992 and 6,706,159 which are incorporated herein by reference). In other embodiments, the sensor can be in contact with blood as typically occurs for example with intravenous sensors. The sensor embodiments of the invention further include those adapted for use in a variety of contexts. In certain embodiments for example, the sensor can be designed for use in mobile contexts, such as those employed by ambulatory users. Alternatively, the sensor can be designed for use in stationary contexts such as those adapted for use in clinical settings. Such sensor embodiments include for example those used to monitor one or more analytes present in one or more physiological environments in a hospitalized patient.

Sensors of the invention can also be incorporated in to a wide variety of medical systems known in the art. Sensors of the invention can be used for example in a closed loop infusion systems designed to control the rate that medication is infused into the body of a user. Such a closed loop infusion system can include a sensor and an associated meter which generates an input to a controller which in turn operates a delivery system (e.g. one that calculates a dose to be delivered by a medication infusion pump). In such contexts, the meter associated with the sensor may also transmit commands to, and be used to remotely control, the delivery system. Typically, the sensor is a subcutaneous sensor in contact with interstitial fluid to monitor the glucose concentration in the body of the user, and the liquid infused by the delivery system into the body of the user includes insulin. Illustrative systems are disclosed for example in U.S. Pat. Nos. 6,558,351 and 6,551,276; PCT Application Nos. US99/21703 and US99/22993; as well as WO 2004/008956 and WO 2004/009161, all of which are incorporated herein by reference.

Certain embodiments of the invention measure peroxide and have the advantageous characteristic of being suited for implantation in a variety of sites in the mammal including regions of subcutaneous implantation and intravenous implantation as well as implantation into a variety of non-vascular regions. A peroxide sensor design that allows implantation into non-vascular regions has advantages over certain sensor apparatus designs that measure oxygen due to the problems with oxygen noise that can occur in oxygen sensors implanted into non-vascular regions. For example in such implanted oxygen sensor apparatus designs, oxygen noise at the reference sensor can compromise the signal to noise ratio which consequently perturbs their ability to obtain stable glucose readings in this environment. The peroxide sensors of the invention therefore overcome the difficulties observed with such oxygen sensors in non-vascular regions.

Certain peroxide sensor embodiments of the invention further include advantageous long term or "permanent" sensors which are suitable for implantation in a mammal for a time period of greater than 30 days. In particular, as is known in the art (see, e.g. ISO 10993, Biological Evaluation of Medical Devices) medical devices such as the sensors described herein can be categorized into three groups based on implant duration: (1) "Limited" (<24 hours), (2) "Prolonged" (24 hours-30 days), and (3) "Permanent" (>30 days). In some embodiments of the invention, the design of the peroxide sensor of the invention allows for a "Permanent" implantation according to this categorization, i.e. >30 days. In related embodiments of the invention, the highly stable design of the peroxide sensor of the invention allows for an implanted sensor to continue to function in this regard for 2, 3, 4, 5, 6 or 12 or more months.

In general, the analyte sensor apparatus structure comprises a base layer and a conductive layer disposed upon the base layer (e.g. a porous matrix) and functions as one or more electrodes. For example, the conductive layer can include a working electrode, a reference electrode and/or a counter electrode. These electrodes can be spaced in proximity, or alternatively are spaced distally according to the specific design. The sensor apparatus design is such that certain electrodes (e.g. the working electrode) can be exposed to the solution containing the analyte to be sensed (e.g. via an aperture) in the sensor apparatus. The sensor apparatus design is such that certain electrodes (e.g. the reference electrode) are not exposed to the solution containing the analyte to be sensed in the sensor apparatus.

One embodiment of the invention is a composition for use in biosensors. Such compositions are typically designed to implantable within a mammal and comprise a porous matrix having a surface coated with an immobilized enzyme, for example glucose oxidase, glucose dehydrogenase, lactate oxidase, hexokinase or lactate dehydrogenase. Typically the porous matrix coated with an immobilized enzyme is capable of acting as an electrode in an electrochemical sensor. Optionally the electrode in the electrochemical sensor consumes hydrogen peroxide.

The porous matrices used in various embodiments of the biosensors of the invention can be generated from a variety of materials and can be adapted to a variety of compositional configurations. In some embodiments of the invention, the porous matrix comprises a ceramic material and/or a metal and/or a macroporous polymer. Optionally the porous matrix comprises a lattice of particles. Typically the particles are spherical. In typical embodiments of the invention, porous matrix has a surface area that is at least 2, 4, 6, 8, 10, 12, 14, 16 or 18 times the surface area of a non-porous matrix of same dimensions. In certain embodiments of the invention, the porous matrix is at least 1, 10, 100, or 1000 microns thick. In certain embodiments of the invention, the porosity range of the porous matrix is optionally about 5-99.9% and typically is about 40-99%. The porosity of these matrices can be measured by one of the protocols typically used in the art such as mercury or gas porosimetry, size-exclusion chromatography using marker molecules of various sizes and molecular weights (e.g. acetone, various globular proteins of a defined size, blue dextran), and cyclic voltammetry.

A related embodiment of the invention is an analyte sensor apparatus for implantation within a mammal which includes a porous matrix having a surface coated with an immobilized enzyme, for example glucose oxidase. In one embodiment of this sensor design, the porous matrix comprises a working electrode; and the immobilized enzyme is disposed within an analyte sensing layer disposed on the working electrode, such that the analyte sensing layer detectably alters the electrical current at the working electrode in the conductive layer in the presence of an analyte. Typically the sensor further comprises an analyte modulating layer disposed on the analyte sensing layer, wherein the analyte modulating layer modulates the diffusion of the analyte therethrough. Typically, the sensor further comprises an adhesion promoting layer disposed on the analyte sensing layer, wherein the adhesion promoting layer promotes the adhesion between the analyte sensing layer and an analyte modulating layer disposed on the analyte sensing layer. Optionally the sensor further comprises a protein layer disposed between the analyte sensing layer and the analyte modulating layer. Typically the sensor further comprises a cover layer disposed on at least a portion of the analyte modulating layer, wherein the cover layer further includes an aperture that exposes at least a portion of the analyte modulating layer to a solution comprising the analyte to be sensed.

A related embodiment of the invention is a method of making a sensor apparatus for implantation within a mammal comprising the steps of providing a layer comprising a porous matrix, forming an analyte sensing layer on the porous matrix, wherein the analyte sensing layer includes an enzyme such as glucose oxidase that can alter the electrical current at the surface of the porous matrix in the presence of an analyte so that the porous matrix having the analyte sensing layer formed thereon functions as an electrode. Such methods further include the steps of optionally forming a protein layer on the analyte sensing layer, forming an adhesion promoting layer on the analyte sensing layer or the optional protein layer, forming an analyte modulating layer disposed on the adhesion promoting layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer.

Another embodiment of the invention is a method of sensing an analyte within the body of a mammal, the method comprising implanting an analyte sensor in to the mammal, the analyte sensor comprising a porous matrix having an analyte sensing layer disposed thereon, wherein the analyte sensing layer detectably alters the electrical current at the surface of the porous matrix in the presence of an analyte so that the porous matrix having the analyte sensing layer formed thereon functions as an electrode, an optional protein layer disposed on the analyte sensing layer, an adhesion promoting layer disposed on the analyte sensing layer or the optional protein layer, wherein the adhesion promoting layer promotes the adhesion between the analyte sensing layer and an analyte modulating layer disposed on the analyte sensing layer, and an analyte modulating layer disposed on the analyte sensing layer, wherein the analyte modulating layer modulates the diffusion of the analyte therethrough, a cover layer disposed on at least a portion of the analyte modulating layer, wherein the cover layer further includes an aperture over at least a portion of the analyte modulating layer; and sensing an alteration in current at the electrical current and correlating the alteration in current with the presence of the analyte, so that the analyte is sensed.

Yet another embodiment of the invention is a method of immobilizing a protein on a rigid macroporous polymer comprising the steps of: combining the protein with the rigid macroporous polymer having functional moieties capable of crosslinking to a protein; and then adding a crosslinking agent capable of immobilizing the protein on the rigid macroporous polymer by crosslinking the functional moieties of the protein with the functional moieties of the rigid macroporous polymer so that the protein is immobilized on the rigid macroporous polymer. In certain embodiments of the invention, the rigid macroporous polymer having functional moieties capable of crosslinking to a protein is made by combining a rigid macroporous polymer having reactive epoxide moieties with a nucleophilic compound so that a rigid macroporous polymer having functional moieties capable of crosslinking to a protein is made.

Yet another embodiment of the invention is a method of immobilizing a protein on a rigid macroporous polymer comprising combining a protein having a sulfhydryl, amine, carboxyl or hydroxyl moiety with a rigid macroporous polymer having reactive epoxide moieties under reaction conditions that allow a nucleophilic reaction to occur between the sulfhydryl, amine, carboxyl or hydroxyl moieties on the protein and the epoxide moieties on the rigid macroporous polymer so that the protein is immobilized on the rigid macroporous polymer. In certain embodiments of this method, at least one nucleophilic moiety on the protein is blocked prior to combining the protein with the rigid macroporous polymer. Analyte sensors of the invention typically incorporate the porous matrices disclosed herein. Typically, the analyte sensor apparatus includes an analyte sensing layer disposed on a conductive layer of the sensor, typically covering a portion or all of the working electrode. This analyte sensing layer detectably alters the electrical current at the working electrode in the conductive layer in the presence of an analyte to be sensed. As disclosed herein, this analyte sensing layer typically includes an enzyme or antibody molecule or the like that reacts with the analyte of interest in a manner that changes the concentrations of a molecule that can modulate the current at the working electrode (see e.g. oxygen and/or hydrogen peroxide as shown in the reaction scheme of FIG. 1). Illustrative analyte sensing layers comprise an enzyme such as glucose oxidase (e.g. for use in glucose sensors) or lactate oxidase (e.g. for use in lactate sensors). In some embodiments of the invention, the analyte sensing layer is disposed upon a porous metallic and/or ceramic and/or polymeric matrix with this combination of elements functioning as an electrode in the sensor.

Typically, the analyte sensing layer further comprises a carrier protein in a substantially fixed ratio with the analyte sensing compound (e.g. the enzyme) and the analyte sensing compound and the carrier protein are distributed in a substantially uniform manner throughout the analyte sensing layer. Typically the analyte sensing layer is very thin for example less than 1, 0.5, 0.25 or 0.1 microns in thickness. While not being bound by a specific scientific theory, it is believed that sensors having such thin analyte sensing layers have surprisingly enhanced characteristics as compared to the thicker layers that are typically generated by electrodeposition because electrodeposition produces 3-5 micron thick enzyme layers in which only a fraction of the reactive enzyme within the coating layer is able to access the analyte to be sensed. Such thicker glucose oxidase pellets that are produced by electrodeposition protocols are further observed to have a poor mechanical stability (e.g. a tendency to crack) and further take a longer time to prepare for actual use, typically taking weeks of testing before it is ready for implantation. As these problems are not observed with the thin layered enzyme coatings described herein, these thin coatings are typical embodiments of the invention.

In sensors utilizing glucose oxidase for example, the thick coatings produced by electrodeposition may hinder the ability of hydrogen peroxide generated at the reactive interface of the 3-5 micron thick enzyme layer to contact the sensor surface and thereby generate a signal. In addition, hydrogen peroxide that is unable to reach a sensor surface due to such thick coatings can diffuse away from the sensor into the environment in which the sensor is placed, thereby decreasing the sensitivity and/or biocompatibility of such sensors. Moreover, while not being bound by a specific scientific theory, it is believed that sensors having such thin analyte sensing layers have unexpectedly advantageous properties that result from the fact that processes such as spin coating, or the like, allow for a precise control over the enzyme coating's ratio of glucose oxidase to albumin (which is used as a carrier protein to stabilize the glucose oxidase in the enzyme layer). Specifically, because glucose oxidase and albumin have different isoelectric points, electrodeposition processes may result in a surface coating in which an optimally determined ratio of enzyme to carrier protein is detrimentally altered in the electrodeposition process and further wherein the glucose oxidase and the carrier protein are not distributed in a substantially uniform manner throughout the disposed enzyme layer. In addition, sensors having such thin analyte sensing layers have unexpectedly faster response times. While not being bound by a specific scientific theory, it is believed that these surprising and advantageous properties result from the fact that thin enzyme layers allow a better access to the working electrode surface and may allow a greater proportion of the molecules that modulate current at the electrode to access the electrode surface. In this context, in certain sensor embodiments of the invention, an alteration in current in response to exposure to the analyte present in the body of the mammal can be detected via an amperometer within 15, 10, 5 or 2 minutes of the analyte contacting the analyte sensor.

Optionally, the analyte sensing layer has a protein layer disposed thereon and which it typically between this analyte sensing layer and the analyte modulating layer. A protein within the protein layer is an albumin selected from the group consisting of bovine serum albumin and human serum albumin. Typically this protein is crosslinked. Without being bound by a specific scientific theory, it is believed that this separate protein layer enhances sensor function provides surprising functional benefits by acting as a sort of capacitor that diminishes sensor noise (e.g. spurious background signals). For example, in the sensors of the invention, some amount of moisture may form under the analyte modulating membrane layer of the sensor, the layer which regulates the amount of analyte that can contact the enzyme of the analyte sensing layer. This moisture may create a compressible layer that shifts within the sensor as a patient using the sensor moves. Such shifting of layers within the sensor may alter the way that an analyte such as glucose moves through the analyte sensing layers in a manner that is independent of actual physiological analyte concentrations, thereby generating noise. In this context, the protein layer may act as a capacitor by protecting an enzyme such as GOx from contacting the moisture layer. This protein layer may confer a number of additional advantages such as promoting the adhesion between the analyte sensing layer and the analyte modulating membrane layer. Alternatively, the presence of this layer may result in a greater diffusion path for molecules such as hydrogen peroxide, thereby localizing it to the electrode sensing element and contributing to an enhanced sensor sensitivity.

Typically, the analyte sensing layer and/or the protein layer disposed on the analyte sensing layer has an adhesion promoting layer disposed thereon. Such adhesion promoting layers promote the adhesion between the analyte sensing layer and a proximal layer, typically an analyte modulating layer. This adhesion promoting layer typically comprises a silane compound such as γ-aminopropyltrimethoxysilane which is selected for its ability to promote optimized adhesion between the various sensor layers and functions to stabilize the sensor. Interestingly sensors having such a silane containing adhesion promoting layers exhibit unexpected properties including an enhanced overall stability. In addition, silane containing adhesion promoting layers provide a number of advantageous characteristics in addition to an ability to enhancing sensor stability and can for example play a beneficial role in interference rejection as well as in controlling the mass transfer of one or more desired analytes.

In certain embodiments of the invention, the adhesion promoting layer further comprises one or more compounds that can also be present in an adjacent layer such as the polydimethyl siloxane (PDMS) compounds that serves to limit the diffusion of analytes such as glucose through the analyte modulating layer. The addition of PDMS to the AP layer for example can be advantageous in contexts where it diminishes the possibility of holes or gaps occurring in the AP layer as the sensor is manufactured.

Typically the adhesion promoting layer has an analyte modulating layer disposed thereon which functions to modulate the diffusion of analytes therethrough. In one embodiment, the analyte modulating layer includes compositions (e.g. polymers and the like) which serves to enhance the diffusion of analytes (e.g. oxygen) through the sensor layers and consequently function to enrich analyte concentrations in the analyte sensing layer. Alternatively, the analyte modulating layer includes compositions which serve to limit the diffusion of analytes (e.g. glucose) through the sensor layers and consequently function to limit analyte concentrations in the analyte sensing layer. An illustrative example of this is a hydrophilic glucose limiting membrane (i.e. functions to limit the diffusion of glucose therethrough) comprising a polymer such as polydimethyl siloxane or the like. As discussed in the sections below, an illustrative embodiment of the invention is a sensor which incorporates an analyte modulating membrane (e.g. a glucose limiting membrane) which made from a material such as poly(dimethyl siloxane) and which optionally contains a plurality of pores disposed within it so as to facilitate the sensing of the analyte. Optionally one or more of the plurality of pores in the membrane is filled with a hydrophilic composition Typically the analyte modulating layer further comprises one or more cover layers which are typically electrically insulating protective layers a cover layer disposed on at least a portion of the sensor apparatus (e.g. covering the analyte modulating layer). Acceptable polymer coatings for use as the insulating protective cover layer can include, but are not limited to, non-toxic biocompatible polymers such as silicone compounds, polyimides, biocompatible solder masks, epoxy acrylate copolymers, or the like. An illustrative cover layer comprises spun on silicone. Typically the cover layer further includes an aperture that exposes at least a portion of a sensor layer (e.g. analyte modulating layer) to a solution comprising the analyte to be sensed.

The analyte sensors described herein can be polarized cathodically to detect for example, changes in current at the working cathode that result from the changes in oxygen concentration proximal to the working cathode that occur as glucose interacts with glucose oxidase as shown in FIG. 1. Alternatively, the analyte sensors described herein can be polarized anodically to detect for example, changes in current at the working anode that result from the changes in hydrogen peroxide concentration proximal to the working anode that occur as glucose interacts with glucose oxidase as shown in FIG. 1. In typical embodiments of the invention, the current at the working electrode(s) are compared to the current at a reference electrode(s) (a control), with the differences between these measurements providing a value that can then be correlated to the concentration of the analyte being measured. Analyte sensor designs that obtain a current value by obtaining a measurement from a comparison of the currents at these dual electrodes are commonly termed, for example, dual oxygen sensors.

In some embodiments of the invention, the analyte sensor apparatus is designed to function via anodic polarization such that the alteration in current is detected at the anodic working electrode in the conductive layer of the analyte sensor apparatus. Structural design features than can be associated with anodic polarization include designing an appropriate sensor configuration comprising a working electrode which is an anode, a counter electrode which is a cathode and a reference electrode and then selectively disposing the appropriate analyte sensing layer on the appropriate portion of the surface of the anode within this design configuration. Optionally this anodic polarization structural design includes anodes, cathodes and/or working electrodes having different sized surface areas. For example, this structural design includes features where the working electrode (anode) and/or the coated surface of the working electrode is larger than the counter electrode (cathode) and/or the coated surface of the counter electrode. In this context, the alteration in current that can be detected at the anodic working electrode is then correlated with the concentration of the analyte. In certain illustrative examples of this embodiment of the invention, the working electrode is measuring and utilizing hydrogen peroxide in the oxidation reaction (see e.g. FIG. 1), hydrogen peroxide that is produced by an enzyme such as glucose oxidase or lactate oxidase upon reaction with glucose or lactate respectively. Such embodiments of the invention relating to electrochemical glucose and/or lactate sensors having such hydrogen peroxide recycling capabilities are particularly interesting because the recycling of this molecule reduces the amount of hydrogen peroxide that can escape from the sensor into the environment in which it is placed. In this context, implantable sensors that are designed to reduce the release of tissue irritants such as hydrogen peroxide will have improved biocompatibility profiles. Moreover as it is observed that hydrogen peroxide can react with enzymes such as glucose oxidase and compromise their biological function, such sensors can be desired due to their avoidance of this phenomena. Optionally, the analyte modulating layer (e.g. a glucose limiting layer) can include compositions that serve to inhibit the diffusion of hydrogen peroxide out in to the environment in which the sensor is placed. Consequently, such embodiments of the invention improve the biocompatibility of sensors that incorporate enzymes that produce hydrogen peroxide by incorporating hydrogen peroxide recycling elements disclosed herein.

Certain embodiments of the analyte sensors of the invention that comprise a base layer, a conductive layer, an analyte sensing layer, an optional protein layer, an adhesion promoting layer, and analyte modulating layer and a cover layer exhibit a number of unexpected properties. For example, in sensors at are structured to function via anodic polarization versus those structured to function via cathodic polarization, differences in the electrochemical reactions in the analyte sensing layer as well as at the electrode surface generate and/or consume different chemical entities, thereby altering the chemical environment in which the various sensor elements function in different polarities. In this context the sensor structure disclosed herein provides a surprisingly versatile device that is shown to function with an unexpected degree of stability under a variety of different chemical and/or electrochemical conditions.

In certain embodiments of the invention disclosed herein (e.g., those having hydrogen peroxide recycling capabilities) the sensor layer has a plurality of electrodes including a working electrode (e.g. an anode) and a counter electrode (e.g. a cathode), both of which are coated with a analyte sensing layer comprising an enzyme such as glucose oxidase or lactate oxidase. Such sensor designs have surprising properties including an enhanced sensitivity. Without being bound by a specific theory, these properties may result from the enhanced oxidation of hydrogen peroxide at the surface of a working or a counter electrode which produces additional oxygen that can be utilized in the glucose sensing reaction (see, e.g., FIG. 1). Therefore this recycling effect may reduce the oxygen dependent limitations of certain sensor embodiments disclosed herein. Moreover, this design may result in a sensor having a working electrode that can readily reduce available hydrogen peroxide and consequently has a lower electrode potential. Sensors designed to function with lower electrode potentials are typical embodiments of the invention because high electrode potentials in sensors of this type can result in a gas producing hydrolysis reaction which can destabilize the sensors (due to the disruption of sensor layers from gas bubbles produced by hydrolysis reactions). In addition, in sensor embodiments designed so that the counter electrode is coated with a very thin layer of an analyte sensing layer comprising an enzyme such as glucose oxidase or lactate oxidase, the hydrogen peroxide generated in the enzymatic reaction is very close to the reactive surface of the counter electrode. This can increase the overall efficiency of the sensor in a manner that allows for the production of compact sensor designs which include for example, counter electrodes with smaller reactive surfaces.

A specific illustrative example of an analyte sensor apparatus for implantation within a mammal is a peroxide sensor of the following design. A first layer of the peroxide sensor apparatus is a base layer, typically made from a ceramic such as alumina. A subsequent layer disposed upon the base layer is conductive layer including a plurality of electrodes including an anodic working electrode and a reference electrode. A subsequent layer disposed on the conductive layer is an analyte sensing layer that includes crosslinked glucose oxidase which senses glucose and consequently generates hydrogen peroxide as shown in FIG. 1. In the presence of this hydrogen peroxide, the anodic working electrode experiences a measurable increase in current as the hydrogen peroxide generated contacts this anode in the conductive layer and is oxidized. The reference electrode serves as a control and is physically isolated from the working electrode and the hydrogen peroxide generated according to the reaction shown in FIG. 1. This analyte sensing layer is typically less than 1, 0.5, 0.25 or 0.1 microns in thickness and comprises a mixture of crosslinked human serum albumin in a substantially fixed ratio with the crosslinked glucose oxidase, with the glucose oxidase and the human serum albumin being distributed in a substantially uniform manner throughout the sensor layer. A subsequent layer disposed on the sensor layer is a protein layer comprising crosslinked human serum albumin. A subsequent layer disposed on the protein layer is an adhesion promoting layer which promotes the adhesion between the analyte sensing layer and/or the protein layer and an analyte modulating layer which disposed upon these layers. This adhesion promoting layer comprises a silane composition. A subsequent layer disposed on the adhesion promoting layer is the analyte modulating layer in the form of a hydrophilic glucose limiting membrane, typically comprising PDMS or the like, which modulates the diffusion of glucose therethrough. Optionally the analyte modulating layer is a precast PDMS polymer having a plurality of pores designed to facilitate the permeability of selected molecules. In some embodiments, one or more of these pores if filled with a hydrophilic composition. A subsequent layer is a cover layer, typically composed of silicone, which is disposed on at least a portion of the analyte modulating layer, wherein the cover layer further includes an aperture that exposes at least a portion of the analyte modulating layer to the external glucose containing environment so that the glucose can access the analyte sensing layer on the working electrode. This peroxide sensor apparatus functions via anodic polarization such that the hydrogen peroxide signal that is generated by glucose diffusing through the analyte modulating layer and then reacts with the glucose oxidase in the analyte sensing layer creates a detectable change in the current at the anodic working electrode in the conductive layer of the sensor that can be measured by a amperometer. This change in the current at the anodic working electrode can then be correlated with the concentration of glucose in the external environment. Consequently, a sensor of this design can act as a peroxide based glucose sensor.

E. Permutations of Analyte Sensor Apparatus and Elements

As noted above, the invention disclosed herein includes a number of embodiments including sensors having very thin enzyme coatings. Such embodiments of the invention allow artisans to generate a variety of permutations of the analyte sensor apparatus disclosed herein. As noted above, illustrative general embodiments of the sensor disclosed herein include a base layer, a cover layer and at least one layer having a sensor element such as an electrode disposed between the base and cover layers. Typically, an exposed portion of one or more sensor elements (e.g., a working electrode, a counter electrode, reference electrode, etc.) is coated with a very thin layer of material having an appropriate electrode chemistry. For example, an enzyme such as lactate oxidase, glucose oxidase, glucose dehydrogenase or hexokinase, can be disposed on the exposed portion of the sensor element within an opening or aperture defined in the cover layer. FIG. 2 illustrates a cross-section of a typical sensor structure 100 of the present invention. The sensor is formed from a plurality of layers of various conductive and non-conductive constituents disposed on each other according to a method of the invention to produce a sensor structure 100.

As noted above, in the sensors of the invention, the various layers (e.g. the analyte sensing layer) of the sensors can have one or more bioactive and/or inert materials incorporated therein. The term "incorporated" as used herein is meant to describe any state or condition by which the material incorporated is held on the outer surface of or within a solid phase or supporting matrix of the layer. Thus, the material "incorporated" may, for example, be immobilized, physically entrapped, attached covalently to functional groups of the matrix layer(s). Furthermore, any process, reagents, additives, or molecular linker agents which promote the "incorporation" of said material may be employed if these additional steps or agents are not detrimental to, but are consistent with the objectives of the present invention. This definition applies, of course, to any of the embodiments of the present invention in which a bioactive molecule (e.g. an enzyme such as glucose oxidase) is "incorporated." For example, Certain layers of the sensors disclosed herein include a proteinaceous substance such as albumin which serves as a crosslinkable matrix. As used herein, a proteinaceous substance is meant to encompass substances which are generally derived from proteins whether the actual substance is a native protein, an inactivated protein, a denatured protein, a hydrolyzed species, or a derivatized product thereof. Examples of suitable proteinaceous materials include, but are not limited to enzymes such as glucose oxidase and lactate oxidase and the like, albumins (e.g. human serum albumin, bovine serum albumin etc.), caseins, gamma-globulins, collagens and collagen derived products (e.g., fish gelatin, fish glue, animal gelatin, and animal glue).

An illustrative embodiment of the invention is shown in FIG. 2. This embodiment includes an electrically insulating base layer 102 to support the sensor 100. The electrically insulating layer base 102 can be made of a material such as a ceramic substrate, which may be self-supporting or further supported by another material as is known in the art. In an alternative embodiment, the electrically insulating layer 102 comprises a polyimide substrate, for example a polyimide tape, dispensed from a reel. Providing the layer 102 in this form can facilitate clean, high density mass production. Further, in some production processes using such a polyimide tape, sensors 100 can be produced on both sides of the tape.

Typical embodiments of the invention include an analyte sensing layer disposed on the base layer 102. In an illustrative embodiment as shown in FIG. 2 the analyte sensing layer comprises a conductive layer 104 which is disposed on insulating base layer 102. Typically the conductive layer 104 comprises one or more electrodes. The conductive layer 104 can be applied using many known techniques and materials as will be described hereafter, however, the electrical circuit of the sensor 100 is typically defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating protective cover layer 106 such as a polymer coating is typically disposed on portions of the conductive layer 104. Acceptable polymer coatings for use as the insulating protective layer 106 can include, but are not limited to, non-toxic biocompatible polymers such as polyimide, biocompatible solder masks, epoxy acrylate copolymers, or the like. Further, these coatings can be photo-imageable to facilitate photolithographic forming of apertures 108 through to the conductive layer 104. In certain embodiments of the invention, an analyte sensing layer is disposed upon a porous metallic and/or ceramic and/or polymeric matrix with this combination of elements functioning as an electrode in the sensor.

In the sensors of the present invention, one or more exposed regions or apertures 108 can be made through the protective layer 106 to the conductive layer 104 to define the contact pads and electrodes of the sensor 100. In addition to photolithographic development, the apertures 108 can be formed by a number of techniques, including laser ablation, chemical milling or etching or the like. A secondary photoresist can also be applied to the cover layer 106 to define the regions of the protective layer to be removed to form the apertures 108. An operating sensor 100 typically includes a plurality of electrodes such as a working electrode and a counter electrode electrically isolated from each other, however typically situated in close proximity to one another. Other embodiments may also include a reference electrode. Still other embodiments may utilize an separate reference element not formed on the sensor. The exposed electrodes and/or contact pads can also undergo secondary processing through the apertures 108, such as additional plating processing, to prepare the surfaces and/or strengthen the conductive regions.

A analyte sensing layer 110 is typically disposed on one or more of the exposed electrodes of the conductive layer 104 through the apertures 108. Typically, the analyte sensing layer 110 is a sensor chemistry layer and most typically an enzyme layer. Typically, the analyte sensing layer 110 comprises the enzyme glucose oxidase or the enzyme lactate oxidase. In such embodiments, the analyte sensing layer 110 reacts with glucose to produce hydrogen peroxide which modulates a current to the electrode which can be monitored to measure an amount of glucose present. The sensor chemistry layer 110 can be applied over portions of the conductive layer or over the entire region of the conductive layer. Typically the sensor chemistry layer 110 is disposed on portions of a working electrode and a counter electrode that comprise a conductive layer. Some methods for generating the thin sensor chemistry layer 110 include spin coating processes, dip and dry processes, low shear spraying processes, ink-jet printing processes, silk screen processes and the like. Most typically the thin sensor chemistry layer 110 is applied using a spin coating process.

The analyte sensing layer 110 is typically coated with one or more coating layers. In some embodiments of the invention, one such coating layer includes a membrane which can regulate the amount of analyte that can contact an enzyme of the analyte sensing layer. For example, a coating layer can comprise an analyte modulating membrane layer such as a glucose limiting membrane which regulates the amount of glucose that contacts the glucose oxidase enzyme layer on an electrode. Such glucose limiting membranes can be made from a wide variety of materials known to be suitable for such purposes, e.g., silicone, polyurethane, polyurea cellulose acetate, Nafion, polyester sulfonic acid (Kodak AQ), hydrogels or any other membrane known to those skilled in the art. As discussed in the sections below, an illustrative embodiment of the invention is an analyte modulating membrane for use with an analyte sensor (e.g. a glucose limiting membrane) which made from poly(dimethyl siloxane) or the like and which optionally contains a plurality of pores disposed within it so as to facilitate the sensing of the analyte. Optionally one or more of the plurality of pores in the membrane is filled with a hydrophilic composition In some embodiments of the invention, a coating layer is a glucose limiting membrane layer 112 which is disposed above the sensor chemistry layer 110 to regulate glucose contact with the sensor chemistry layer 110. In some embodiments of the invention, an adhesion promoter layer 114 is disposed between the membrane layer 112 and the sensor chemistry layer 110 as shown in FIG. 2 in order to facilitate their contact and/or adhesion. The adhesion promoter layer 114 can be made from any one of a wide variety of materials known in the art to facilitate the bonding between such layers. Typically, the adhesion promoter layer 114 comprises a silane compound. In alternative embodiments, protein or like molecules in the sensor chemistry layer 110 can be sufficiently crosslinked or otherwise prepared to allow the membrane layer 112 to be disposed in direct contact with the sensor chemistry layer 110 in the absence of an adhesion promoter layer 114.

As noted above, embodiments of the present invention can include one or more functional coating layers. As used herein, the term "functional coating layer" denotes a layer that coats at least a portion of at least one surface of a sensor, more typically substantially all of a surface of the sensor, and that is capable of interacting with one or more analytes, such as chemical compounds, cells and fragments thereof, etc., in the environment in which the sensor is disposed. Non-limiting examples of functional coating layers include sensor chemistry layers (e.g., enzyme layers), analyte limiting layers, biocompatible layers; layers that increase the slipperiness of the sensor; layers that promote cellular attachment to the sensor; layers that reduce cellular attachment to the sensor; and the like. Typically analyte modulating layers operate to prevent or restrict the diffusion of one or more analytes, such as glucose, through the layers. Optionally such layers can be formed to prevent or restrict the diffusion of one type of molecule through the layer (e.g. glucose), while at the same time allowing or even facilitating the diffusion of other types of molecules through the layer (e.g. $O_2$). An illustrative functional coating layer is a hydrogel such as those disclosed in U.S. Pat. Nos. 5,786,439 and 5,391,250, the disclosures of each being incorporated herein by reference. The hydrogels described therein are particularly useful with a variety of implantable devices for which it is advantageous to provide a surrounding water layer.

The sensor embodiments disclosed herein can include layers having UV-absorbing polymers. In accordance with one aspect of the present invention, there is provided a sensor including at least one functional coating layer including a UV-absorbing polymer. In some embodiments, the UV-absorbing polymer is a polyurethane, a polyurea or a polyurethane/polyurea copolymer. More typically, the selected UV-absorbing polymer is formed from a reaction mixture including a diisocyanate, at least one diol, diamine or mixture thereof, and a polyfunctional UV-absorbing monomer.

UV-absorbing polymers are used with advantage in a variety of sensor fabrication methods, such as those described in U.S. Pat. No. 5,390,671, to Lord et al., entitled "Transcutaneous Sensor Insertion Set"; U.S. Pat. No. 5,165,407, to Wilson et al., entitled "Implantable Glucose Sensor"; and U.S. Pat. No. 4,890,620, to Gough, entitled "Two-Dimensional Diffusion Glucose Substrate Sensing Electrode", which are incorporated herein in their entireties by reference. However, any sensor production method which includes the step of forming a UV-absorbing polymer layer above or below a sensor element is considered to be within the scope of the present invention. In particular, the inventive methods are not limited to thin-film fabrication methods, and can work with other sensor fabrication methods that utilize UV-laser cutting. Embodiments can work with thick-film, planar or cylindrical sensors and the like, and other sensor shapes requiring laser cutting.

As disclosed herein, the sensors of the present invention are particularly designed for use as subcutaneous or transcutaneous glucose sensors for monitoring blood glucose levels in a diabetic patient. Typically each sensor comprises a plurality of sensor elements, for example electrically conductive elements such as elongated thin film conductors, formed between an underlying insulative thin film base layer and an overlying insulative thin film cover layer.

If desired, a plurality of different sensor elements can be included in a single sensor. For example, both conductive and reactive sensor elements can be combined in one sensor, optionally with each sensor element being disposed on a different portion of the base layer. One or more control elements can also be provided. In such embodiments, the sensor can have defined in its cover layer a plurality of openings or apertures. One or more openings can also be defined in the cover layer directly over a portion of the base layer, in order to provide for interaction of the base layer with one or more analytes in the environment in which the sensor is disposed. The base and cover layers can be comprised of a variety of materials, typically polymers. In more specific embodiments the base and cover layers are comprised of an insulative material such as a polyimide. Openings are typically formed in the cover layer to expose distal end electrodes and proximal end contact pads. In a glucose monitoring application, for example, the sensor can be placed transcutaneously so that the distal end electrodes are in contact with patient blood or extracellular fluid, and the contact pads are disposed externally for convenient connection to a monitoring device.

The sensors of the invention can have any desired configuration, for example planar or cylindrical. The base layer 102 can be self-supportive, such as a rigid polymeric layer, or non-self supportive, such as a flexible film. The latter embodiment is desirable in that it permits continuous manufacture of sensors using, for example, a roll of a polymeric film which is continuously unwound and upon which sensor elements and coating layers are continuously applied.

A general embodiment of the invention is a sensor designed for implantation within a body that comprises a base layer, an analyte sensing layer disposed upon the base layer which includes a plurality of sensor elements, an enzyme layer (typically less than 2 microns in thickness) disposed upon the analyte sensing layer which coats all of the plurality of sensing elements on the conductive layer, and one or more coating layers. Typically the enzyme layer comprises glucose oxidase, typically in a substantially fixed ratio with a carrier protein. In a specific embodiment, the glucose oxidase and the carrier protein are distributed in a substantially uniform manner throughout the disposed enzyme layer. Typically the carrier protein comprises albumin, typically in an amount of about 5% by weight. As used herein, "albumin" refers to those albumin proteins typically used by artisans to stabilize polypeptide compositions such as human serum albumin, bovine serum albumin and the like. In some embodiments of the invention, a coating layer is an analyte contacting layer which is disposed on the sensor so as to regulate the amount of analyte that can contact the enzyme layer. In further embodiments, the sensor includes an adhesion promoter layer disposed between the enzyme layer and the analyte contacting layer and the enzyme layer is less than 1, 0.5, 0.25 or 0.1 microns in thickness.

One aspect of the present invention involves processes for making sensors having improved electrode chemistry coatings (e.g., enzyme coatings of less than 2 microns in thickness) with enhanced material properties. Methods for producing the extremely thin enzyme coatings of the invention include spin coating processes, dip and dry processes, low shear spraying processes, ink-jet printing processes, silk screen processes and the like. Typically, such coatings are vapor crosslinked subsequent to their application. Surprisingly, sensors produced by these processes have material properties that exceed those of sensors having coatings produced by electrodeposition including enhanced longevity, linearity, regularity as well as improved signal to noise ratios. In addition, certain sensor embodiments of the invention that utilize glucose oxidase coatings formed by such processes are designed to recycle hydrogen peroxide and improve the biocompatibility profiles of such sensors. Illustrative embodiments of the invention include those designed to both consume hydrogen peroxide and recycle oxygen.

In this context, an illustrative embodiment of the invention is a method of making a less than about 2 micron coating of stabilized glucose oxidase on the surface of a matrix such as an electrode comprising combining glucose oxidase with albumin in a fixed ratio (one that is typically optimized for glucose oxidase stabilizing properties) and applying the glucose oxidase and albumin mixture to the surface of the matrix by a process selected from the group consisting of a spin coating process, a dip and dry process, a microdeposition process, a jet printer deposition process, a screen printing process or a doctor blading process. Typically the stabilized glucose oxidase coating is applied to the surface of an electrode by a spin coating process. In some embodiments, the glucose oxidase/albumin is prepared in a physiological solution (e.g., phosphate buffered saline at neutral pH) with the albumin being present in an amount of about 5% albumin by weight. Optionally the stabilized glucose oxidase layer that is formed on the conductive layer is less than 2, 1, 0.5, 0.25 or 0.1 microns in thickness. A closely related embodiment of the invention is a stabilized glucose oxidase layer for coating the surface of an electrode wherein the glucose oxidase is mixed with a carrier protein in a fixed ratio within the layer, the glucose oxidase and the carrier protein are distributed in a substantially uniform manner throughout the layer. Typically the layer is less than 2 microns in thickness.

Embodiments of the invention include a design where an analyte sensing layer is disposed upon a porous metallic and/or ceramic and/or polymeric matrix with this combination of elements functioning as an electrode in the sensor. A related embodiment of the invention is an electrochemical analyte sensor which includes a base layer, a conductive layer disposed upon the base layer that includes at least one working electrode and at least one counter electrode, an analyte sensing layer disposed upon the conductive layer, wherein the analyte sensing layer is less than 2 microns in thickness; and an analyte modulating layer that regulates the amount of analyte that contacts the enzyme layer, typically by limiting the amount of analyte that can diffuse through the layer and contact the analyte sensing layer. In an optional embodiment of the invention, the working electrode and/or the coated surface of the working electrode is larger than counter electrode and/or the coated surface of the counter electrode. In some embodiments, the enzyme layer comprises glucose oxidase stabilized by coating it on the working electrode and the counter electrode in combination with a carrier protein in a fixed ratio. In one embodiment, this glucose oxidase enzyme layer substantially covers the conductive layer. Embodiments where the glucose oxidase enzyme layer is disposed in a uniform coating over the whole conductive layer are typical because they may avoid problems associated with sensors having multiple different coatings on a single layer such as the selective delamination of different coatings having different material properties. Typically, the sensor includes an adhesion promoting layer disposed between the enzyme layer and the analyte modulating layer.

A related embodiment of the invention is an electrochemical analyte sensor which includes a base layer, a conductive layer disposed upon the base layer that includes at least one working electrode, at least one reference electrode and at least one counter electrode, an enzyme layer disposed upon the conductive layer, and an analyte modulating cover layer that regulates the amount of analyte that contacts the enzyme layer. In some embodiments, the enzyme layer is less than 2 microns in thickness and is coated on at least a portion of the working electrode, the reference electrode and the counter electrode. In an illustrative embodiment, the enzyme layer substantially covers the working electrode, the reference electrode and the counter electrode. Optionally, the enzyme layer comprises glucose oxidase in combination with a carrier protein (e.g. albumin) in a fixed ratio. Typically, the sensor includes an adhesion promoting layer disposed between the enzyme layer and the analyte modulating layer.

Yet another embodiment of the invention comprises a glucose sensor for implantation within a body which includes a base layer, a conductive layer disposed upon the base layer, an analyte sensing layer comprising glucose oxidase disposed upon the conductive layer, wherein the glucose oxidase is stabilized by combining it with albumin in a defined ratio and further wherein the glucose oxidase and the albumin are distributed in a substantially uniform manner throughout the disposed layer, and a glucose limiting layer that regulates the amount of glucose that diffuses through the glucose limiting layer and contacts the glucose oxidase layer. In some embodiments, the conductive layer includes a plurality of sensor elements including at least one working electrode and at least one counter electrode. In such sensor embodiments, the analyte sensing layer comprising glucose oxidase is typically less than 2, 1, 0.5, 0.25 or 0.1 microns in thickness and the albumin in the layer is present in an amount of about 5% albumin by weight. Typically the sensor includes an adhesion promoting layer disposed between the analyte sensing layer comprising glucose oxidase and the glucose limiting layer.

F. Analyte Sensor Apparatus Configurations

In a clinical setting, accurate and relatively fast determinations of analytes such as glucose and/or lactate levels can be determined from blood samples utilizing electrochemical sensors. Conventional sensors are fabricated to be large, comprising many serviceable parts, or small, planar-type sensors which may be more convenient in many circumstances. The term "planar" as used herein refers to the well-known procedure of fabricating a substantially planar structure comprising layers of relatively thin materials, for example, using the well-known thick or thin-film techniques. See, for example, Liu et al., U.S. Pat. No. 4,571,292, and Papadakis et al., U.S. Pat. No. 4,536,274, both of which are incorporated herein by reference. As noted below, embodiments of the invention disclosed herein have a wider range of geometrical configurations (e.g. planar) than existing sensors in the art. In addition, certain embodiments of the invention include one or more of the sensors disclosed herein coupled to another apparatus such as a medication infusion pump.

Figure 3:
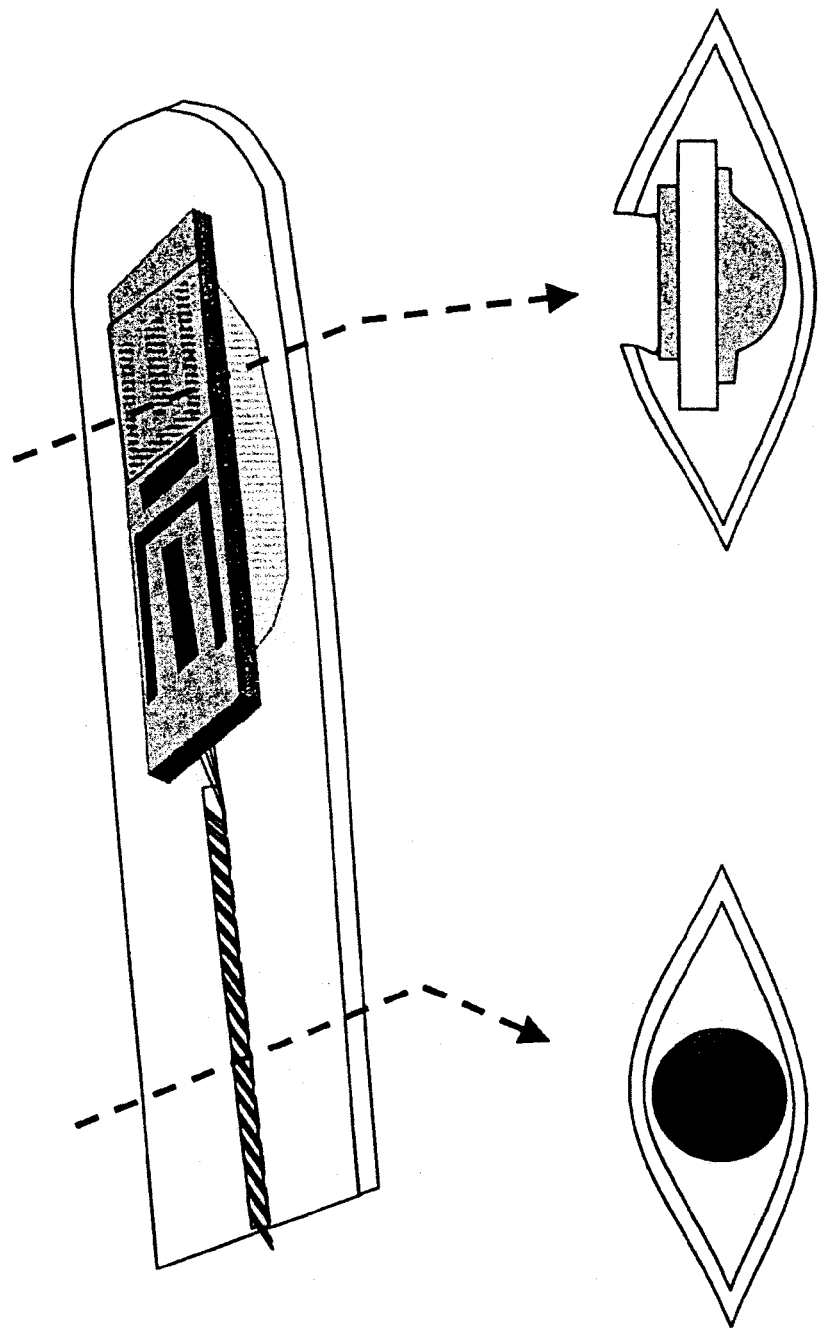
FIG. 3 provides an overview (upper) and cross sectional views (lower) of a relatively flat "ribbon" type sensor configuration that can be made with the analyte sensor apparatus.

FIG. 2 provides a diagrammatic view of a typical analyte sensor configuration of the current invention. FIG. 3 provides an overview (upper) and cross sectional views (lower) of a relatively flat "ribbon" type configuration that can be made with the analyte sensor apparatus. Such "ribbon" type configurations illustrate an advantage of the sensors disclosed herein that arises due to the spin coating of sensing enzymes such as glucose oxidase, a manufacturing step that produces extremely thin enzyme coatings that allow for the design and production of highly flexible sensor geometries. Such thin enzyme coated sensors provide further advantages such as allowing for a smaller sensor area while maintaining sensor sensitivity, a highly desirable feature for implantable devices (e.g. smaller devices are easier to implant). Consequently, sensor embodiments of the invention that utilize very thin analyte sensing layers that can be formed by processes such as spin coating can have a wider range of geometrical configurations (e.g. planar) than those sensors that utilizes enzyme layers formed via processes such as electrodeposition.

Figure 4A:
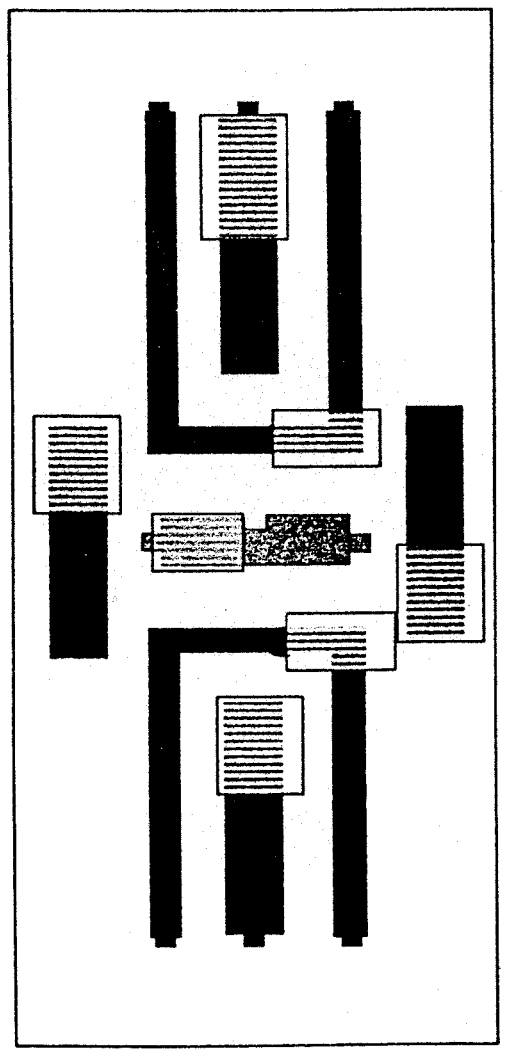
FIGS. 4A and 4B illustrate various sensor configurations that include multiple conductive elements such as multiple working, counter and reference electrodes.
Figure 4B:
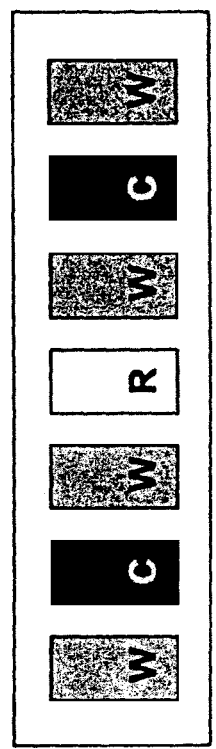

FIGS. 4A and 4B illustrate various sensor configurations that include multiple conductive elements such as multiple working, counter and reference electrodes. Advantages of such configurations include increased surface are which provides for greater sensor sensitivity. For example in the sensor configuration shown in FIG. 4B, this pattern (including seven vias) introduces a third working sensor. One obvious advantage of such a configuration is signal averaging of three sensors which increases sensor accuracy. Other advantages include the ability to measure multiple analytes. In particular, analyte sensor configurations that include electrodes in this arrangement (e.g. multiple working, counter and reference electrodes) and be incorporated into multiple analyte sensors. The measurement of multiple analytes such as oxygen, hydrogen peroxide, glucose, lactate, potassium, calcium, and any other physiologically relevant substance/analyte provides a number of advantages, for example the ability of such sensors to provide a linear response as well as ease in calibration and/or recalibration.

An exemplary multiple sensor device comprises a single device having a first sensor which is polarized cathodically and designed to measure the changes in oxygen concentration that occur at the working electrode (a cathode) as a result of glucose interacting with glucose oxidase; and a second sensor which is polarized anodically and designed to measure changes in hydrogen peroxide concentration that occurs at the working electrode (an anode) as a result of glucose coming form the external environment and interacting with glucose oxidase. As is known in the art, in such designs, the first oxygen sensor will typically experience a decrease in current at the working electrode as oxygen contacts the sensor while the second hydrogen peroxide sensor will typically experience an increase in current at the working electrode as the hydrogen peroxide generated as shown in FIG. 1 contacts the sensor. In addition, as is known in the art, an observation of the change in current that occurs at the working electrodes as compared to the reference electrodes in the respective sensor systems correlates to the change in concentration of the oxygen and hydrogen peroxide molecules which can then be correlated to the concentration of the glucose in the external environment (e.g. the body of the mammal).

Figure 5A:
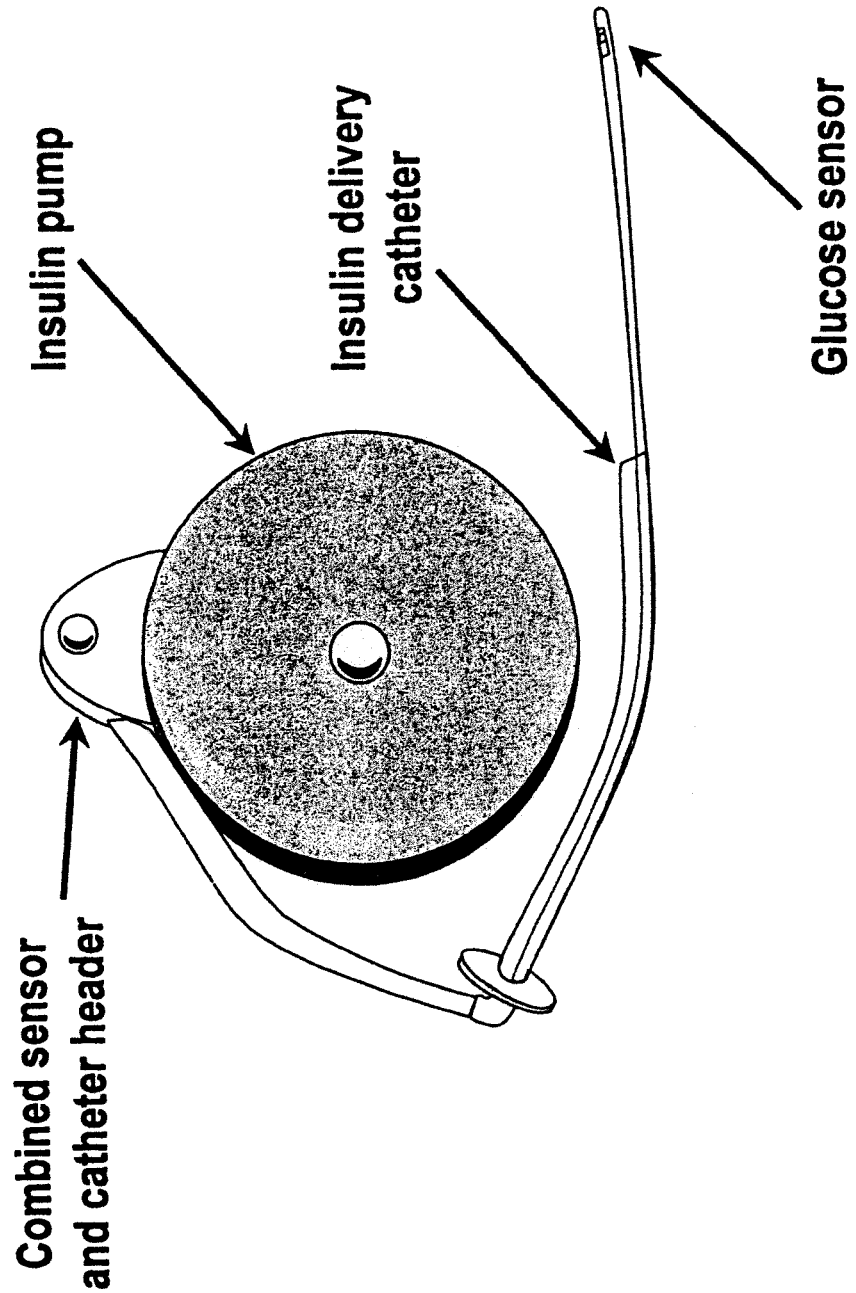
FIG. 5A provides an illustration of how the analyte sensors of the invention can be coupled with other medical devices such as insulin delivery catheters, combined sensor and catheter header and medication infusion pumps.
Figure 6:
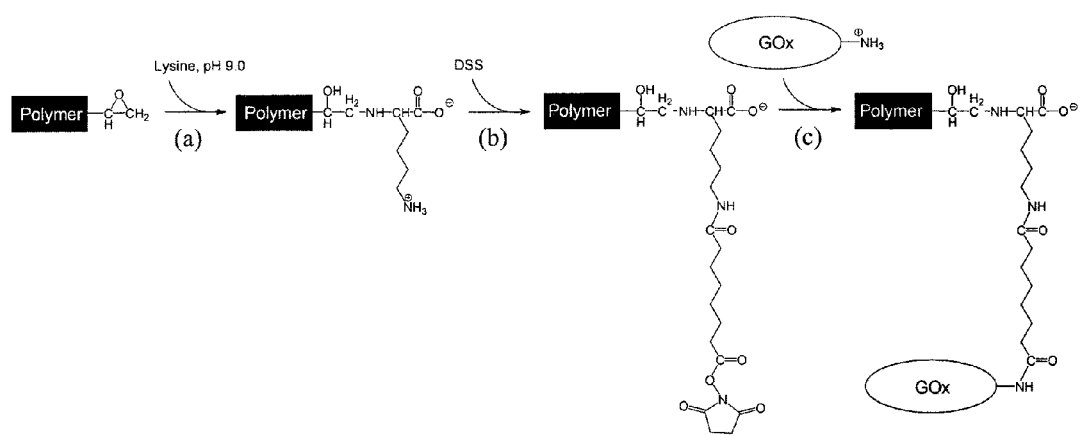
FIG. 6 shows a schematic of the functionalization of an epoxide-activated polymer followed by GOx immobilization via a bifunctional cross-linking agent. (a) A nucleophilic species such as lysine is used to functionalize a polymer such as poly(glycidyl methacrylate-co-ethylene dimethacrylate). (b) The functionalized polymer is activated by a bifunctional cross-linking agent such as DSS (disuccinimidyl suberate). (c) The activated polymer is used as an immobilization substrate for glucose oxidase (GOx).

FIG. 5A provides an illustration of how the analyte sensors of the invention can be coupled with other medical devices such as medication infusion pumps. FIG. 5B provides an illustration of a variation of this scheme where replaceable analyte sensors of the invention can be coupled with other medical devices such as medication infusion pumps, for example by the use of a port couple to the medical device (e.g. a subcutaneous port with a locking electrical connection).

II. Illustrative Methods and Materials for Making Analyte Sensor Apparatus of the Invention A number of articles, U.S. patents and patent application describe the state of the art with the common methods and materials disclosed herein and further describe various elements (and methods for their manufacture) that can be used in the sensor designs disclosed herein. These include for example, U.S. Pat. Nos. 6,413,393; 6,368,274; 5,786,439; 5,777,060; 5,391,250; 5,390,671; 5,165,407, 4,890,620, 5,390,671, 5,390,691, 5,391,250, 5,482,473, 5,299,571, 5,568,806; United States Patent Application 20020090738; as well as PCT International Publication Numbers WO 01/58348, WO 03/034902, WO 03/035117, WO 03/035891, WO 03/023388, WO 03/022128, WO 03/022352, WO 03/023708, WO 03/036255, WO03/036310 and WO 03/074107, the contents of each of which are incorporated herein by reference.

Typical sensors for monitoring glucose concentration of diabetics are further described in Shichiri, et al.: "In Vivo Characteristics of Needle-Type Glucose Sensor-Measurements of Subcutaneous Glucose Concentrations in Human Volunteers," Horm. Metab. Res., Suppl. Ser. 20:17-20 (1988); Bruckel, et al.: "In Vivo Measurement of Subcutaneous Glucose Concentrations with an Enzymatic Glucose Sensor and a Wick Method," Klin. Wochenschr. 67:491-495 (1989); and Pickup, et al.: "In Vivo Molecular Sensing in Diabetes Mellitus: An Implantable Glucose Sensor with Direct Electron Transfer," Diabetologia 32:213-217 (1989). Other sensors are described in, for example Reach, et al., in ADVANCES IN IMPLANTABLE DEVICES, A. Turner (ed.), JAI Press, London, Chap. 1, (1993), incorporated herein by reference.

A. General Methods for Making Analyte Sensors

A typical embodiment of the invention disclosed herein is a method of making a sensor apparatus for implantation within a mammal comprising the steps of: providing a base layer; forming a conductive layer on the base layer, wherein the conductive layer includes an electrode (and typically a working electrode, a reference electrode and a counter electrode); forming an analyte sensing layer on the conductive layer, wherein the analyte sensing layer includes a composition that can alter the electrical current at the electrode in the conductive layer in the presence of an analyte; optionally forming a protein layer on the analyte sensing layer; forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer. In certain embodiments of these methods, the analyte sensor apparatus is formed in a planar geometric configuration As disclosed herein, the various layers of the sensor can be manufactured to exhibit a variety of different characteristics which can be manipulated according to the specific design of the sensor. For example, the adhesion promoting layer includes a compound selected for its ability to stabilize the overall sensor structure, typically a silane composition. In some embodiments of the invention, the analyte sensing layer is formed by a spin coating process and is of a thickness selected from the group consisting of less than 1, 0.5, 0.25 and 0.1 microns in height.

Typically a method of making the sensor includes the step of forming a protein layer on the analyte sensing layer, wherein a protein within the protein layer is an albumin selected from the group consisting of bovine serum albumin and human serum albumin. Typically a method of making the sensor includes the step of forming an analyte sensing layer that comprises an enzyme composition selected from the group consisting of glucose oxidase, glucose dehydrogenase, lactate oxidase, hexokinase and lactate dehydrogenase. In such methods, the analyte sensing layer typically comprises a carrier protein composition in a substantially fixed ratio with the enzyme and the enzyme and the carrier protein are distributed in a substantially uniform manner throughout the analyte sensing layer.

B. Typical Methods for Making Porous Enzyme Matrices

One embodiment of the invention comprises porous metallic matrices. A wide variety of methods for making such materials are known in the art. For example, the past few years have seen increasing interest in porous metallic materials, especially in foams made of metals such as aluminum or aluminum alloys. Consequently, in certain embodiments of the invention, the matrix may comprise a metallic foam. Porous metals are those that contain a multitude of pores, i.e. closed, curved gas voids with a smooth surface. Metal(lic) foams are special cases of porous metals. A solid foam originates from a liquid foam in which gas bubbles are finely dispersed in a liquid. In a metal sponge, space is filled by pieces of metal that form a continuous network and co-exist with a network of empty space which is also interconnected. Illustrative methods and materials of this type are described for example in: Cellular Metals: Manufacture, Properties and Applications: J. Banhart, N. A. Fleck, A. Mortensen (Editors); and Proceedings of the 3rd International Conference on Cellular Metals and Metal Foaming Technology (MetFoam 2003), J. Banhart, M. F. Ashby, N. A. Fleck (Editors), the contents of which are incorporated herein by reference.

In certain specific illustrative methods, the porous metallic substrates can be manufactured by drilling small holes into a metal sheet, film, foil, rod, or block using a laser beam or some other type of drilling technology. In another specific embodiment, a woven wire mesh can be used as a porous metallic substrate. For example, the fabrication of 3-D micromesh Ni Structures using electroplating has been described in the art such as fabrication methods of a 3-D micromesh Ni electrode. Specifically, inverse-micromesh photoresist structures, fabricated by multiple inclined backside exposure, can be used as a mold for Ni electroplating, with Ni meshes of about 3 μm in diameter obtained by this method.

In other specific methods, metallic substrate embodiments of the invention can be manufactured with the desired porosity, pore-size distribution, and tortuosity through a printing process. One embodiment is a printing process for making a porous metallic matrix, the process comprising forming an ink of fine metallic particles suspended in a porogenic carrier solvent, printing the ink onto a substrate, optionally repeating this step to obtain a film of a desired thickness, drying the printed metallic matrix to remove porogenic carrier solvent and then firing the resulting porous bed of metallic powder so as to bond the metallic particles together so that a porous metallic matrix is made.

The metallic substrate may either be printed as a film or within the confines of a mold, either directly in place onto the sensor assembly or onto a temporary substrate. The ink can consist of fine metallic particles suspended in a porogenic carrier. The metallic particles may consist of a single pure metal or alloy. Different types of metallic particles may also be printed either at the same time to form a mixture, or at different times to form layers. The porogenic carrier can consist of a solvent with or without various polymers, glasses, ceramics, and/or frit materials. The mold may consist of various ceramics, polymers, or metals. Many thin layers of ink may need to be printed in order to fill the mold or to obtain a film of the desired thickness. To remove the solvents, the printed metallic matrix can be dried at an appropriate temperature. The resulting porous bed of metallic powder can then be fired approximately in the range of 350° C.-2,000° C. to bond the metallic and, if any, ceramic particles together. This can form a highly porous and tortuous metallic substrate onto which an enzyme such as GOx can be immobilized. If desired, the morphology of the metallic substrate can be adjusted by manipulating the size of the metallic particles as well as the composition of the porogenic carrier. Additionally, various glass, ceramic, and/or metallic particles included in the ink can be etched from the printed material to create pores using materials such as, but not limited to, hydrofluoric acid and sodium hydroxide. Prior to coating the metallic substrate with glucose oxidase, platinum black may or may not be plated using standard techniques.

The enzyme composition can be applied to the porous matrices by any one of a variety of methods known in the art. In one illustrative embodiment, an enzyme such as glucose oxidase can be dissolved in a solvent and dip, spray, or spin coated onto the porous metallic substrate. For some substrate geometries and morphologies, it may be desirable to instead pump the enzyme solution through the pores. The coating solvent may consist of aqueous buffer and/or various organic solvents and/or surfactants including, but not limited to, various alcohols, dimethyl sulfoxide, and polyoxyethylene(20) sorbitan monolaurate ("Tween™ 20"). Ingress of the protein into porous substrates may be promoted by decreasing the viscosity of the enzyme solution through the manipulation of its composition and/or by applying vacuum and/or centrifugation and/or ultrasonic vibration to the coated substrate. Other bio and/or synthetic polymers may also be coated along with the enzyme as filler material such as, but not limited to: bovine serum albumin, human serum albumin, polyethylene glycol, and O',O'-Bis(2-aminopropyl)polyethylene glycol ("Jeffamine®"). The coated enzyme and filler materials (if any) will be immobilized onto the metallic substrate using an appropriate homobifunctional (i.e. glutaraldehyde or disuccinimidyl suberate), heterobifunctional (i.e. succinimidyl-4-[N-maleimidomethyl]cyclohexane-1-carboxylate), trifunctional (i.e. 4-azido-2-nitrophenylbiocytin-4-nitrophenyl ester), and/or zero-length (i.e. 1-ethyl-3-[3-dimethylaminopropyl]carbodiimide hydrochloride) cross-linking agent or agents that could be selected by individuals well versed in fields of protein immobilization, bioconjugate techniques, or polymer chemistry.

In an alternate embodiment, a process provided by SurModics Inc. under the trademark PHOTOLINK™ can be used to immobilize an enzyme such as glucose oxidase onto the porous metallic substrate. Such PHOTOLINK™ methods are set forth in U.S. Pat. Nos. 3,959,078, 4,722,906, 5,229,172; 5,308,641; 5,350,800 and 5,415,938.

As disclosed herein, other embodiments of the invention include an essentially rigid, non-swelling porous enzyme-polymer matrix. In this context, molded continuous rods of macroporous polymers have been developed for use as chromatographic separation media (see, e.g. U.S. Pat. No. 5,453,185 and PCT Publication No. WO 93/07945, the contents of which are incorporated herein by reference). Examples include, but are not limited to poly(glycidyl methacrylate-co-ethylene dimethacrylate) and poly(styrene-co-divinylbenzene). As disclosed in U.S. Pat. No. 5,453,185, a typical polymerization mixture at a minimum contains at least one polyvinyl monomer, a free radical generating initiator, and a porogen. The mixture may also contain one or more monovinyl monomers and/or soluble polymers or insoluble macroporous polymer particles. Suitable polyvinyl monomers include divinylbenzene, divinylnaphthalene, divinylpyridine, alkylene dimethacrylates, hydroxyalkylene dimethacrylates, hydroxyalkylene diacrylates, oligoethylene glycol dimethacrylates, oligoethylene glycol diacrylates, vinyl esters of polycarboxylic acids, divinyl ether, pentaerythritol di-, tri-, or tetramethacrylate or acrylate, trimethylopropane trimethacrylate or acrylate, alkylene bis acrylamides or methacrylamides, and mixtures of any such suitable polyvinyl monomers. The alkylene groups generally contain about 1-6 carbon atoms. Monovinyl monomers which may be used include styrene, ring substituted styrenes wherein the substituents include chloromethyl, alkyl with up to 18 carbon atoms, hydroxyl, t-butyloxycarbonyl, halogen, nitro, amino group, protected hydroxyls or amino groups, vinylnaphthalene, acrylates, methacrylates, vinylacetate, vinylpyrolidone, and mixtures thereof. The polyvinyl monomer or polyvinyl monomer plus the monovinyl monomer are generally present in the polymerization mixture in an amount of from about 10 to 60 vol. %, and more typically in an amount of from about 20 to 40 vol. %. The porogen that is used may be selected from a variety of different types of materials. For example, suitable liquid porogens include aliphatic hydrocarbons, aromatic hydrocarbons, esters, alcohols, ketones, ethers, solutions of soluble polymers, and mixtures thereof. The porogen is generally present in the polymerization mixture in an amount of from about 40 to 90 vol %, more typically from about 60 to 80 vol %. Soluble polymers and insoluble polymer particles may be employed in combination with the monomers. These polymers are added to the polymerization mixture prior to polymerization. The soluble polymers are dissolved out of the plug after its formation by passing a solvent through the plug. The soluble polymers serve as a polymeric porogen to increase the porosity of the final plug. Suitable soluble polymers used herein include non-crosslinked polymers or copolymers of such monomers as styrene or ring substituted styrene, acrylates, methacrylates, dienes, vinylchloride, and vinylacetate. The insoluble polymer particles are used to reduce the volume shrinkage during the polymerization. The lesser the volume of the monomers in the polymerization mixture the smaller the contraction of volume upon polymerization. Suitable insoluble polymer particles used herein include macroporous polymer particles which are cross-linked copolymers of the same monomers. It is, however, common due to compatibility to employ insoluble polymer particles which are formed from the same monomers used to form the polymerization mixture with which they are to be combined. The polymer particles initially have a diameter of from about 1 to 1,000 micrometers. It is not necessary that the mixture of polymer particles have the same particle size. In fact, it is more economical and, therefore common to use irregularly sized polymer particles. While not necessary, the polymer particles may be soaked with a liquid immiscible with the polymerization mixture which can contain an inhibitor which inhibits free radical polymerization. This is done in order to prevent polymerization in the inside of the macroporous particles which would cause filling of the pores and would effectively remove them from the separation process. The rod would then contain nonporous pools unable to contribute to the separation process. Suitable inhibitors include cupric chloride and sodium nitrite. The inhibitor is generally present in an amount of from about 0.001 to 1 wt %, and more typically in an amount of from about 0.1 to 1 wt %, based on the total weight of particles. The polymer particles are typically degassed prior to use in the polymerization mixture. This may be accomplished by any of the conventional means known in the art. It, however, is typical to soak the particles in water, optionally containing a polymerization inhibitor, and remove the air from the pores by keeping the water-polymer particle mixture under the vacuum of a water pump for a suitable period of time such as about 5 to 20 minutes. Excess water may then be removed by filtering. The soluble polymers are generally present in an amount of from about 5 to 40% by volume of the polymerization mixture and the insoluble polymer particles in an amount of from about 5 to 50% by volume. Conventional free-radical generating polymerization initiators may be employed to initiate polymerization. Examples of suitable initiators include peroxides such as OO-t-amyl-O-(2-ethylhexyl)monoperoxycarbonate, dipropylperoxydicarbonate, and benzoyl peroxide, as well as azo compounds such as azobisisobutyronitrile, 2,2'-azobis(2-amidinopropane)dihydrochloride, and 2,2'-azobis(isobutyramide)dihydrate. It has been found that the choice of initiator may be used as a means to control the pore distribution in a plug.

The initiator is generally present in the polymerization mixture in an amount of from about 0.2 to 5% by weight of the monomers.

Polymers useful for making the essentially rigid, non-swelling porous enzyme-polymer matrices are essentially incompressible and do not change their overall size in response to changes in their solvating environment. Adjustments to the polymerization conditions can be used to control the morphology of the pores. Hence, highly porous (50-70%) polymers can be created that possess significant volume fractions of pores in the ranges of 1-100 nm and 100-3,000 nm (i.e. 20% and 80%, respectively). Polymers with this type of pore structure possess a very high specific surface area (i.e. 185 m$^2$/g), and are expected to allow for high enzyme immobilization densities (1-100 mg/mL).

Figure 9:
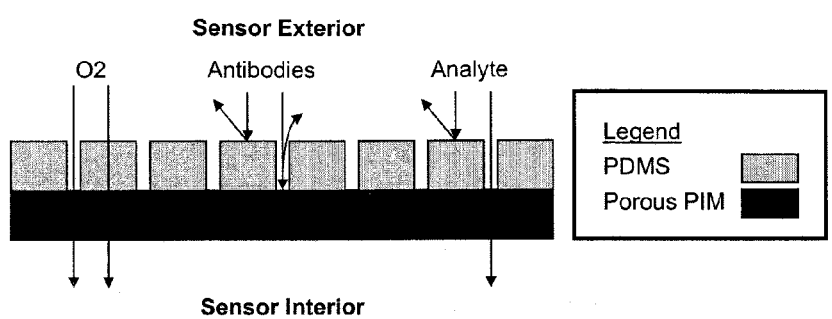
FIG. 9 provides an illustration of a cross-sectional view of a composite permselective membrane with a layered morphology. In this membrane, analyte is not required to diffuse in an extra macroscopic dimension because the pores or "windows" in the PDMS are micro-scale. The illustrated embodiment includes a phase-inversion membrane for immuno-isolation purposes. Features are not necessarily drawn to scale.

In an illustrative embodiment of the rigid, non-swelling porous enzyme-polymer matrices, a nucleophilic compound can be used to functionalize a macroporous, rigid polymer that possesses reactive epoxide groups. A cross-linking agent can then be used to immobilize the bio-sensing enzyme to the polymer via the functional groups of the enzyme and polymer substrate. FIG. 9 depicts an example of this type of GOx immobilization scheme. Other nucleophilic compounds that can be used to functionalize epoxide-activated polymers include, but are not limited to ammonia, ethylenediamine, ethanolamine, carbohydrates, cysteine, and other amino acids. For a given enzyme and functionalized polymer combination, an appropriate homobifunctional (i.e. disuccinimidyl suberate), heterobifunctional (i.e. succinimidyl-4-[N-maleimidomethyl]cyclohexane-1-carboxylate), trifunctional (i.e. 4-azido-2-nitrophenylbiocytin-4-nitrophenyl ester), and/or zero-length (i.e. 1-ethyl-3-[3-dimethylaminopropyl]carbodiimide hydrochloride) cross-linking agent or agents could be selected by individuals well versed in fields of protein immobilization or bioconjugate techniques.

In another embodiment of the rigid, non-swelling porous enzyme-polymer matrices, the bio-sensing enzyme will be directly immobilized onto an epoxide-activated polymer via nucleophilic attack by sulfhydryl, amine, hydroxyl, and/or carboxyl groups that are either native to the enzyme, or have been added to the wild-type peptide sequence via genetic engineering or directed evolution. If desired, the nucleophilic functional groups of the enzyme may be reversibly or irreversibly blocked or protected during the immobilization, using compounds that would be familiar to anyone well versed in protein conjugation (i.e. 5,5'-dithio-bis-[2-nitrobenzoic acid] or N-ethylmaleimide).

In another embodiment of the rigid, non-swelling porous enzyme-polymer matrices, monomers possessing functional groups other than (or in addition to) epoxide groups will be incorporated into the rigid, macroporous polymer during the polymerization reaction (i.e. aminostyrene). As in this embodiment, the bio-sensing enzyme could then be immobilized onto the polymer substrate using an appropriate homobifunctional, heterobifunctional, trifunctional, and/or zero-length cross-linking agent.

In yet another embodiment of the rigid, non-swelling porous enzyme-polymer matrices, PhotoLink® (SurModics, Eden Prairie, Minn.) chemistry can be used to immobilize the bio-sensing enzyme to the molded, porous, rigid polymer. In this embodiment, the polymer substrate need not possess any functional groups because the PhotoLink® chemistry reacts with carbon-hydrogen groups found in virtually every organic polymer.

C. Typical Protocols and Materials Useful in the Manufacture of Analyte Sensors

The disclosure provided herein includes sensors and sensor designs that can be generated using combinations of various well known techniques. The disclosure further provides methods for applying very thin enzyme coatings to these types of sensors as well as sensors produced by such processes. In this context, some embodiments of the invention include methods for making such sensors on a substrate according to art accepted processes. In certain embodiments, the substrate comprises a rigid and flat structure suitable for use in photolithographic mask and etch processes. In this regard, the substrate typically defines an upper surface having a high degree of uniform flatness. A polished glass plate may be used to define the smooth upper surface. Alternative substrate materials include, for example, stainless steel, aluminum, and plastic materials such as delrin, etc. In other embodiments, the substrate is non-rigid and can be another layer of film or insulation that is used as a substrate, for example plastics such as polyimides and the like.

An initial step in the methods of the invention typically includes the formation of a base layer of the sensor. The base layer can be disposed on the substrate by any desired means, for example by controlled spin coating. In addition, an adhesive may be used if there is not sufficient adhesion between the substrate layer and the base layer. A base layer of insulative material is formed on the substrate, typically by applying the base layer material onto the substrate in liquid form and thereafter spinning the substrate to yield the base layer of thin, substantially uniform thickness. These steps are repeated to build up the base layer of sufficient thickness, followed by a sequence of photolithographic and/or chemical mask and etch steps to form the conductors discussed below. In an illustrative form, the base layer comprises a thin film sheet of insulative material, such as ceramic or polyimide substrate. The base layer can comprise an alumina substrate, a polyimide substrate, a glass sheet, controlled pore glass, or a planarized plastic liquid crystal polymer. The base layer may be derived from any material containing one or more of a variety of elements including, but not limited to, carbon, nitrogen, oxygen, silicon, sapphire, diamond, aluminum, copper, gallium, arsenic, lanthanum, neodymium, strontium, titanium, yttrium, or combinations thereof. Additionally, the substrate may be coated onto a solid support by a variety of methods well-known in the art including chemical vapor deposition, physical vapor deposition, or spin-coating with materials such as spin glasses, chalcogenides, graphite, silicon dioxide, organic synthetic polymers, and the like.

The methods of the invention further include the generation of a conductive layer having one or more sensing elements. Typically these sensing elements are electrodes that are formed by one of the variety of methods known in the art such as photoresist, etching and rinsing to define the geometry of the active electrodes. The electrodes can then be made electrochemically active, for example by electrodeposition of Pt black for the working and counter electrode, and silver followed by silver chloride on the reference electrode. A sensor layer such as a sensor chemistry enzyme layer can then be disposed on the sensing layer by electrochemical deposition or a method other than electrochemical deposition such a spin coating, followed by vapor crosslinking, for example with a dialdehyde (glutaraldehyde) or a carbodi-imide.

Electrodes of the invention can be formed from a wide variety of materials known in the art. For example, the electrode may be made of a noble late transition metals. Metals such as gold, platinum, silver, rhodium, iridium, ruthenium, palladium, or osmium can be suitable in various embodiments of the invention. Other compositions such as carbon or mercury can also be useful in certain sensor embodiments. Of these metals, silver, gold, or platinum is typically used as a reference electrode metal. A silver electrode which is subsequently chloridized typically used as the reference electrode. These metals can be deposited by any means known in the art, including the plasma deposition method cited, supra, or by an electroless method which may involve the deposition of a metal onto a previously metallized region when the substrate is dipped into a solution containing a metal salt and a reducing agent. The electroless method proceeds as the reducing agent donates electrons to the conductive (metallized) surface with the concomitant reduction of the metal salt at the conductive surface. The result is a layer of adsorbed metal. (For additional discussions on electroless methods, see: Wise, E. M. Palladium: Recovery, Properties, and Uses, Academic Press, New York, N.Y. (1988); Wong, K. et al. Plating and Surface Finishing 1988, 75, 70-76; Matsuoka, M. et al. Ibid. 1988, 75, 102-106; and Pearlstein, F. "Electroless Plating," Modern Electroplating, Lowenheim, F. A., Ed., Wiley, New York, N.Y. (1974), Chapter 31.). Such a metal deposition process must yield a structure with good metal to metal adhesion and minimal surface contamination, however, to provide a catalytic metal electrode surface with a high density of active sites. Such a high density of active sites is a property necessary for the efficient redox conversion of an electroactive species such as hydrogen peroxide.

In an exemplary embodiment of the invention, the base layer is initially coated with a thin film conductive layer by electrode deposition, surface sputtering, or other suitable process step. In one embodiment this conductive layer may be provided as a plurality of thin film conductive layers, such as an initial chrome-based layer suitable for chemical adhesion to a polyimide base layer followed by subsequent formation of thin film gold-based and chrome-based layers in sequence. In alternative embodiments, other electrode layer conformations or materials can be used. The conductive layer is then covered, in accordance with conventional photolithographic techniques, with a selected photoresist coating, and a contact mask can be applied over the photoresist coating for suitable photoimaging. The contact mask typically includes one or more conductor trace patterns for appropriate exposure of the photoresist coating, followed by an etch step resulting in a plurality of conductive sensor traces remaining on the base layer. In an illustrative sensor construction designed for use as a subcutaneous glucose sensor, each sensor trace can include three parallel sensor elements corresponding with three separate electrodes such as a working electrode, a counter electrode and a reference electrode.

Portions of the conductive sensor layers are typically covered by a insulative cover layer, typically of a material such as a silicon polymer and/or a polyimide. The insulative cover layer can be applied in any desired manner. In an exemplary procedure, the insulative cover layer is applied in a liquid layer over the sensor traces, after which the substrate is spun to distribute the liquid material as a thin film overlying the sensor traces and extending beyond the marginal edges of the sensor traces in sealed contact with the base layer. This liquid material can then be subjected to one or more suitable radiation and/or chemical and/or heat curing steps as are known in the art. In alternative embodiments, the liquid material can be applied using spray techniques or any other desired means of application. Various insulative layer materials may be used such as photoimagable epoxyacrylate, with an illustrative material comprising a photoimagable polyimide available from OCG, Inc. of West Paterson, N.J., under the product number 7020.

As noted above, appropriate electrode chemistries defining the distal end electrodes can be applied to the sensor tips, optionally subsequent to exposure of the sensor tips through the openings. In an illustrative sensor embodiment having three electrodes for use as a glucose sensor, an enzyme (typically glucose oxidase) is provided within one of the openings, thus coating one of the sensor tips to define a working electrode. One or both of the other electrodes can be provided with the same coating as the working electrode. Alternatively, the other two electrodes can be provided with other suitable chemistries, such as other enzymes, left uncoated, or provided with chemistries to define a reference electrode and a counter electrode for the electrochemical sensor.

A significant aspect of the present invention involves processes for making sensors having extremely thin coatings for electrode chemistries (e.g., enzyme coatings of less than 2 microns in thickness) with enhanced material properties. Methods for producing the extremely thin enzyme coatings of the invention include spin coating processes, dip and dry processes, low shear spraying processes, ink-jet printing processes, silk screen processes and the like. As artisans can readily determine the thickness of an enzyme coat applied by process of the art, they can readily identify those methods capable of generating the extremely thin coatings of the invention. Typically, such coatings are vapor crosslinked subsequent to their application. Surprisingly, sensors produced by these processes have material properties that exceed those of sensors having coatings produced by electrodeposition including enhanced longevity, linearity, regularity as well as improved signal to noise ratios. In addition, embodiments of the invention that utilize glucose oxidase coatings formed by such processes are designed to recycle hydrogen peroxide and improve the biocompatibility profiles of such sensors.

While not being bound by a specific scientific theory, it is believed that the surprising properties of sensors produced by such processes have enhanced characteristics as compared to those generated by electrodeposition because electrodeposition produces 3-5 micron thick enzyme layers in which only a fraction of the reactive enzyme is able to access the analyte to be sensed. Moreover, in sensors utilizing glucose oxidase, the thick coatings produced by electrodeposition may hinder the ability of hydrogen peroxide generated at the reactive interface to reach the sensor surface and thereby generate a signal. Moreover, hydrogen peroxide that is unable to reach a sensor surface due to such thick coatings typically diffuses away from the sensor into the environment in which the sensor is placed, thereby decreasing the biocompatibility of such sensors. In addition, as glucose oxidase and albumin have different isoelectric points, electrodeposition processes can result in a surface coating in which an optimally determined ratio of enzyme to carrier protein is detrimentally altered and further wherein the glucose oxidase and the carrier protein are not distributed in a substantially uniform manner throughout the disposed enzyme layer. The thin coating processes utilized to produce the sensors disclosed herein avoid these problems associated with electrodeposition.

Sensors generated by processes such as spin coating processes also avoid other problems associated with electrodeposition, such as those pertaining to the material stresses placed on the sensor during the electrodeposition process. In particular, the process of electrodeposition is observed to produce mechanical stresses on the sensor, for example mechanical stresses that result from tensile and/or compression forces. In certain contexts, such mechanical stresses may result in sensors having coatings with some tendency to crack or delaminate. This is not observed in coatings disposed on sensor via spin coating or other low-stress processes. Consequently, yet another embodiment of the invention is a method of avoiding the electrodeposition influenced cracking and or delamination of a coating on a sensor comprising applying the coating via a spin coating process.

Subsequent to treatment of the sensor elements, one or more additional functional coating or cover layers can then be applied by any one of a wide variety of methods known in the art, such as spraying, dipping, etc. Some embodiments of the present invention include an analyte modulating layer deposited over the enzyme-containing layer. In addition to its use in modulating the amount of analyte(s) that contacts the active sensor surface, by utilizing an analyte limiting membrane layer, the problem of sensor fouling by extraneous materials is also obviated. As is known in the art, the thickness of the analyte modulating membrane layer can influence the amount of analyte that reaches the active enzyme. Consequently, its application is typically carried out under defined processing conditions, and its dimensional thickness is closely controlled. As in the microfabrication of the underlying layers can be a factor which affects close dimensional control over the analyte modulating membrane layer is the composition of the analyte limiting membrane layer material itself. In this regard, it has been discovered that several types of copolymers, for example, a copolymer of a siloxane and a nonsiloxane moiety, are particularly useful. These materials can be microdispensed or spin-coated to a controlled thickness. Their final architecture may also be designed by patterning and photolithographic techniques in conformity with the other discrete structures described herein. Examples of these nonsiloxane-siloxane copolymers include, but are not limited to, dimethylsiloxane-alkene oxide, tetramethyldisiloxane-divinylbenzene, tetramethyldisiloxane-ethylene, dimethylsiloxane-silphenylene, dimethylsiloxane-silphenylene oxide, dimethylsiloxane-a-methylstyrene, dimethylsiloxane-bisphenol A carbonate copolymers, or suitable combinations thereof. The percent by weight of the nonsiloxane component of the copolymer can be preselected to any useful value but typically this proportion lies in the range of about 40-80 wt %. Among the copolymers listed above, the dimethylsiloxane-bisphenol A carbonate copolymer which comprises 50-55 wt % of the nonsiloxane component is typical. These materials may be purchased from Petrarch Systems, Bristol, Pa. (USA) and are described in this company's products catalog. Other materials which may serve as analyte limiting membrane layers include, but are not limited to, polyurethanes, cellulose acetate, cellulose nitrate, silicone rubber, or combinations of these materials including the siloxane nonsiloxane copolymer, where compatible.

In some embodiments of the invention, the sensor is made by methods which apply an analyte modulating layer that comprises a hydrophilic membrane coating which can regulate the amount of analyte that can contact the enzyme of the sensor layer. For example, the cover layer that is added to the glucose sensors of the invention can comprise a glucose limiting membrane, which regulates the amount of glucose that contacts glucose oxidase enzyme layer on an electrode. Such glucose limiting membranes can be made from a wide variety of materials known to be suitable for such purposes, e.g., silicones such as polydimethyl siloxane and the like, polyurethanes, cellulose acetates, Nafion, polyester sulfonic acids (e.g. Kodak AQ), hydrogels or any other membrane known to those skilled in the art that is suitable for such purposes. In certain embodiments of the invention pertaining to sensors having hydrogen peroxide recycling capabilities, the membrane layer that is disposed on the glucose oxidase enzyme layer functions to inhibit the release of hydrogen peroxide into the environment in which the sensor is placed and to facilitate the contact between the hydrogen peroxide molecules and the electrode sensing elements.

In some embodiments of the methods of invention, an adhesion promoter layer is disposed between a cover layer (e.g. an analyte modulating membrane layer) and a sensor chemistry layer in order to facilitate their contact and is selected for its ability to increase the stability of the sensor apparatus. As noted herein, compositions of the adhesion promoter layer are selected to provide a number of desirable characteristics in addition to an ability to provide sensor stability. For example, some compositions for use in the adhesion promoter layer are selected to play a role in interference rejection as well as to control mass transfer of the desired analyte. The adhesion promoter layer can be made from any one of a wide variety of materials known in the art to facilitate the bonding between such layers and can be applied by any one of a wide variety of methods known in the art. Typically, the adhesion promoter layer comprises a silane compound such as γ-aminopropyltrimethoxysilane. In certain embodiments of the invention, the adhesion promoting layer and/or the analyte modulating layer comprises an agent selected for its ability to crosslink a siloxane moiety present in a proximal layer. In other embodiments of the invention, the adhesion promoting layer and/or the analyte modulating layer comprises an agent selected for its ability to crosslink an amine or carboxyl moiety of a protein present in a proximal layer. In an optional embodiment, the AP layer further comprises Polydimethyl Siloxane (PDMS), a polymer typically present in analyte modulating layers such as a glucose limiting membrane. In illustrative embodiments the formulation comprises 0.5-20% PDMS, typically 5-15% PDMS, and most typically 10% PDMS. The addition of PDMS to the AP layer can be advantageous in contexts where it diminishes the possibility of holes or gaps occurring in the AP layer as the sensor is manufactured.

As noted above, a coupling reagent commonly used for promoting adhesion between sensor layers is γ-aminopropyltrimethoxysilane. The silane compound is usually mixed with a suitable solvent to form a liquid mixture. The liquid mixture can then be applied or established on the wafer or planar sensing device by any number of ways including, but not limited to, spin-coating, dip-coating, spray-coating, and microdispensing. The microdispensing process can be carried out as an automated process in which microspots of material are dispensed at multiple preselected areas of the device. In addition, photolithographic techniques such as "lift-off" or using a photoresist cap may be used to localize and define the geometry of the resulting permselective film (i.e. a film having a selective permeability). Solvents suitable for use in forming the silane mixtures include aqueous as well as water-miscible organic solvents, and mixtures thereof. Alcoholic water-miscible organic solvents and aqueous mixtures thereof are particularly useful. These solvent mixtures may further comprise nonionic surfactants, such as polyethylene glycols (PEG) having a for example a molecular weight in the range of about 200 to about 6,000. The addition of these surfactants to the liquid mixtures, at a concentration of about 0.005 to about 0.2 g/dL of the mixture, aids in planarizing the resulting thin films. Also, plasma treatment of the wafer surface prior to the application of the silane reagent can provide a modified surface which promotes a more planar established layer. Water-immiscible organic solvents may also be used in preparing solutions of the silane compound. Examples of these organic solvents include, but are not limited to, diphenylether, benzene, toluene, methylene chloride, dichloroethane, trichloroethane, tetrachloroethane, chlorobenzene, dichlorobenzene, or mixtures thereof. When protic solvents or mixtures thereof are used, the water eventually causes hydrolysis of the alkoxy groups to yield organosilicon hydroxides (especially when n=1) which condense to form poly(organosiloxanes). These hydrolyzed silane reagents are also able to condense with polar groups, such as hydroxyls, which may be present on the substrate surface. When aprotic solvents are used, atmospheric moisture may be sufficient to hydrolyze the alkoxy groups present initially on the silane reagent. The R' group of the silane compound (where n=1 or 2) is chosen to be functionally compatible with the additional layers which are subsequently applied. The R' group usually contains a terminal amine group useful for the covalent attachment of an enzyme to the substrate surface (a compound, such as glutaraldehyde, for example, may be used as a linking agent as described by Murakami, T. et al., Analytical Letters 1986, 19, 1973-86).

Like certain other coating layers of the sensor, the adhesion promoter layer can be subjected to one or more suitable radiation and/or chemical and/or heat curing steps as are known in the art. In alternative embodiments, the enzyme layer can be sufficiently crosslinked or otherwise prepared to allow the membrane cover layer to be disposed in direct contact with the sensor chemistry layer in the absence of an adhesion promoter layer.

An illustrative embodiment of the invention is a method of making a sensor by providing a base layer, forming a sensor layer on the base layer, spin coating an enzyme layer on the sensor layer and then forming an analyte contacting layer (e.g. an analyte modulating layer such as a glucose limiting membrane) on the sensor, wherein the analyte contacting layer regulates the amount of analyte that can contact the enzyme layer. In some methods, the enzyme layer is vapor crosslinked on the sensor layer. In a typical embodiment of the invention, the sensor layer is formed to include at least one working electrode and at least one counter electrode. In certain embodiments, the enzyme layer is formed on at least a portion of the working electrode and at least a portion of the counter electrode. Typically, the enzyme layer that is formed on the sensor layer is less than 2, 1, 0.5, 0.25 or 0.1 microns in thickness. Typically, the enzyme layer comprises one or more enzymes such as glucose oxidase, glucose dehydrogenase, lactate oxidase, hexokinase or lactate dehydrogenase and/or like enzymes. In a specific method, the enzyme layer comprises glucose oxidase that is stabilized by coating it on the sensor layer in combination with a carrier protein in a fixed ratio. Typically the carrier protein is albumin. Typically such methods include the step of forming an adhesion promoter layer disposed between the glucose oxidase layer and the analyte contacting layer. Optionally, the adhesion promoter layer is subjected to a curing process prior to the formation of the analyte contacting layer.

A related embodiment of the invention is a method of making a glucose sensor by providing a base layer, forming a sensor layer on the base layer that includes at least one working electrode and at least one counter electrode, forming a glucose oxidase layer on the sensor layer by a spin coating process (a layer which is typically stabilized by combining the glucose oxidase with albumin in a fixed ratio), wherein the glucose oxidase layer coats at least a portion of the working electrode and at least a portion of the counter electrode, and then forming a glucose limiting layer on the glucose sensor so as to regulate the amount of glucose that can contact the glucose oxidase layer. In such processes, the glucose oxidase layer that is formed on the sensor layer is typically less than 2, 1, 0.5, 0.25 or 0.1 microns in thickness. Typically, the glucose oxidase coating is vapor crosslinked on the sensor layer. Optionally, the glucose oxidase coating covers the entire sensor layer. In certain embodiments of the invention, an adhesion promoter layer disposed between the glucose oxidase layer and the analyte contacting layer. In certain embodiments of the invention, the analyte sensor further comprises one or more cover layers which are typically electrically insulating protective layers (see, e.g. element 106 in FIG. 2). Typically, such cover layers are disposed on at least a portion of the analyte modulating layer.

The finished sensors produced by such processes are typically quickly and easily removed from a supporting substrate (if one is used), for example, by cutting along a line surrounding each sensor on the substrate. The cutting step can use methods typically used in this art such as those that include a UV laser cutting device that is used to cut through the base and cover layers and the functional coating layers along a line surrounding or circumscribing each sensor, typically in at least slight outward spaced relation from the conductive elements so that the sufficient interconnected base and cover layer material remains to seal the side edges of the finished sensor. In addition, dicing techniques typically used to cut ceramic substrates can be used with the appropriate sensor embodiments. Since the base layer is typically not physically attached or only minimally adhered directly to the underlying supporting substrate, the sensors can be lifted quickly and easily from the supporting substrate, without significant further processing steps or potential damage due to stresses incurred by physically pulling or peeling attached sensors from the supporting substrate. The supporting substrate can thereafter be cleaned and reused, or otherwise discarded. Alternatively, the functional coating layer(s) can be applied after the sensor including base layer, sensor elements and cover layer is removed from the supporting substrate by cutting.

D. Micro-Fabricated Poly(Dimethyl Siloxane) Membrane for Use as the Permselective Sensor Layer As noted above, certain sensor embodiments achieve their bio-specificity through immobilized enzymes such as glucose oxidase (GOx) or lactate dehydrogenase (LDH), which consume oxygen along with glucose or lactate (the sensor analytes) as co-reactants. To minimize the sensitivity of the reaction rate to the oxygen concentration in such sensors, a molar excess of oxygen is required. However, normal physiologic conditions are such that glucose (~5 mM) and lactate (~1 mM) are almost always found in molar excess of oxygen (~0.05 mM). Hence, to address this "oxygen deficit" problem, most existing sensor designs employ a membrane that is significantly more permeable to oxygen than it is to the analyte (e.g. a glucose limiting membrane). These permselective membranes usually contain poly(dimethylsiloxane) (PDMS), as it is biocompatible and typically possesses an unusually high permeability to oxygen and virtually no permeability to analytes such as glucose or lactate. Limited analyte permeability is typically imparted upon the PDMS-based material either by co-polymerizing PDMS with a hydrophilic polymer (i.e. Jeffamine®) or by cutting a macroscopic "window" into a tube or sheet of PDMS.

Figure 7:
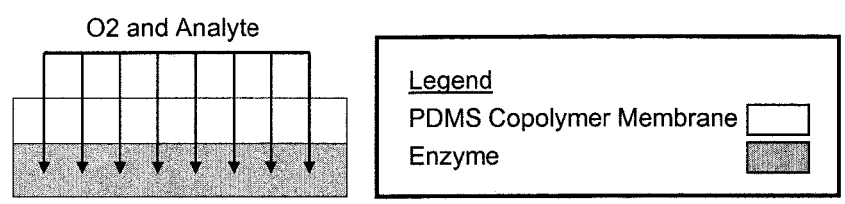
FIG. 7 provides an illustration of a copolymer-type permselective membrane as used in an enzymatic biosensor. In this membrane, both oxygen and analyte effectively diffuse through the copolymer in one macroscopic dimension.
Figure 8:
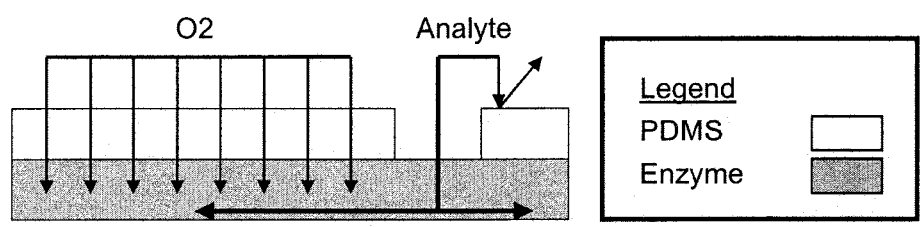
FIG. 8 provides an illustration of a macroscopic window-type permselective membrane as used in an enzymatic biosensor. In this membrane, analyte is required to diffuse in an extra macroscopic dimension.

Copolymer-type permselective membranes have successfully been used in clinically approved short-term (less than 1-week) subcutaneous glucose sensors (e.g. Continuous Glucose Monitoring Systems ("CGMS) and/or a Telemetered Glucose Monitoring Systems ("TGMS"). This type of membrane simply requires analyte to diffuse across its thickness, which is optimal for sensor linearity and response time (FIG. 7). However, due to the poor long-term (i.e. 1-year) in vivo stability of hydrophilic polymers, the feasibility of using such a permselective membrane in a long-term implantable sensor remains in doubt. Meanwhile, macroscopic window-type permselective membranes offer excellent long-term stability, in vivo. However, this type of membrane requires analyte to diffuse in an extra macroscopic dimension (FIG. 8), which can negatively impact sensor linearity as well as response time. Embodiments of the invention produce a permselective membrane fashioned from micro-fabricated PDMS that possesses the inherent advantages of both co-polymer and window-type biosensor membranes. While others have constructed PDMS microstructures through the casting of PDMS pre-polymers into complementary micro-fabricated relief patterns (e.g. Kumar et al., 1994, *Langmuir* 10: 1498-1511; Dapprich, 2003, U.S. Pat. No. 6,585,939), no one has previously described the use of micro-fabricated PDMS as the permselective membrane in an enzymatic electrochemical biosensor.

In one embodiment of the invention, photolithography, lithographic molding, thick-film printing, plasma polymerization (with or without shadow-masking), or discrete nano-dispensing can be used to micro-pattern a curable PDMS functionalized derivative, co-polymer, or mixture thereof onto a pre-cast immuno-isolation membrane. Vacuum or a pressure gradient may or may not be applied to promote the filling of the pores of the immuno-isolation membrane. Composite membranes fashioned in such a manner can possess morphologies that are layered (FIG. 9), pore-filled (FIG. 10), or some combination thereof.

In another embodiment of the invention, a curable PDMS derivative, co-polymer, or mixture thereof can be micro-patterned onto a temporary substrate using the aforementioned techniques. In the final sensor assembly, the stand-alone part may be used with a phase-inversion membrane ("PIM") that may either be cast as a separate part or on top of the PDMS (filling its pores). Various methods for promoting adhesion may be employed by individuals skilled in the art. In an alternate embodiment, a curable PDMS derivative, co-polymer, or mixture thereof can be micro-patterned directly onto the sensor assembly, using the techniques described above. A PIM may be placed or cast on top of the micro-patterned PDMS. Various methods for promoting adhesion may be employed by individuals skilled in the art. In another embodiment, a laser can be used to micro-machine holes (0.1-1000 microns) into a formed piece of PDMS co-polymer (or another polymeric composition such as "silicone rubber") to form a microporous membrane. Again, the PDMS membrane may be used with or without a PIM in the final sensor assembly. Various methods for promoting adhesion can be employed by individuals skilled in the art.

Illustrative chemically active groups that can be used to functionalize the PDMS and/or PDMS co-polymer include, but are not limited to: methacrylates, acrylates, vinyls, hydrides, silanols, alkoxys, amines, epoxides, carbinols, and mercaptos. Examples of monomers that can be used to make the PDMS copolymer include, but are not limited to: phenylmethyl-, vinylmethyl-, diethyl-, methacryloxypropylmethyl-, acryloxypropylmethyl-, and alkylmethyl-siloxanes. The immuno-isolation membrane can be pre-cast from a biocompatible polymer such as poly(acrylonitrile-vinyl chloride) (PAN-PVC), for example using a phase-inversion process that can be optimized by individuals well-trained in the fields of biomaterials and polymer chemistry. The casting of the phase-inversion membrane (PIM) and the micro-patterning of the PDMS can be performed on the sensor assembly itself or on a temporary substrate such as a glass slide or silicon wafer (e.g. to form a separate part). A micro-patterned temporary substrate can also be used to create micro-wells in the PIM into which the PDMS could be patterned. In addition, individuals skilled in the art can employ various chemicals and techniques for promoting adhesion between the PDMS and the PIM. Examples include, but are not limited to the use of: functionalized PDMS derivatives, silanes, silane esters, functionalized silane esters, cross-linking agents, reactive polymer coatings (i.e. Lahann et al., 2003, *Anal. Chem.* 75: 2117-2122), plasma treatment, plasma polymerization, shadow masking, and chemical vapor deposition.

The permselective membranes containing poly(dimethylsiloxane) provide a variety of embodiments of the invention. One embodiment of the invention is a method of making a membrane for use with an implantable analyte sensor by forming a first layer of material comprising a biocompatible polymer composition that is impermeable to immunoglobulins yet permeable to oxygen, glucose and lactate, and then coupling the first layer to a second layer comprising functionalized poly(dimethyl siloxane), functionalized poly(dimethyl siloxane) copolymer or a mixture of functionalized poly(dimethyl siloxane) and functionalized poly(dimethyl siloxane) copolymer so that a membrane for use with an implantable analyte is made. In certain embodiments of the invention, first layer of material comprising a biocompatible polymer composition that is impermeable to immunoglobulins is termed a "immuno-isolation membrane". The membrane made by this method is more permeable to oxygen than it is to compounds having a higher molecular weight such as glucose and/or lactate. Composite membranes fashioned in such a manner can be made to possess a variety of morphologies, including those that are layered (FIG. 3), pore-filled (FIG. 4), or some combination thereof.

Illustrative chemically active groups that can be used to functionalize the PDMS and/or PDMS co-polymer include, but are not limited to: methacrylates, acrylates, vinyls, hydrides, silanols, alkoxys, amines, epoxides, carbinols, and mercaptos. Examples of monomers that can be used to make the PDMS copolymer include, but are not limited to: phenylmethyl-, vinylmethyl-, diethyl-, methacryloxypropylmethyl-, acryloxypropylmethyl-, and alkylmethyl-siloxanes. The other layer (e.g. the immuno-isolation membrane) can be pre-cast from a biocompatible polymer such as poly(acrylonitrile-vinyl chloride) (PAN-PVC), for example using a phase-inversion process that can be optimized by individuals well-trained in the fields of biomaterials and polymer chemistry. The casting of the phase-inversion membrane (PIM) and the micro-patterning of the PDMS can be performed on the sensor assembly itself or on a temporary substrate such as a glass slide or silicon wafer (e.g. to form a separate part). A micro-patterned temporary substrate can also be used to create micro-wells in the PIM into which the PDMS could be patterned. While certain embodiments of the invention include analyte sensors with composite membranes, the PDMS membrane may be used with or without a PIM in the final sensor assembly.

Embodiments of these membranes can be made using a variety of well know techniques. For example, in one illustrative embodiment, photolithography, lithographic molding, thick-film printing, plasma polymerization (with or without shadow-masking), or discrete nano-dispensing will be used to micro-pattern a curable PDMS functionalized derivative, co-polymer, or mixture thereof onto a pre-cast immuno-isolation membrane. In another embodiment of the invention, a curable PDMS derivative, co-polymer, or mixture thereof can be micro-patterned onto a temporary substrate using the described techniques. In the final sensor assembly, the stand-alone part may be used with a phase-inversion membrane that may either be cast as a separate part or on top of the PDMS (filling its pores). In an alternate embodiment, a curable PDMS derivative, co-polymer, or mixture thereof can be micro-patterned directly onto the sensor assembly, using the techniques described above. A PIM may be placed or cast on top of the micro-patterned PDMS.

Optionally, an adhesive layer disposed between the first and second layers of the membrane to promote adhesion between the first and second layers (as well as any other sensor layer where such an adhesive layer is appropriate). Various methods for promoting adhesion between the layers of the membrane may be employed by individuals skilled in the art. For example, a micro-patterned temporary substrate can also be used to create micro-wells in the PIM into which the PDMS could be patterned. In addition, individuals skilled in the art can employ various chemicals and techniques for promoting adhesion between the PDMS and the PIM. Examples include, but are not limited to the use of functionalized PDMS derivatives, silanes, silane esters, functionalized silane esters, cross-linking agents, reactive polymer coatings (see, e.g., Lahann et al., 2003, *Anal. Chem.* 75: 2117-2122), plasma treatment, plasma polymerization, shadow masking, and chemical vapor deposition.

In certain embodiments of the invention, the analyte sensor membrane can include additional layers having other compositions used in the manufacture of analyte sensors such as those described herein. In addition, in some embodiments of the invention, the first layer and/or the second layer of the membrane is constructed to include a plurality of pores. For example a laser can be used to micro-machine holes (e.g. of about 0.1 to about 1000 microns in size) into a formed piece of PDMS co-polymer (or another polymeric composition such as "silicone rubber") to form a microporous membrane. In some embodiments of the invention, at least one of the plurality of pores disposed in the second layer contains functionalized poly(dimethyl siloxane), functionalized poly(dimethyl siloxane) copolymer or a mixture of functionalized poly(dimethyl siloxane) and functionalized poly(dimethyl siloxane) copolymer of the first layer.

A related embodiment of the invention is a membrane made by the disclosed methods. One such embodiment of the invention is a membrane for use with an implantable analyte sensor which includes a first layer comprising a biocompatible polymer composition that is impermeable to immunoglobulins, yet permeable to oxygen, glucose and lactate; and a second layer coupled to the first layer comprising functionalized poly(dimethyl siloxane), functionalized poly(dimethyl siloxane) copolymer or a mixture of functionalized poly(dimethyl siloxane) and functionalized poly(dimethyl siloxane) copolymer. In certain embodiments of the invention, the membrane is designed to be more permeable to oxygen than glucose and/or lactate. In certain embodiments of the invention, the first and/or the second layers in the membrane comprises a plurality of pores. In certain embodiments of the invention, an adhesive layer disposed between the first and second layers, wherein the adhesive layer promotes adhesion between the first and second layers. Optionally, at least one of the plurality of pores disposed in the second layer contains functionalized poly(dimethyl siloxane), functionalized poly (dimethyl siloxane) copolymer or a mixture of functionalized poly(dimethyl siloxane) and functionalized poly(dimethyl siloxane) copolymer of the second layer. Yet another embodiment of the invention is an analyte sensor having a membrane disclosed above, for example an analyte sensor having a membrane made according the described methods. A related embodiment is a method of making an analyte sensor having such a membrane.

Another embodiment of the invention is a membrane for use with an implantable analyte sensor, the membrane including a first layer comprising a biocompatible polymer composition that is impermeable to immunoglobulins, yet permeable to oxygen, glucose and lactate; and a second layer coupled to the first layer comprising functionalized poly(dimethyl siloxane), functionalized poly(dimethyl siloxane) copolymer or a mixture of functionalized poly(dimethyl siloxane) and functionalized poly(dimethyl siloxane) copolymer. In this embodiment of the invention, the membrane is typically more permeable to oxygen than glucose and/or lactate.

Optionally in this membrane for use with an implantable analyte sensor the first layer and/or the second layer comprises a plurality of pores disposed therein. In certain embodiments of the invention, at least one of the plurality of pores disposed in the second layer contains functionalized poly (dimethyl siloxane), functionalized poly(dimethyl siloxane) copolymer or a mixture of functionalized poly(dimethyl siloxane) and functionalized poly(dimethyl siloxane) copolymer of the second layer. In some embodiments of the invention, an adhesive layer can be disposed between the first and second layers, wherein the adhesive layer promotes adhesion between the first and second layers.

Certain embodiments of the invention include one or more layers of a composition such as poly(dimethyl siloxane) glucose limiting membrane or the like that are constructed to include a plurality of pores. In some embodiments of the invention, the size and/or geometry of the pores can be controlled to facilitate a process that occurs in the sensor, for example a chemical and/or electrochemical process. In one such embodiment, FEMLAB programs were used to 3-D model glucose and oxygen transport properties through a membrane. FEMLAB is a program for modeling and solving scientific and engineering problems based on partial differential equations (see, e.g. S. Littmarck, et. al., Solving differential equations, *Industrial Physicist*, American Institute of Physics, February/March 2001; and S. Littmarck, et. al., Math, models, motion and more, *PT Design Magazine*, Penton Media (Cleveland, Ohio), May 2000). In a specific embodiment of the invention, FEMLAB software was used to identify and construct a sensor membrane that facilitates the occurrence of at least a 1:1 stoichiometric ratio between oxygen and glucose at the reactive surface of the electrode and typically a ratio where oyxgen is in a molar excess (e.g. as a means to address the oxygen deficit problem, see e.g. U.S. Pat. No. 6,784,274 which is incorporated herein by reference). This modeling further identifies membranes that help maintain linearity in current (Isig) under different concentrations of glucose. Using such modeling, in certain embodiments of the invention, the size and/or geometry of the pores is controlled to optimize the relative concentrations of glucose and oxygen that react with the glucose oxidase.

In certain embodiments of the invention the average diameter of the plurality of pores in the membrane used in the sensor is between 2 microns and 40 microns. In certain embodiments of the invention the average the average depth of the plurality of pores is between 50 microns and 250 microns. In a specific embodiments of the invention, the pores in the membrane are between 25-35 microns in diameter ands 90-110 microns in depth. One optimized embodiment of the invention has pores with a diameter of approximately 30 microns and a depth of approximately 100 microns. In certain embodiments, the pores in the permselective membrane have a diameter to depth aspect ratio geometry of about 0.3, for example a pore having dimensions where the diameter is 30 microns and the depth is 100 microns. In alternative embodiments, the diameter to depth aspect ratio geometry is between 0.25 and 0.35.

Optionally, one or more of the plurality of pores in the membrane also contains some amount of a biocompatible hydrophilic polymer. Such compositions can effect a number of desirable properties, and can for example facilitate the hydration of an implantable analyte sensor. Normal tendency when you immerse a sensor into solution is that, the tiny pores on the sensor membrane can trap air an inhibit the sensor's ability to get wet (hydration). This can result in reduced active sites for reaction to occur there by resulting in a non-linear sensor. To address this, one can use a material which can be used to fill the pore and aid in rapid hydration. Optionally, the biocompatible hydrophilic polymer enhances the wetting of a component in the sensor via capillary action. Typically, the hydrophilic polymer comprises an ethylene glycol or propylene glycol block copolymer or a mixture thereof. Optionally, the hydrophilic polymer is a hydrogel. Such hydrophilic polymers further act to increase the rate at which the surface of the sensor wets and in this way shortens the response time between the time that the sensor is inserted and its use. One illustrative hydrophilic polymer composition includes tetrahydrofuran, Jeffamine 900-propylene glycol-block-ethylene glycol-block-propylene, 1-2 diaminocyclohexane, Dibutyltin bis, 4,4" methylene bis and deionized water. Such compositions can be added to a pore containing membranes by any one of a variety of processes known in the art, for example dip and spay coating or filling and puddle casting. In certain embodiments of these processes, additional steps can be used to smooth/even topology of a sensor. For example, IPA exposure after these process typically helps even out the membrane (i.e. to give it a smooth/even topology).

In certain embodiments, the biocompatible hydrophilic polymer is selectively disposed in a subset of the plurality of pores, typically the largest pores. In a typical embodiment, the subset of the plurality pores have a diameter or depth that is at least 10%, 20%, 30%, 40% or 50% larger than the average diameter of the plurality of pores or at least 10%, 20%, 30%, 40% or 50% larger than the average depth of the plurality of pores.

A related embodiment of the invention is a method of making a membrane for use with an implantable analyte sensor generating a first layer comprising functionalized poly (dimethyl siloxane), functionalized poly(dimethyl siloxane) copolymer or a mixture of functionalized poly(dimethyl siloxane) and functionalized poly(dimethyl siloxane) copolymer; generating a second layer coupled to the first layer comprising a biocompatible polymer composition that is: impermeable to immunoglobulins; and permeable to oxygen, glucose and lactate so that a membrane is made that is more permeable to oxygen than glucose and/or lactate. Optionally in this method, the first layer and/or the second layer can be made to comprise a plurality of pores disposed therein. In certain embodiments of the invention, at least one of the plurality of pores disposed in the second layer is made to contain functionalized poly(dimethyl siloxane), functionalized poly(dimethyl siloxane) copolymer or a mixture of functionalized poly(dimethyl siloxane) and functionalized poly (dimethyl siloxane) copolymer of the second layer. In some embodiments of the method, an adhesive layer can be disposed between the first and second layers.

E. Microfabrication of Metallic Molds

A variety of methods for the microfabrication of polymerized compositions such as poly(dimethylsiloxane) or "PDMS" have been developed in recent years and are now commonly used for the construction of devices such as MEMS (micro-electromechanical systems) as well as in the micro-patterning of self-assembled monolayers (e.g. "soft lithography"). Typically, these methods involve the fabrication of a mold that is then filled with a polymerizable compositions (e.g. a PDMS pre-polymer), which is cured (polymerized) and then released to yield a microfabricated PDMS element.

The molds used in these procedures are usually fabricated using one of two different approaches. In the first such approach, the negative photoresist is coated, patterned via photolithography, and developed on a base substrate. In the second such approach, silicon wafers are etched to form a relief pattern. In this context, the fabrication of molds with small, high aspect ratio features remains a significant challenge. For example, molds with these extreme geometries typically have poor mechanical properties and can for example detach from the underlying substrate during polymer release.

Mathematical modeling predicts that a layer of microporous PDMS with a high aspect ratio can be used as the permselective membrane of the types used for example in enzymatic electrochemical glucose sensors. This mathematical modeling predicts that a sensor having such a membrane will exhibit a fast, linear response to glucose. Moreover, the well-known long-term stability of PDMS in vivo makes a permselective membrane attractive for use in a long-term implantable sensor such as the LTGS. Clearly, the microfabrication of a mold with small, high aspect ratio features that possess sufficient mechanical strength to withstand PDMS release is highly desirable. In this context, embodiments of the invention disclosed herein include novel microfabrication methods that produce molds with mechanically robust features that are smaller in size and/or possess higher aspect ratios than those that can be produced through methods previously described in the art.

Figure 11:
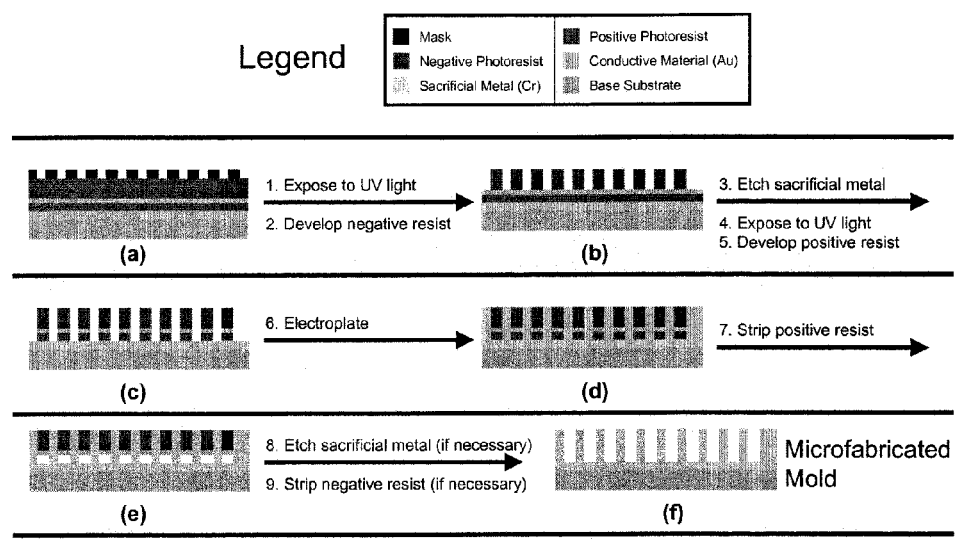
FIGS. 11A-11F provide an illustration of a process for the microfabrication of a mold.

FIG. 11 outlines an illustrative process for the microfabrication of a mold. To form the layered substrate depicted by FIG. 11(a), a base substrate formed from a material such as but not limited to glass, silicon, silicon nitride, or aluminum oxide is coated by a process such as sputtering with a conductive material such as but not limited to gold, silver, platinum, copper, or chrome. The base substrate may be pre-coated with a layer of chrome or titanium in order to promote adhesion of the top conductive layer. A positive photoresist such as AZ 4620 can then be applied by spin coating or by other methods familiar to those skilled in the art of microfabrication. After pre-baking, a sacrificial thin film of a metal such as chrome can be sputtered onto the layer of positive photo-resist. A negative photoresist such as SU-8 can be applied by spin coating or by other methods familiar to those skilled in the art. The layered substrate depicted in FIG. 11(b) can be obtained through standard photolithography and subsequent development of the negative resist. Chrome etch or another appropriate etchant can be used to remove the areas of the sacrificial metal layer exposed by the development of the negative resist. The substrate can then be re-exposed to UV light, with or without the use of a photomask. The positive resist can then be developed using an appropriate developing solvent, which can be selected by individuals skilled in the art. FIG. 11(c) depicts the resulting substrate, which can be electroplated with a conductive material such as, but not limited to gold, silver, platinum, copper, or chrome to yield the substrate depicted by FIG. 11(d). FIGS. 11(e-f) depict the final steps involved in the production of the microfabricated mold. The positive resist, sacrificial metal layer, and the negative resist can be removed from the substrate by exposing it to acetone or another solvent that can be selected by those skilled in the art. If deemed necessary, other solvents and/or etchants such as chrome etch and negative resist stripper can also be selected and applied by those skilled in the art. The resulting mold can be used repeatedly to microfabricate PDMS and other elastomers. The mold can also be used to microfabricate inelastic/hard materials in embodiments of the invention where the electroplated material can be removed by a chemical etchant or electrochemical oxidation.

One embodiment of the invention is a mold made by the methods described above. A related embodiment of the invention is a mold for forming a polymerized composition having a predetermined geometry comprising a metallic substrate capable of containing a polymerizable composition used as a permselective membrane. Another embodiment of the invention is a mold for forming a polymerized composition having a predetermined geometry comprising a metallic substrate capable of containing a polymerizable composition, where the polymerized composition produced by the mold is between about 1 and 1000, 10 and 100, 100 and 1000, 250 and 1000 or 500 and 1000 microns in thickness. Another embodiment of the invention is a mold for forming a polymerized composition having a predetermined geometry comprising a metallic substrate capable of containing a polymerizable composition, where the mold has sufficient mechanical strength to withstand release of a polymerized poly(dimethylsiloxane) composition without breaking. In certain embodiments of the invention, the mold has a two or more of these features.

One embodiment of the invention is a method of making a mold for forming a polymerized composition of a predetermined geometry by providing a base substrate; disposing a conductive layer on to (at least a portion) the base substrate; disposing a positive photoresist layer on to the conductive layer; disposing a sacrificial metal layer on to the positive photoresist layer; disposing a negative photoresist layer on to the sacrificial metal layer; developing the negative photoresist layer via UV photolithography (with or without the use of a photomask); removing the areas of the sacrificial metal layer exposed by the development of the negative resist layer using an etchant; exposing these components to UV photolithography; developing the positive photoresist layer via a developing solvent; electroplating these components with a layer of conductive material; and removing the positive photoresist layer, the sacrificial metal layer, and the negative photoresist layer from the so layered substrate using a solvent so that the mold is made. Typically, the mold made by the method can be used repeatedly. Other embodiments of the invention include a polymerized composition layer made using the described molds as well as analyte sensor including a polymerized composition layer made using the described molds.

In embodiments of the invention, the base substrate can be formed from a wide variety of materials such as glass, silicon, silicon nitride, aluminum oxide or the like. In certain embodiments of the invention the conductive material is disposed on the base by a process such as sputtering. Conductive materials for use in embodiments of the invention include gold, silver, platinum, copper, chrome or the like. In certain embodiments of the invention, the base substrate is coated with a layer of chrome or titanium prior to the application of the conductive material in order to promote adhesion of the base substrate and the conductive layer. In some embodiments of the invention, the substrate is baked prior to disposing the sacrificial metal layer on to the positive photoresist layer. Optionally in these methods, the negative photoresist layer and/or the positive photoresist layer is applied to the substrate by spin coating.

Another embodiment of the invention is a mold for forming a polymerized composition having a predetermined geometry comprising a metallic substrate capable of containing a polymerizable composition; where the pores in the polymerized composition produced by the mold have a diameter to depth aspect ratio geometry of about 0.3, for example a pore having dimensions where the diameter is 30 microns and the depth is 100 microns. In alternative embodiments, the diameter to depth aspect ratio geometry is between 0.25 and 0.35. Typically, the mold has sufficient mechanical strength to withstand release of a polymerized poly(dimethylsiloxane) composition without breaking. A related embodiment of the invention is a method of making a mold for forming a polymerized composition of a predetermined geometry comprising: providing a base substrate; disposing a conductive layer on to (a portion) the base substrate; disposing a positive photoresist layer on to the conductive layer; disposing a sacrificial metal layer on to the positive photoresist layer; disposing a negative photoresist layer on to the sacrificial metal layer; developing the negative photoresist layer via UV photolithography; removing the areas of the sacrificial metal layer exposed by the development of the negative resist layer using an etchant; exposing these components to UV photolithography (with or without the use of a photomask); developing the positive photoresist layer via a developing solvent; electroplating these components with a layer of conductive material; and then removing the positive photoresist layer, the sacrificial metal layer, and the negative photoresist layer from the so layered substrate using a solvent so that the mold is made. Typically, the mold made by the method can be used repeatedly. Optionally in this method, the base substrate is coated with a layer of chrome or titanium prior to the application of the conductive layer in order to promote adhesion of the base substrate and the conductive layer. Optionally, the substrate is baked prior to disposing the sacrificial metal layer on to the positive photoresist layer. Optionally the negative photoresist layer and/or the positive photoresist layer is applied to the substrate by spin coating.

III. Methods for Using Analyte Sensor Apparatus of the Invention

An embodiment of the invention is a method of sensing an analyte within the body of a mammal, the method comprising implanting an analyte sensor embodiment disclosed herein in to the mammal and then sensing an alteration in current at the working electrode and correlating the alteration in current with the presence of the analyte, so that the analyte is sensed. Typically the analyte sensor is polarized anodically such that the working electrode where the alteration in current is sensed is an anode. Alternatively the analyte sensor is polarized cathodically such that the working electrode where the alteration in current is sensed is an cathode. In one such method, the analyte sensor apparatus senses glucose in the mammal. In an alternative method, the analyte sensor apparatus senses lactate, potassium, calcium, oxygen, pH, and/or any physiologically relevant analyte in the mammal.

Certain analyte sensors having the structure discussed above have a number of highly desirable characteristics which allow for a variety of methods for sensing analytes in a mammal. For example in such methods, the analyte sensor apparatus implanted in the mammal functions to sense an analyte within the body of a mammal for more than 1, 2, 3, 4, 5, or 6 months. Typically, the analyte sensor apparatus so implanted in the mammal senses an alteration in current in response to an analyte within 15, 10, 5 or 2 minutes of the analyte contacting the sensor. In such methods, the sensors can be implanted into a variety of locations within the body of the mammal, for example in both vascular and non-vascular spaces.

IV. Kits and the Sensor Sets of the Invention

In another embodiment of the invention, a kit and/or sensor set, useful for the sensing an analyte as is described above, is provided. The kit and/or sensor set typically comprises a container, a label and an analyte sensor as described above. Suitable containers include, for example, an easy to open package made from a material such as a metal foil, bottles, vials, syringes, and test tubes. The containers may be formed from a variety of materials such as metals (e.g. foils) paper products, glass or plastic. The label on, or associated with, the container indicates that the sensor is used for assaying the analyte of choice. In some embodiments, the container holds a porous matrix that is coated with a layer of an enzyme such as glucose oxidase. The kit and/or sensor set may further include other materials desirable from a commercial and user standpoint, including elements or devices designed to facilitate the introduction of the sensor into the analyte environment, other buffers, diluents, filters, needles, syringes, and package inserts with instructions for use.

Various citations are referenced throughout the specification (e.g. U.S. Patent Application No. 20050115832, U.S. Pat. Nos. 6,001,067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391,250, 5,482,473, 5,299,571, 5,568,806, 5,494,562, 6,120,676, 6,542,765 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO03/036310 and WO 03/074107, and European Patent Application EP 1153571). The disclosures of all citations in the specification are expressly incorporated herein by reference.

EXAMPLES

Microfabricated PDMS

One strategy for the microfabrication of a PDMS membrane is to use 3-dimensional finite element modeling in combination with real-world mold microfabrication, PDMS molding, and sensor prototyping to facilitate production of optimized microfabricated permselective membranes. As described below, a mathematical model has been constructed from first-principles and a set of typical model assumptions. As shown below, the model equations have been successfully solved in a numerical fashion using FEMLAB software.

Microfabrication

Molds of a single repeating geometric pattern have been microfabricated thus far (see, e.g. FIG. 12A). These molds have produced microfabricated PDMS with a 30-micron pore size (D), a void fraction of 0.05 ($\phi$), and a thickness (H) of approximately 200-microns. The length of the repeating geometric pattern (L) can be calculated using Equation [2].

$$L = \sqrt{\frac{\pi D^2}{2(1-\phi)}} \quad [2]$$

Typical Model Assumptions
PDMS is impermeable to glucose.
The sensor signal is mass-transfer limited by the microfabricated membrane. Hence, glucose and oxygen are assumed to react instantaneously at the bottom of the pores of the membrane.
Glucose and oxygen react in a 1:1 stoichiometric ratio.
Glucose is the limiting reactant at all points on the reactive surface (its concentration is nearly zero). This assumption is valid for a finite combination of model input parameters and design geometries. The validity of this assumption holds as long as the numerical solution shows that the concentration of oxygen is greater than zero at all space and time points.

Model Equations
Species Conservation Equations for Glucose and Oxygen $$\frac{dC_{o\_pdms}}{dt} = D_{o\_pdms}\nabla^2 C_{o\_pdms} \quad [3]$$

$$\frac{dC_{o\_pore}}{dt} = D_{o\_pore}\nabla^2 C_{o\_pore} \quad [4]$$

$$\frac{dC_{g\_pore}}{dt} = D_{g\_pore}\nabla^2 C_{g\_pore} \quad [5]$$

Boundary Conditions for the PDMS/Bulk Fluid Interface $$C_{o\_pdms} = K_{o\_pdms} C_{o\_bulk} \quad [6]$$

Boundary Conditions for the Pore/Bulk Fluid Interface $$C_{o\_pore} = K_{o\_pore} C_{o\_bulk} \quad [7]$$

$$C_{g\_pore} = K_{g\_pore} C_{g\_bulk} \quad [8]$$

Boundary Conditions for the PDMS/Pore Interface $$K_{o\_pore} C_{o\_pdms} = K_{o\_pdms} C_{o\_pore} \quad [9]$$

$$\vec{n} \cdot \vec{\nabla} C_{g\_por} = 0 \quad [10]$$

Boundary Conditions for the Pore/Reactive Surface Interface $$C_{g\_pore} = 0 \quad [11]$$

$$\frac{\delta C_{o\_pore}}{\delta z} = \frac{D_{g\_pore}}{D_{o\_pore}} \frac{\delta C_{g\_pore}}{\delta z} \quad [12]$$

Boundary Conditions for the PDMS/Reactive Surface Interface $$\vec{n} \cdot \vec{\nabla} C_{o\_pdms} = 0 \quad [13]$$

Boundary Conditions for all Planes and Axes of Symmetry $$\vec{n} \cdot \vec{\nabla} C_{o\_pore} = 0 \quad [14]$$

$$\vec{n} \cdot \vec{\nabla} C_{o\_pdms} = 0 \quad [15]$$

$$\vec{n} \cdot \vec{\nabla} C_{g\_pore} = 0 \quad [16]$$

Model Geometry and Input Parameters

Figure 12B:
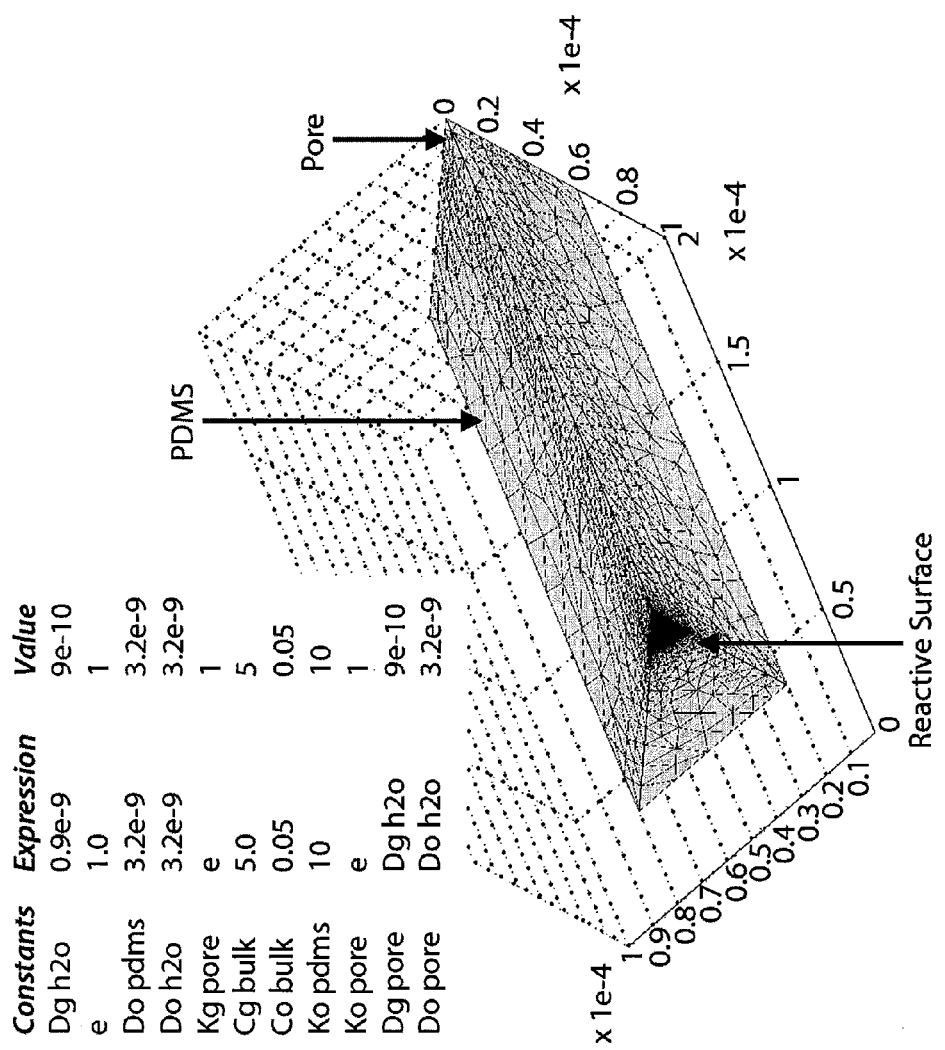

The planes and axes of symmetry of the repeating array of circles illustrated by FIG. 12A can be used to greatly simplify the geometry modeled by FEMLAB. FIG. 12B illustrates the three-dimensional wedge geometry used by FEMLAB to model the microfabricated PDMS membrane. Here the finite element mesh is shown to be refined near the reactive surface at the bottom of the PDMS pore. This was achieved using a "normal" global mesh setting along with a specified maximum element size of 0.2 microns for the reactive surface. In FIG. 12B, a screen shot of the input parameters (FEMLAB "constants" dialog box) is also provided, where all units are SI (glucose and oxygen concentrations in mM).

Model Solution

Figure 12C:
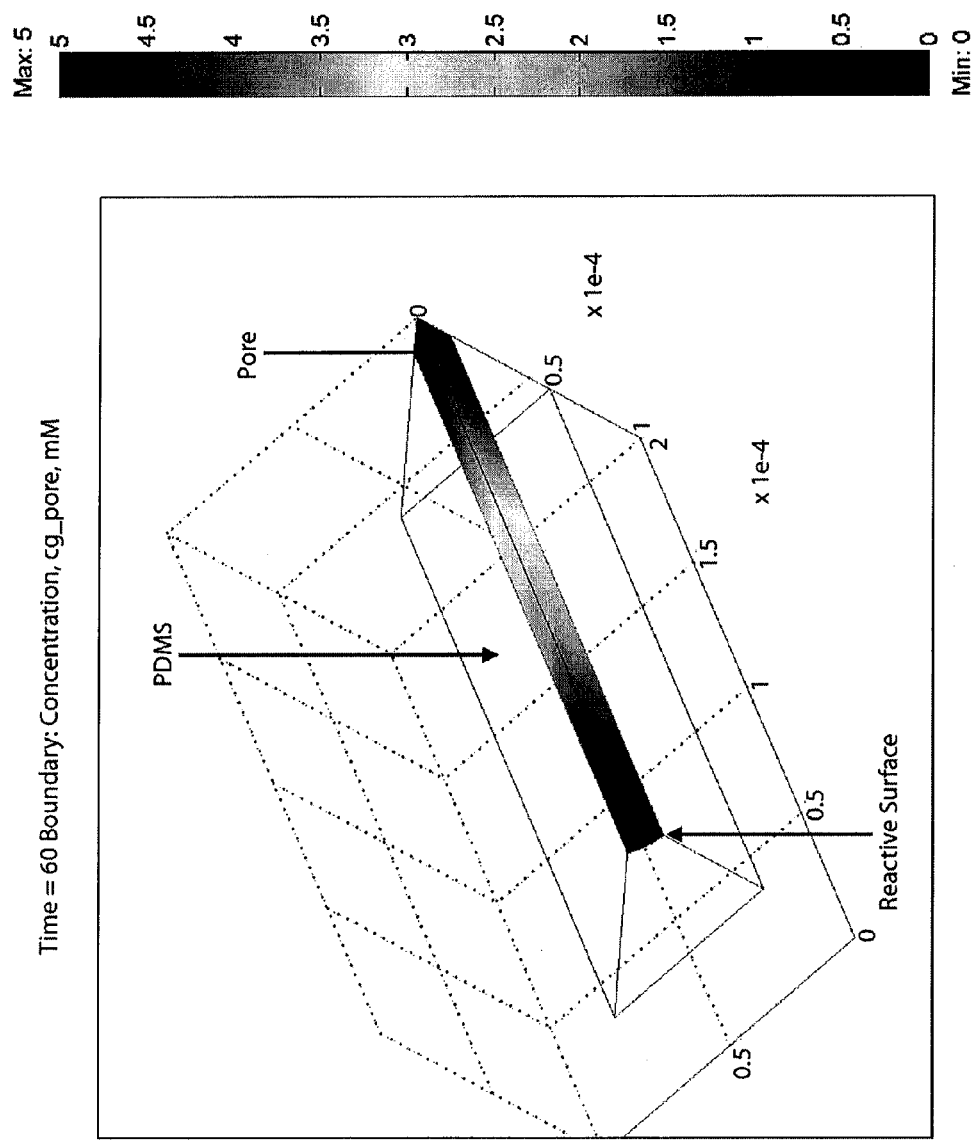

The FEMLAB model was solved using the time-dependent solver from 0 to 60 seconds. Initial conditions were zero glucose and ambient oxygen within the pore and PDMS subdomains. Other details of the solver parameters include the use of the GMRES linear system solver, the algebraic multigrid preconditioner, and the weak solution form. The symmetric matrices option was left unchecked (important!). The solution at 60 seconds was deemed to approximate the steady-state solution within acceptable error. FIG. 12C illustrates the steady-state glucose concentration profile in the pore. As expected, the glucose concentration decreases in a linear fashion from the pore opening to the reactive surface at the bottom.

Figure 12D:
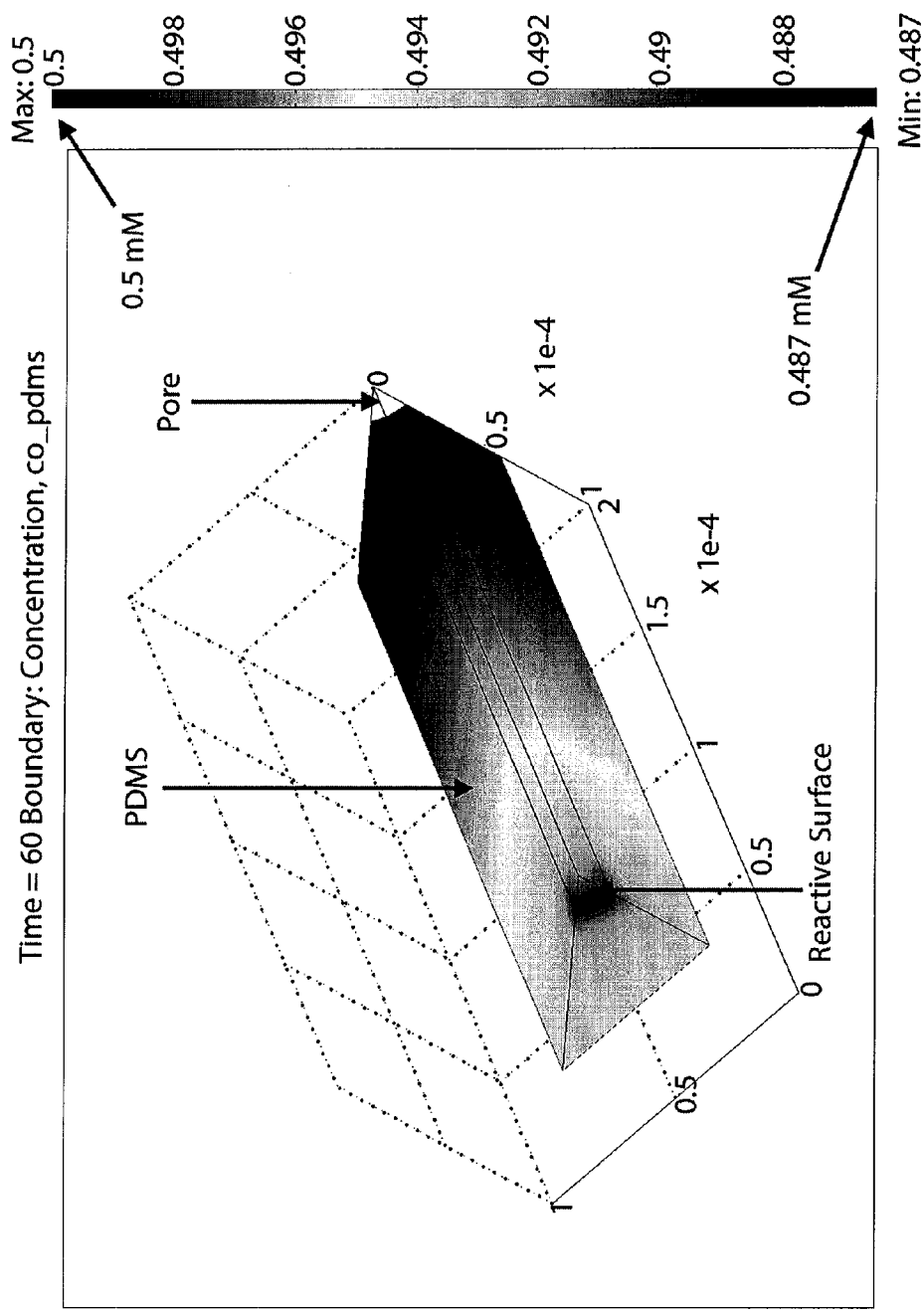

FIG. 12D illustrates the steady-state oxygen concentration profile within the PDMS. Along PDMS/bulk solution interface the oxygen concentration is 10-times greater than that found in the bulk (0.05 mM) due to the enhanced solubility of oxygen in PDMS relative to water. The oxygen concentration reaches a minimum along the edge that borders the reactive surface. The oxygen concentration decreases by less than 3%. This suggests that the pores in the microfabricated membrane could also be spaced more closely together, thereby allowing for increased glucose sensitivity.

Figure 12E:
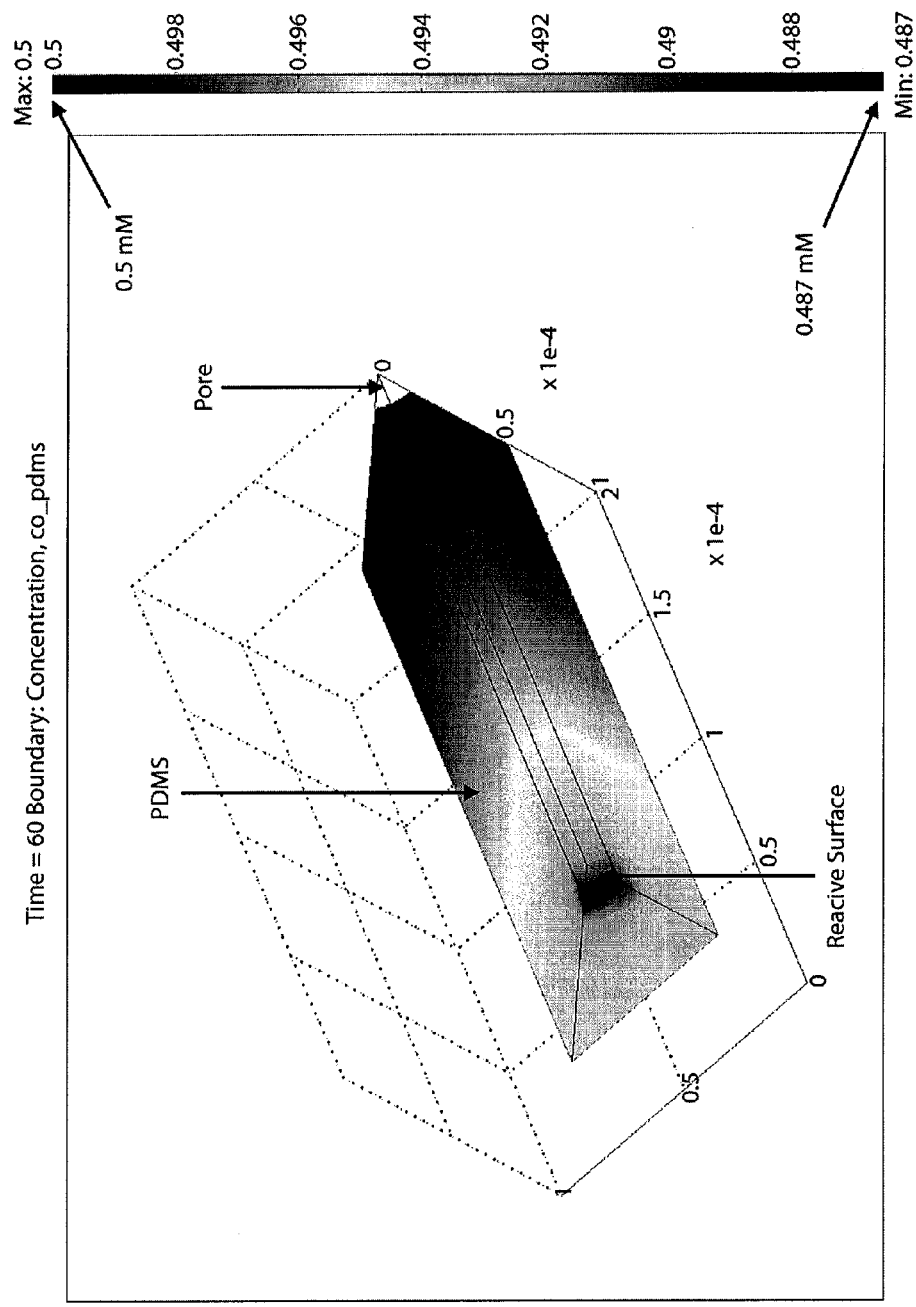
Figure 12F:
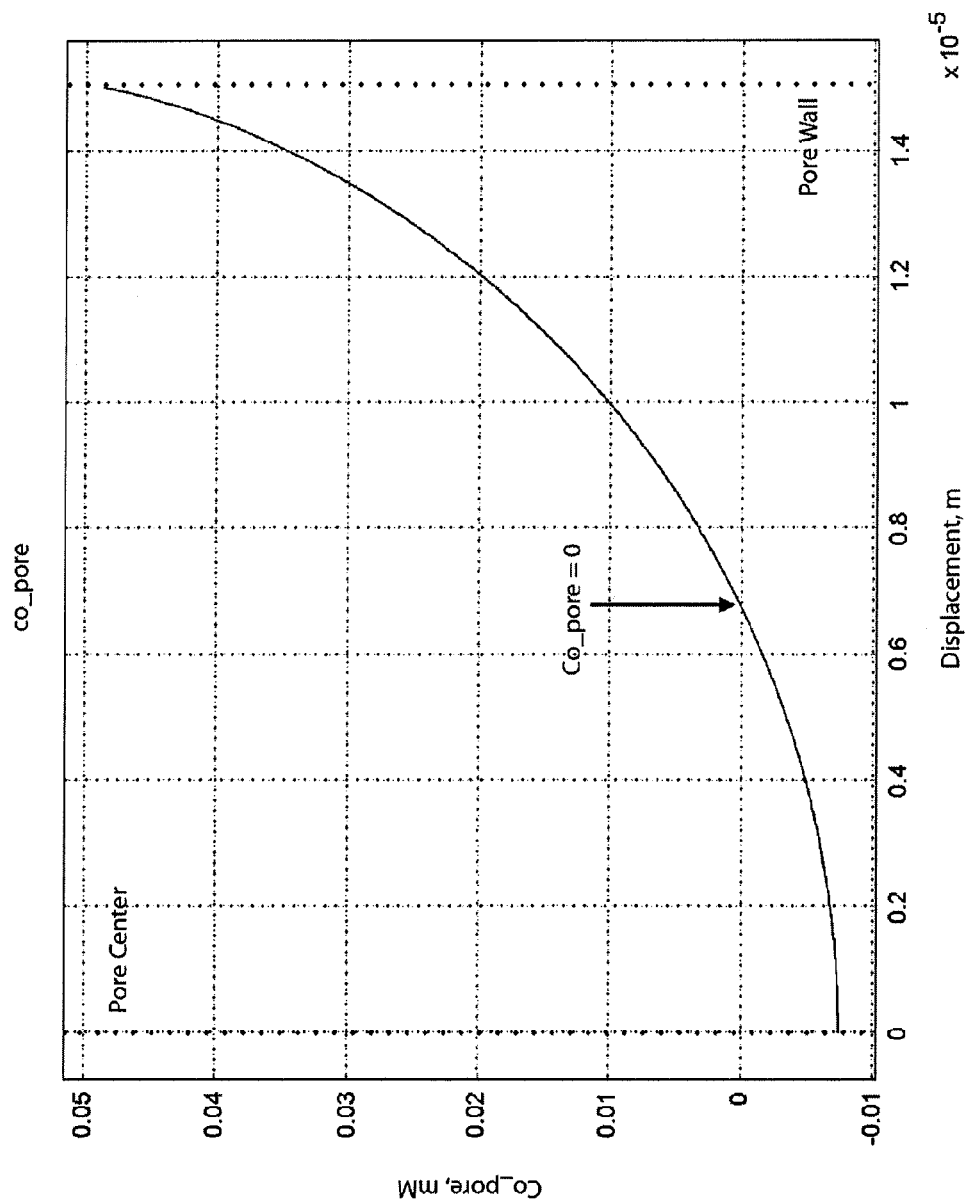

FIG. 12E illustrates the steady-state oxygen concentration profile within the microfabricated pore. Here it is shown that oxygen is depleted near the center of the pore, at and near the reactive surface. FIG. 12F illustrates this further, as it is shown that the oxygen concentration reaches zero along the reactive surface approximately 7 microns in from the pore wall. The FEMLAB model calculates negative oxygen concentrations, which are clearly not physically realizable. Nevertheless, the model serves its intended purpose: it predicts that a microporous PDMS membrane with this particular geometry will not behave as an ideal glucose limiting membrane for use in an enzymatic biosensor. Either the pore aspect ratio must be made more severe (thicker membrane and/or smaller pore diameter), or the pores must be filled with some sort of material that will further limit the diffusion of glucose (i.e. PES phase-inversion membrane).

Figure 12G:
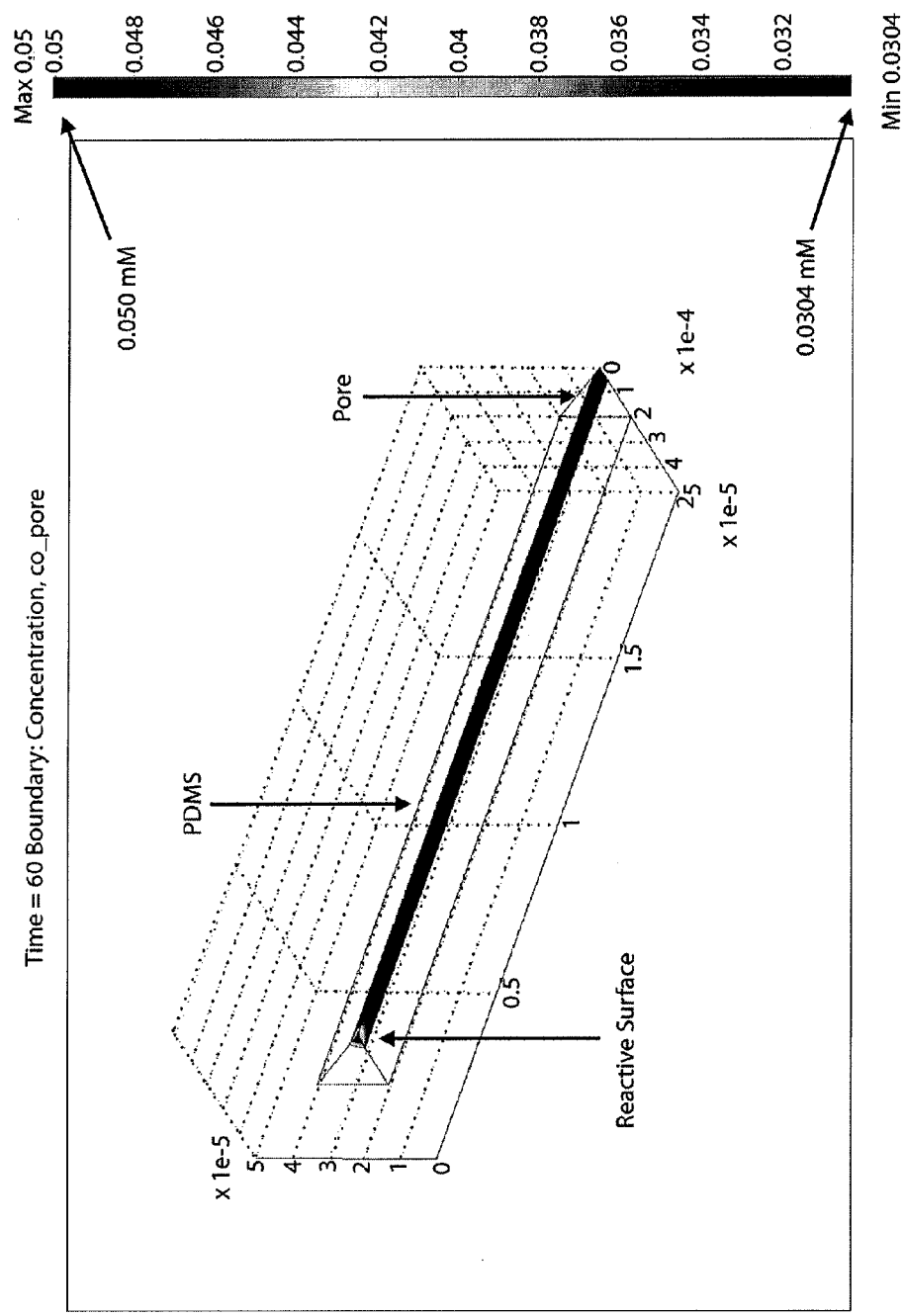
Figure 12H:
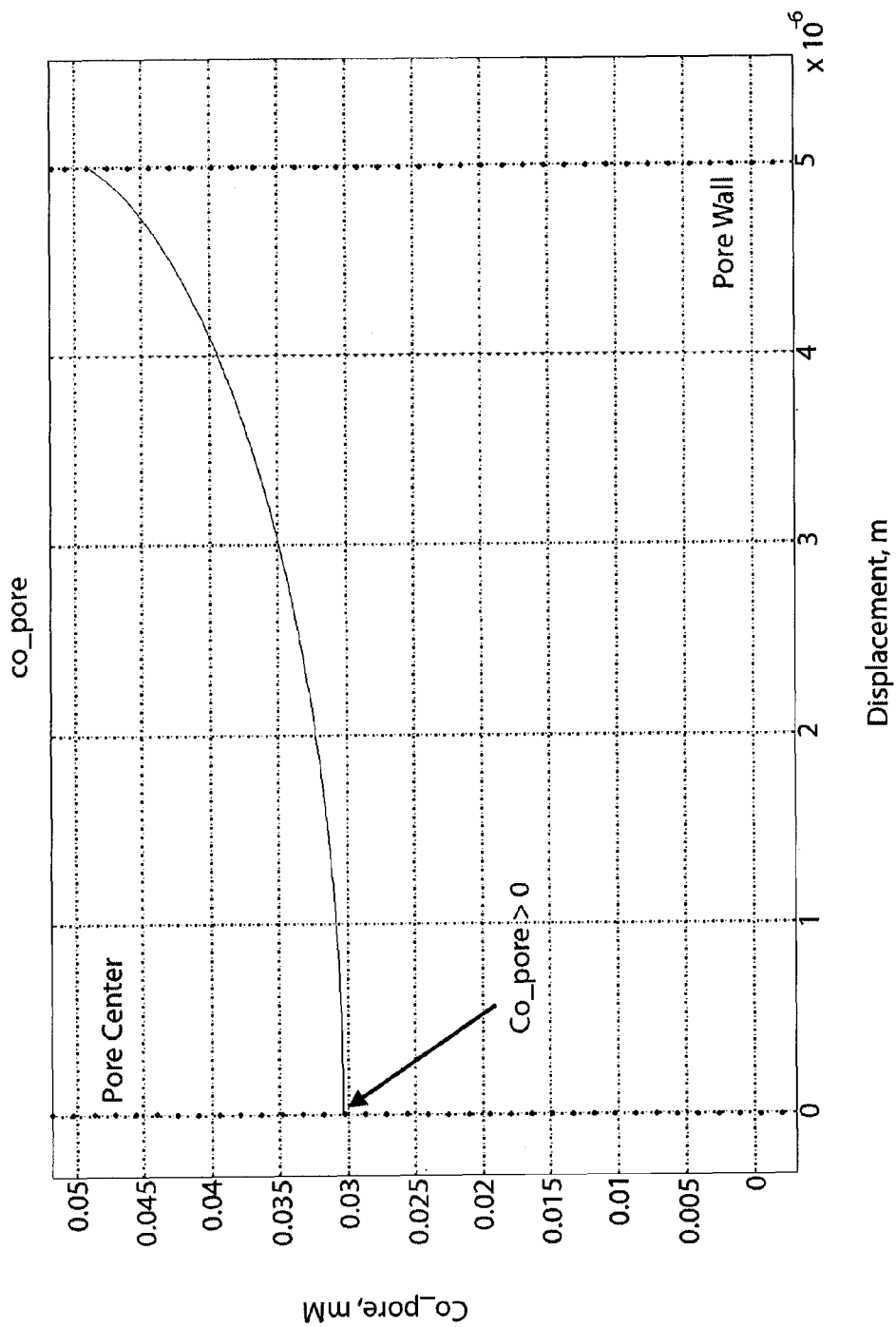

The effect of increasing the pore geometry aspect ratio on the oxygen concentration profile was investigated by re-scaling the FEMLAB model geometry such that D=10 μm, φ=0.05, and H=200 μm. FIG. 12G illustrates the steady-state oxygen concentration profile within the relatively narrow pore. Here it is shown that the increased aspect ratio of the pore geometry prevents oxygen from being depleted. FIG. 12H illustrates this more clearly, as it shows that the oxygen concentration never drops below 50% of the bulk value (0.05 mM). Hence, the model assumption that oxygen is present in molar excess of glucose at all points on the reactive surface holds true for this geometry and set of input parameters. Furthermore, the FEMLAB model predicts that a microporous PDMS of this geometry would behave as a nearly "ideal" permselective membrane as part of an enzymatic electrochemical glucose sensor. Finally, as is known in the art, further models can also be made that that take into account additional factors such as the diffusion and chemical reaction of glucose, oxygen, and peroxide within an immobilized enzyme layer of a finite thickness.

The invention claimed is:

1. A composition comprising a porous matrix comprising a lattice of spherical particles having a surface coated with an immobilized enzyme, wherein:
the porous matrix comprises a micro-porous metal that functions as an electrode in an electrochemical sensor, wherein the electrode consumes hydrogen peroxide in the electrochemical sensor;
the porous matrix is at least 10, 100, or 1000 microns thick; and
the composition is implantable within a mammal.

2. The composition of claim 1, wherein the enzyme is glucose oxidase, glucose dehydrogenase, lactate oxidase, hexokinase or lactate dehydrogenase.

3. The composition of claim 1, wherein the porous matrix has a surface area that is at least 2, 4, 6, 8, 10, 12, 14, 16 or 18 times the surface area of a non-porous matrix of same dimensions.

4. The composition of claim 1, wherein the enzyme coated on the surface is in a coating layer having a thickness selected from the group consisting of less than 1, 0.5, 0.25 and 0.1 microns.

5. The composition of claim 1, wherein the porosity range of the porous matrix is 40%-99%.

6. An analyte sensor apparatus for implantation within a mammal, the analyte sensor apparatus comprising a porous matrix comprising a lattice of
spherical particles having a surface coated with an immobilized enzyme, wherein:
the porous matrix comprises a micro-porous metal;
the porous matrix is at least 1 micron in thickness;
the immobilized enzyme is coated with an analyte modulating layer comprising a siloxane;
and
the porous matrix functions as a working electrode in the analyte sensor apparatus, and
wherein the electrode consumes hydrogen peroxide in the analyte sensor.

7. The analyte sensor apparatus of claim 6, wherein:
the immobilized enzyme is disposed within an analyte sensing layer disposed on the working electrode, such that the analyte sensing layer detectably alters the electrical current at the working electrode in the presence of an analyte.

8. The analyte sensor apparatus of claim 7, wherein:
the analyte modulating layer is disposed on the analyte sensing layer and, modulates the diffusion of oxygen therethrough.

9. The analyte sensor apparatus of claim 8, further comprising an adhesion promoting layer disposed on the analyte sensing layer, wherein the adhesion promoting layer promotes the adhesion between the analyte sensing layer and an analyte modulating layer disposed on the analyte sensing layer.

10. The analyte sensor apparatus of claim 8, further comprising a protein layer disposed between the analyte sensing layer and the analyte modulating layer.

11. The analyte sensor apparatus of claim 8, further comprising an interference rejection layer disposed between the surface of the working electrode and the analyte sensing layer.

12. The analyte sensor apparatus of claim 8, further comprising a cover layer disposed on at least a portion of the analyte modulating layer, wherein the cover layer further includes an aperture that exposes at least a portion of the analyte modulating layer to a solution comprising the analyte to be sensed.

13. A glucose sensor apparatus for implantation within a mammal, the apparatus comprising:
a counter electrode;
a reference electrode;
a working electrode comprising a porous matrix including a lattice of spherical micro-porous metal particles;
an analyte sensing layer comprising glucose oxidase coating the spherical micro-porous metal particles;
an analyte modulating layer coating the analyte sensing layer;
a protein layer comprising an albumin; and an adhesion promoting layer disposed on the analyte sensing layer, wherein the adhesion promoting layer promotes the adhesion between the analyte sensing layer and an analyte modulating layer disposed on the analyte sensing layer, and wherein the electrode consumes hydrogen peroxide in the analyte sensor.

14. The glucose sensor apparatus of claim 13, wherein the lattice of spherical micro-porous metal particles is at least 10, 100, or 1000 microns thick.

15. The glucose sensor apparatus of claim 13, further comprising an interference rejection layer.

16. The glucose sensor apparatus of claim 13, wherein the sensor comprises a plurality of working electrodes.

\* \* \* \* \*